(12) United States Patent
Gudmundsson et al.

(10) Patent No.: US 7,186,714 B2
(45) Date of Patent: Mar. 6, 2007

(54) IMIDAZO[1,2-α]PYRIDINE DERIVATIVES FOR THE PROPHYLAXIS AND TREATMENT OF HERPES VIRAL INFECTIONS

(75) Inventors: Kristjan Gudmundsson, Durham, NC (US); Brian A. Johns, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 321 days.

(21) Appl. No.: 10/479,526

(22) PCT Filed: Jun. 10, 2002

(86) PCT No.: PCT/US02/18520

§ 371 (c)(1),
(2), (4) Date: Dec. 2, 2003

(87) PCT Pub. No.: WO03/000689

PCT Pub. Date: Jan. 3, 2003

(65) Prior Publication Data

US 2005/0228004 A1    Oct. 13, 2005

Related U.S. Application Data

(60) Provisional application No. 60/300,009, filed on Jun. 21, 2001.

(51) Int. Cl.
C07D 471/04 (2006.01)
A61K 31/505 (2006.01)
C07D 401/04 (2006.01)

(52) U.S. Cl. ............... 514/231.8; 514/235.8; 514/275; 544/111; 544/122; 544/331

(58) Field of Classification Search ............ 544/111, 544/122, 331; 514/231.8, 235.8, 275
See application file for complete search history.

(56) References Cited

U.S. PATENT DOCUMENTS

| | | |
|---|---|---|
| 4,576,952 A | 3/1986 | Hurst et al. |
| 4,621,089 A | 11/1986 | Ward et al. |
| 4,670,432 A | 6/1987 | Ward et al. |
| 4,719,218 A | 1/1988 | Bender et al. |
| 4,794,114 A | 12/1988 | Bender et al. |
| 4,985,444 A | 1/1991 | Shiokawa et al. |
| 5,145,858 A | 9/1992 | Adams et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,700,816 A | 12/1997 | Isakson et al. |
| 5,990,148 A | 11/1999 | Isakson et al. |
| 6,136,839 A | 10/2000 | Isakson et al. |
| 6,207,675 B1 | 3/2001 | Carry et al. |
| 2004/0176396 A1* | 9/2004 | Biftu et al. ............. 514/259.1 |

FOREIGN PATENT DOCUMENTS

| | | |
|---|---|---|
| EP | 0 404 190 A1 | 6/1990 |
| EP | 0 404 190 B1 | 6/1990 |
| EP | 0403251 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |
| JP | 2001006877 | 6/1999 |
| WO | 0 364 204 A1 | 10/1989 |
| WO | WO 91 00092 | 1/1991 |
| WO | WO 91 19497 | 12/1991 |
| WO | WO 92/10190 | 6/1992 |
| WO | WO 92/10498 | 6/1992 |
| WO | WO 92/10499 | 6/1992 |
| WO | WO 95 00501 | 1/1995 |
| WO | WO 96 06840 | 3/1996 |

(Continued)

OTHER PUBLICATIONS

Bosseray et al., PubMed Abstract (Pathol Biol (Paris) 50(8):483-92), Oct. 2002.*
Razonable et al., PubMed Abstract (Herpes 10(3):60-5), Dec. 2003.*
Douglas, Jr. Introduction to Viral Diseases, Cecil Textbook of Medicine, 20th Edition, vol. 2, pp. 1739-1747, 1996.*
Vane, J. et al. "Towards a Better Aspirin." Nature, vol. 367, Jan. 20, 1994, pp. 215-216.
Carter, J. et al. "Recently Reported Inhibitors of Cyclooxygenase-2." Exp. Opin. Ther. Patents (1998), 8(1), pp. 21-29.

(Continued)

Primary Examiner—Deepak Rao
(74) Attorney, Agent, or Firm—Lorie Ann Morgan

(57) ABSTRACT

The present invention provides compounds of formula (I) wherein all variables are as defined herein, pharmaceutical compositions containing the same, processes for preparing the same and their use as pharmaceutical agents

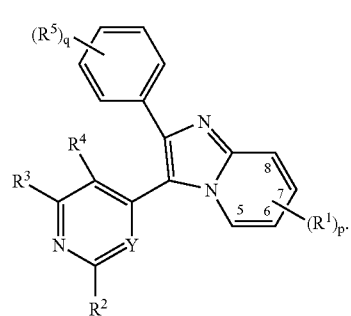

21 Claims, No Drawings

FOREIGN PATENT DOCUMENTS

| | | |
|---|---|---|
| WO | WO 96/16040 | 5/1996 |
| WO | WO 96 21667 | 7/1996 |
| WO | WO 96 31509 | 10/1996 |
| WO | WO 96/34866 | 11/1996 |
| WO | WO 96 41625 | 12/1996 |
| WO | WO 96 41626 | 12/1996 |
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |
| WO | WO 99 64419 | 12/1999 |
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 01/96335 | 12/2001 |
| WO | WO 02/16359 | 2/2002 |
| WO | WO 02 16359 | 2/2002 |
| WO | WO 02 18382 | 3/2002 |
| WO | WO 02/18382 | 3/2002 |
| WO | WO 02 48147 | 6/2002 |
| WO | WO 02/048148 | 6/2002 |
| WO | WO 02 066481 | 8/2002 |
| WO | WO 03/00682 | 1/2003 |

OTHER PUBLICATIONS

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.

Hanson, G.J., et al. "Pulmonary-Allergy, Dermatological, Gastrointestinal & Arthritis, Inhibitors of p38 kinase." Expert Opinion Ther. Patents, 1997, 7(7):729-733.

\* cited by examiner

IMIDAZO[1,2-α]PYRIDINE DERIVATIVES FOR THE PROPHYLAXIS AND TREATMENT OF HERPES VIRAL INFECTIONS

CROSS REFERENCE TO RELATED APPLICATIONS

This application is a 371 Application of PCT/US02/18520, filed 10 Jun. 2002, which claims priority to U.S. Application Ser. No. 60/300,009, filed 21 Jun. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

Varicella zoster virus (VZV) (also known as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin's lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

PCT Publication No. WO 91/00092 to SmithKline Beecham Corp. refers to imidazo[1,2-α]pyridine compounds of formula (I)

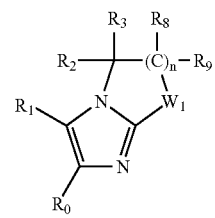

wherein:

W$_1$ is —(CR$_4$R$_5$)—(CR$_6$R$_7$)—, —CR$_5$=CR$_7$—, —N=CR$_7$—, —S(O)$_m$— or —O—; one of R$_1$ and R$_0$ is 4-pyridyl or C$_{1-4}$alkyl-4-pyridyl, provided that when R$_1$ is C$_{1-4}$alkyl-4-pyridyl the alkyl substituent is located at the 2-position of the pyridine ring, and the other of R$_1$ and R$_0$ is (a) phenyl or monosubstituted phenyl wherein said substituent is C$_{1-3}$alkylthio, C$_{1-3}$alkylsulfinyl, C$_{2-5}$1-alkenyl-1-thio, C$_{2-5}$1-alkenyl-1-sulfinyl, C$_{3-5}$2-alkenyl-1-thio, C$_{3-5}$2alkenyl-1-sulfinyl, 1-acyloxy-1-alkylthio, C$_{1-2}$alkoxy, halo, C$_{1-4}$alkyl or Z wherein Z is —S—S—Z$_1$ and Z$_1$ is phenyl or C$_{1-9}$alkyl; or (b) disubstituted phenyl wherein said substituents are independently C$_{1-3}$alkylthio, C$_{1-2}$alkoxy, halo or C$_{1-4}$alkyl; or (c) disubstituted phenyl wherein one of said substituents is C$_{1-3}$alkylsulfinyl, C$_{2-5}$1-alkenyl-1-thio, C$_{2-5}$1-alkenyl-1-sulfinyl, C$_{3-5}$2-alkenyl-1-thio, C$_{3-5}$2alkenyl-1-sulfinyl, or 1-acyloxy-1-alkylthio and the other is C$_{1-2}$alkoxy, halo or C$_{1-4}$alkyl; or (d) disubstituted phenyl wherein the substituents are the same and are C$_{1-3}$alkylsulfinyl, C$_{2-5}$1-alkenyl-1-thio, C$_{2-5}$1-alkenyl-1-sulfinyl, C$_{3-5}$2-alkenyl-1-thio, C$_{3-5}$2alkenyl-1-sulfinyl, or 1-acyloxy-1-alkylthio or wherein the substituents together form a methylene dioxy group; or (e) monosubstituted phenyl wherein said substituent is

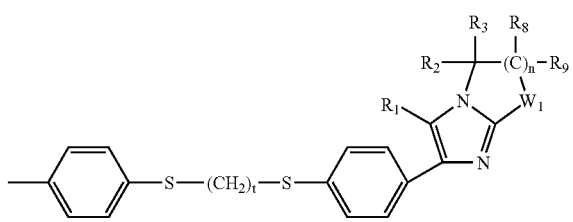

t is 0 or 1; W$_1$, R$_1$, R$_2$, R$_3$, R$_4$, R$_5$, R$_6$, R$_7$, R$_8$ and R$_9$ are as defined herein;

provided that:

1) when W$_1$ is —(CR$_4$R$_5$)—(CR$_6$R$_7$)— then
   n is 0 or 1;
   and R$_2$, R$_3$, R$_4$, R$_5$, R$_6$, R$_7$, R$_8$ and R$_9$ are independently —H or C$_{1-2}$alkyl; and
   when R$_1$ or R$_0$ is 4-pyridyl, the other of R$_1$ and R$_0$ is other than mono-C$_{1-2}$alkoxy-substituted phenyl or mono-halo-substituted phenyl; or
   when n is 0, R$_4$ and R$_5$ together are oxo; R$_4$ and R$_5$ are both fluoro, or one of R$_4$ and R$_5$ is H and the other is OH;

2) when W$_1$ is —CR$_5$=CR$_7$— or —N=CR$_7$— then
   n is 1;
   R$_3$, R$_5$, R$_7$ and R$_9$ are independently —H or C$_{1-2}$alkyl; and
   R$_2$ and R$_8$ together represent a double bond in the B ring such that the
   B ring is an aromatic pyridine or pyrimidine ring;

3) when W$_1$ is —S(O)$_m$— then
   m is 0, 1 or 2;
   n is 1 or 2;
   R$_3$ and R$_9$ are independently —H or C$_{1-2}$alkyl;
   R$_2$ and R$_8$ are independently —H or C$_{1-2}$alkyl or R$_2$ and R$_8$ together represent a double bond in the B ring such that the B ring is an aromatic thiazole ring;

further provided that:

(a) when R$_2$ and R$_8$ are independently —H or C$_{1-2}$alkyl and R$_1$ or R$_0$ is 4-pyridyl, then the other of R$_1$ and R$_0$ is other than mono-C$_{1-2}$alkoxy-substituted phenyl or mono-halo-substituted phenyl; and (b) when R$_2$ and R$_8$ together represent a double bond in the B ring such that the B ring is an aromatic thiazole ring, the m is 0 and n is 1; and 4) when W$_1$ is —O— then
   n is 1;
   R$_3$ and R$_9$ are independently —H or C$_{1-2}$alkyl; and
   R$_2$ and R$_8$ together represent a double bond in the B ring such that the B ring is an aromatic oxazole ring;

or a pharmaceutically acceptable salt thereof for use in the inhibition of interleukin-1 and tumor necrosis factor production by monocytes and/or macrophages.

U.S. Pat. No. 5,498,774 and European Patent No. 0 404 190 to Mitsudera et al., relates to condensed heterocyclic compounds of the formula (I):

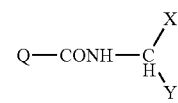

wherein Q is a condensed heterocyclic group having a nitrogen atom in the bridgehead which is unsubstituted or substituted, X is a hydrogen atom or a group bonded through C, O, S or N, and Y is an electron attractive group; or its salt which is useful as an agricultural chemical.

BRIEF SUMMARY OF THE INVENTION

The present invention provides a compound of formula (I):

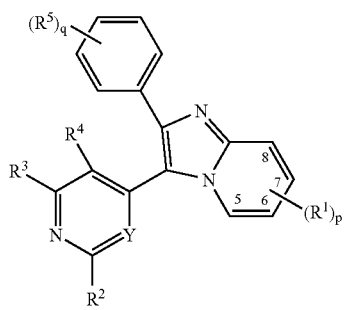

wherein:

p is 0, 1, 2, 3 or 4;

each R$^1$ is the same or different and is independently selected from the group consisting of halo, alkyl, alkenyl, alkynyl, cycloalkyl, cycloalkenyl, Ay, Het, —OR$^7$, —OAy, —OR$^{10}$Ay, —OHet, —OR$^{10}$Het, —C(O)R$^9$, —C(O)Ay, —C(O)Het, —CO$_2$R$^9$, —C(O)NR$^7$R$^8$, —C(O)NR$^7$Ay, —C(O)NHR$^{10}$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Ay, —R$^{10}$Het, —R$^{10}$O—C(O)R$^9$, —R$^{10}$O—C(O)Ay, —R$^{10}$O—C(O)Het, —R$^{10}$O—S(O)$_n$R$^9$, —R$^{10}$OR$^9$, —R$^{10}$C(O)R$^9$, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R¹ groups together with the atoms to which they are bonded form a $C_{5-6}$cycloalkyl or a 5 or 6-membered heterocyclic ring containing 1 or 2 heteroatoms;

each R⁷ and R⁸ are the same or different and are independently selected from the group consisting of H, alkyl, cycloalkyl, alkenyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R¹⁰, —R¹⁰SO₂NR⁹R¹¹, —R¹⁰SO₂NHCOR⁹, —R¹⁰NR⁹R¹¹, —R¹⁰NHCOR⁹, —R¹⁰NHSO₂R⁹ and —R¹⁰NHC(NH)NR⁹R¹¹;

each R⁹ and R¹¹ are the same or different and are independently selected from the group consisting of H, alkyl, cycloalkyl, —R¹⁰cycloalkyl, —R¹⁰OH, —R₁₀(OR¹⁰)$_w$ where w is 1–10, and —R¹⁰NR¹⁰R¹⁰;

each R¹⁰ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

R² is selected from the group consisting of halo, alkenyl, cycloalkyl, cycloalkenyl, Ay, Het, —OR⁷, —OAy, —OHet, —OR¹⁰Het, —S(O)$_n$R⁹, —S(O)$_n$Ay, —S(O)$_n$NR⁷R⁸, —S(O)$_n$Het, —NR⁷R⁸, —NHHet, —NHR¹⁰Ay, —NHR¹⁰Het, —R¹⁰NR⁷R⁸ and —R¹⁰NR⁷Ay;

n is 0, 1 or 2;

Y is N or CH;

R³ and R⁴ are the same or different and are each independently selected from the group consisting of H, halo, alkyl, alkenyl, cycloalkyl, Ay, Het, —OR⁷, —OAy, —C(O)R⁷, —C(O)Ay, —CO₂R⁷, —CO₂Ay, —SO₂NHR⁹, —NR⁷R⁸, —NR⁷Ay, —NHHet, —NHR¹⁰Het, —R¹⁰cycloalkyl, —R¹⁰OR⁷, —R¹⁰OAy, —R¹⁰NR⁷R⁸ and —R¹⁰NR⁷Ay;

q is 0, 1, 2, 3, 4 or 5; and each R⁵ is the same or different and is independently selected from the group consisting of halo, alkyl, alkenyl, alkynyl, cycloalkyl, cycloalkenyl, Ay, Het, —OR⁷, —OAy, —OHet, —OR¹⁰Ay, —OR¹⁰Het, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R⁵ groups together with the atoms to which they are bonded form a $C_{5-6}$ cycloalkyl or aryl;

wherein when Y is CH, R³ is not —NR⁷Ay;

and pharmaceutically acceptable salts, solvates and physiologically functional derivatives thereof.

The present invention also provides a pharmaceutical composition comprising a compound of formula (I). In one embodiment, the pharmaceutical composition further comprises a pharmaceutically acceptable carrier or diluent. In one embodiment, the pharmaceutical composition further comprises an antiviral agent selected from the group consisting of aciclovir and valaciclovir.

The present invention also provides a method for the prophylaxis or treatment of a herpes viral infection in an animal. The method comprises administering a therapeutically effective amount of a compound of formula (I) or a pharmaceutically acceptable salt, solvate or physiologically functional derivative thereof. The herpes viral infection can be any of herpes simplex virus 1, herpes simplex virus 2, cytomegalovirus, Epstein Barr virus, varicella zoster virus, human herpes virus 6, human herpes virus 7, and human herpes virus 8.

The present invention also provides a method for the prophylaxis or treatment of conditions or diseases associated with a herpes viral infection in an animal. The method comprises administering to the animal a therapeutically effective amount of the compound of formula (I) or a pharmaceutically acceptable salt, solvate or physiologically functional derivative thereof.

The present invention also provides a process for preparing compounds of formula (I) wherein Y is N; R² is selected from the group consisting of alkenyl, cycloalkyl, cycloalkenyl, Ay, Het, —OR⁷, —OAy, —OHet, —OR¹⁰Het, —S(O)$_n$R⁹, —S(O)$_n$Ay, —S(O)$_n$NR⁷R⁸, —S(O)$_n$Het, —NR⁷R⁸, —NHHet, —NHR¹⁰Ay, —NHR¹⁰Het, —R¹⁰NR⁷R⁸ and —R¹⁰NR⁷Ay; and R³ and R⁴ are both H. The process comprises reacting a compound of formula (VI):

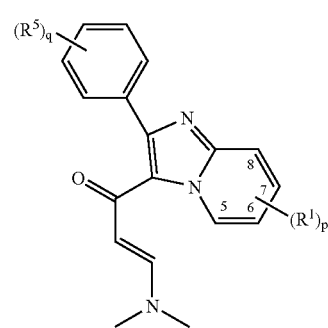

VI wherein p, R¹, q, and R⁵ are as defined above in connection with compounds of formula (I);

with a compound of formula (VII)

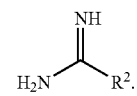

VII

In another aspect, the present invention provides a process for preparing compounds of formula (I) wherein Y is N; R² is selected from the group consisting of alkenyl, cycloalkyl, cycloalkenyl, Ay, Het, —OR⁷, —OAy, —OHet, —OR¹⁰Het, —S(O)$_n$R⁹, —S(O)$_n$Ay, —S(O)$_n$NR⁷R⁸, —S(O)$_n$Het, —NR⁷R⁸, —NHHet, —NHR¹⁰Ay, —NHR¹⁰Het, —R¹⁰NR⁷R⁸ and —R¹⁰NR⁷Ay; R³ is selected from the group consisting of H, alkyl, alkenyl, cycloalkyl, Ay, Het, —C(O)R⁷, —CO₂R⁷, —SO₂NHR⁹, —NR⁷R⁸ (where R⁷ and $R^8$ are not H), $-R^{10}OR^7$ and $-R^{10}NR^7R^8$; and $R^4$ is H. The process comprises reacting a compound of formula (XI):

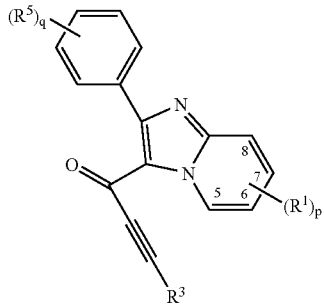

XI wherein p, $R^1$, q and $R^5$ are as defined above in connection with compounds of formula (I);

with a compound of formula (VII)

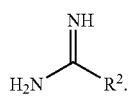

VII

The present invention provides another process for preparing compounds of formula (I) wherein Y is N and $R^2$ is selected from the group consisting of alkenyl, cycloalkyl, cycloalkenyl, Ay, Het, $-OR^7$, $-OAy$, $-OHet$, $-OR^{10}Het$, $-S(O)_nR^9$, $-S(O)_nAy$, $-S(O)_nNR^7R^8$, $-S(O)_nHet$, $-NR^7R^8$, $-NHHet$, $-NHR^{10}Ay$, $-NHR^{10}Het$, $-R^{10}NR^7R^8$ and $-R^{10}NR^7Ay$. The process comprises reacting a compound of formula (XIV):

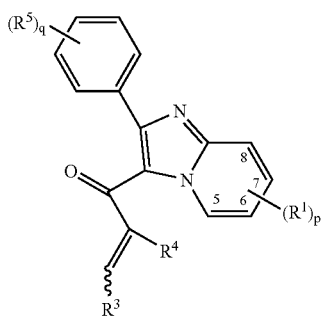

XIV wherein p, $R^1$, $R^3$, $R^4$, q and $R^5$ are as defined above in connection with compounds of formula (I);

with a compound of formula (VII)

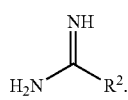

VII

The present invention provides another process for preparing compounds of formula (I). The process comprises reacting a compound of formula (XV):

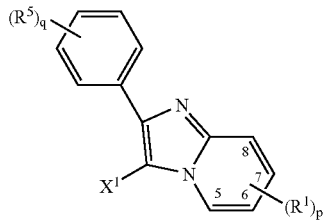

XV wherein p, $R^1$, q and $R^5$ are as defined above in connection with compounds of formula (I) and $X^1$ is halo;

with a compound of formula (XVI)

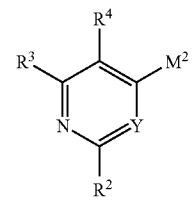

XVI wherein Y, $R^2$, $R^3$ and $R^4$ are as defined above in connection with compounds of formula (I) and $M^2$ is selected from the group consisting of $-B(OH)_2$, $-B(ORa)_2$, $-B(Ra)_2$, $-Sn(Ra)_3$, Zn-halide, ZnRa, and Mg-halide where Ra is alkyl or cycloalkyl and halide is halo.

The present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

The present invention provides a compound of formula (I) for use in therapy.

The present invention provides a compound of formula (I) for use in the prophylaxis or treatment of a herpes viral infection in an animal, particularly a human.

The present invention provides a compound of formula (I) for use in the prophylaxis or treatment of conditions or diseases associated with a herpes viral infection in an animal, particularly a human.

The present invention provides the use of a compound of formula (I) for the preparation of a medicament for the prophylaxis or treatment of a herpes viral infection in an animal, particularly a human.

The present invention provides the use of a compound of formula (I) for the preparation of a medicament for the treatment or prophylaxis of conditions or diseases associated with a herpes viral infection in an animal, particularly a human. The present invention also provides a pharmaceutical composition comprising a compound of formula (I) for use in the prophylaxis or treatment of a herpes viral infection in an animal, particularly a human.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolateable intermediates such as for example, compounds of formula (VI), (XI), XIV), and (XV), the phrase "a compound of formula "(number)" means a compound having that formula and pharmaceutically acceptable salts, solvates and physiologically functional derivatives thereof.

As used herein, the terms "alkyl" (and alkylene) refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" and "alkylene" also include substituted alkyl and substituted alkylene. The alkyl groups may be optionally substituted with one or more substituents selected from the group consisting of mercapto, nitro, cyano and halo. Perhalo alkyl, such as trifluoromethyl is one particular alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl also includes substituted cycloalkyl. The cycloalkyl may be optionally substituted on any available carbon(s) with one or more substituents selected from the group consisting of mercapto, nitro, cyano, halo and alkyl.

As used herein, the term "alkenyl" refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted on any available carbon(s) with one or more substituents selected from the group consisting of mercapto, nitro, cyano, halo and alkyl.

As used herein, the term "cycloalkenyl" refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cyclalkenyl. The cycloalkenyl may optionally be substituted on any available carbon(s) with one or more substituents selected from the group consisting of mercapto, nitro, cyano, halo and alkyl.

As used herein, the term "alkynyl" refers to straight or branched hydrocarbon chains containing from 2 to 8 carbon atoms and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted on any available carbon(s) with one or more substituents selected from the group consisting of mercapto, nitro, cyano, halo and alkyl.

The term "halo" or "halogen" refers to the elements fluorine, chlorine, bromine and iodine.

The term "Ay" refers to monocyclic carbocyclic groups and fused bicyclic carbocyclic groups having from 5 to 12 carbon atoms (unless otherwise specified) and having at least one aromatic ring. Examples of particular aryl groups include but are not limited to phenyl, and naphthyl. "Aryl" also includes substituted aryl. Aryl groups may optionally be substituted on any available carbon(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred aryl groups according to the invention include but are not limited to phenyl and substituted phenyl.

The term "heterocyclic" (or "heterocycle") refers to monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic groups may optionally be substituted on any available carbon(s) or heteroatom(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred heterocyclic groups according to the invention include but are not limited to pyrrolidine, piperidine, morpholine, thiomorpholine and piperazine, and substituted variants thereof.

The term "heteroaryl" refers to aromatic monocyclic groups and aromatic fused bicyclic groups (wherein at least one ring is aromatic) having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl groups may optionally be substituted on any available carbon(s) or heteroatom(s) with one or more substituents selected from the group consisting of halo, alkyl (including perhaloalkyl), alkenyl, cycloalkyl, cycloalkenyl, hydroxy, alkoxy, cycloalkoxy, alkylhydroxy, mercapto, amino, alkylamine, cycloalkylamine, Het, amidine, carboxy, carboxamide, sulfonamide, cyano, nitro and azido. Preferred heteroaryl groups according to the invention include but are not limited to pyridine, furan, thiophene, pyrrole, imidazole, pyrazole, and pyrimidine, and substituted variants thereof.

The term "members"(and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine. As used herein, the term "optionally" means that the subsequently described event(s) may or may not occur, and includes both event(s) that occur and events that do not occur.

The present invention provides compounds of formula formula (I):

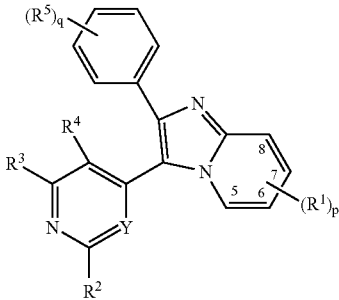

wherein:
p is 0, 1, 2, 3 or 4;
each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$R^{10}$Het, —C(O)$R^9$, —C(O)Ay, —C(O)Het, —$CO_2R^9$, —C(O)$NR^7R^8$, —C(O)$NR^7$Ay, —C(O)$NHR^{10}$Ay, —C(O)$NHR^{10}$Het, —C(S)$NR^9R^{11}$, —C(NH)$NR^7R^8$, —C(NH)$NR^7$Ay, —S(O)$_n$$R^9$, —S(O)$_n$Ay, —S(O)$_n$Het, —S(O)$_2$$NR^7R^8$, —S(O)$_2$$NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—C(O)$R^9$, —$R^{10}$O—C(O)Ay, —$R^{10}$O—C(O)Het, —$R^{10}$O—S(O)$_n$$R^9$, —$R^{10}$O$R^9$, —$R^{10}$C(O)$R^9$, —$R^{10}$CO$_2R^9$, —$R^{10}$C(O)$NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH)$NR^9R^{11}$, —$R^{10}$SO$_2$$R^9$, —$R^{10}$SO$_2$$NR^9R^{11}$, —$R^{10}$SO$_2$NHCOR$^9$, —$R^{10}NR^7R^8$, —$R^{10}NR^7$Ay, —$R^{10}$NHC(NH)$NR^9R^{11}$, cyano, nitro and azido; or
two adjacent $R^1$ groups together with the atoms to which they are bonded form a $C_{5-6}$cycloalkyl or a 5 or 6-membered heterocyclic ring containing 1 or 2 heteroatoms;
each $R^7$ and $R^8$ are the same or different and are independently selected from the group consisting of H, alkyl, cycloalkyl, alkenyl, cycloalkenyl, —$OR^9$, —C(O)$R^9$, —CO$_2R^9$, —C(O)$NR^9R^{11}$, —C(S)$NR^9R^{11}$, —C(NH)$NR^9R^{11}$, —SO$_2R^{10}$, —SO$_2NR^9R^{11}$, —$R^{10}$cycloalkyl, —$R^{10}OR^9$, —$R^{10}$C(O)$R^9$, —$R^{10}$CO$_2R^9$, —$R^{10}$C(O)$NR^9R^{11}$, —$R^{10}$C(S)$NR^9R^{11}$, —$R^{10}$C(NH)$NR^9R^{11}$, —$R^{10}$SO$_2R^{10}$, —$R^{10}$SO$_2NR^9R^{11}$, —$R^{10}$SO$_2$NHCOR$^9$, —$R^{10}NR^9R^{11}$, —$R^{10}$NHCOR$^9$, —$R^{10}$NHSO$_2R^9$ and —$R^{10}$NHC(NH)$NR^9R^{11}$;
each $R^9$ and $R^{11}$ are the same or different and are independently selected from the group consisting of H, alkyl, cycloalkyl, —$R^{10}$cycloalkyl, —$R^{10}$OH, —$R^{10}$(OR$^{10}$)$_w$ where w is 1–10, and —$R^{10}NR^{10}R^{10}$;
each $R^{10}$ is the same or different and is independently selected from the group consisting of alkyl, alkenyl, alkynyl, cycloalkyl and cycloalkenyl;
Ay is aryl;
Het is a 5- or 6-membered heterocyclic or heteroaryl group;
$R^2$ is selected from the group consisting of halo, alkenyl, cycloalkyl, cycloalkenyl, Ay, Het, —$OR^7$, —OAy, —OHet, —$OR^{10}$Het, —S(O)$_n$$R^9$, —S(O)$_n$Ay, —S(O)$_n$$NR^7R^8$, —S(O)$_n$Het, —$NR^7R^8$, —NHHet, —$NHR^{10}$Ay, —$NHR^{10}$Het, —$R^{10}NR^7R^8$ and —$R^{10}NR^7$Ay;
n is 0, 1 or 2;
Y is N or CH;
$R^3$ and $R^4$ are the same or different and are each independently selected from the group consisting of H, halo, alkyl, alkenyl, cycloalkyl, Ay, Het, —$OR^7$, —OAy, —C(O)$R^7$, —C(O)Ay, —CO$_2R^7$, —CO$_2$Ay, —SO$_2NHR^9$, —$NR^7R^8$, —$NR^7$Ay, —NHHet, —$NHR^{10}$Het, —$R^{10}$cycloalkyl, —$R^{10}OR^7$, —$R^{10}$OAy, —$R^{10}NR^7R^8$ and —$R^{10}NR^7$Ay;
q is 0, 1, 2, 3, 4 or 5; and
each $R^5$ is the same or different and is independently selected from the group consisting of halo, alkyl, alkenyl, alkynyl, cycloalkyl, cycloalkenyl, Ay, Het, —$OR^7$, —OAy, —OHet, —$OR^{10}$Ay, —$OR^{10}$Het, —C(O)$R^9$, —C(O)Ay, —C(O)Het, —CO$_2R^9$, —C(O)$NR^7R^8$, —C(O)$NR^7$Ay, —C(O)$NHR^{10}$Het, —C(S)$NR^9R^{11}$, —C(NH)$NR^7R^8$, —C(NH)$NR^7$Ay, —S(O)$_n$$R^9$, —S(O)$_2$$NR^7R^8$, —S(O)$_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}$C(O)$R^9$, —$R^{10}$CO$_2R^9$; —$R^{10}$C(O)$NR^9R^{11}$, —$R^{10}$C(O)$NR^7$Ay, —$R^{10}$C(O)$NHR^{10}$Het, —$R^{10}$C(S)$NR^9R^{11}$, —$R^{10}$C(NH)$NR^9R^{11}$, —$R^{10}$SO$_2R^9$, —$R^{10}$SO$_2NR^9R^{11}$, —$R^{10}$SO$_2$NHCOR$^9$, —$R^{10}NR^7R^8$, —$R^{10}NR^7$Ay, —$R^{10}$NHC(NH)$NR^9R^{11}$, cyano, nitro and azido; or
two adjacent $R^5$ groups together with the atoms to which they are bonded form a $C_{5-6}$ cycloalkyl or aryl;
wherein when Y is CH, $R^3$ is not —$NR^7$Ay;
and pharmaceutically acceptable salts, solvates and physiologically functional derivatives thereof.
In one class of compounds of formula (I), Y is CH. In another class of compounds of formula (I), Y is N.
In one particular class of compounds of formula (I), p is 0, 1, 2 or 3. In another embodiment, p is 0, 1, or 2. In one particular embodiment, p is 1 or 2. In one particular embodiment p is 1. In another particular embodiment p is 2. In one embodiment, p is 2 and optionally two adjacent $R^1$ groups together with the atoms which they are bonded, form a $C_{5-6}$ cycloalkyl or 5- or 6-membered heterocyclic group. The phrase "two adjacent $R^1$ groups" refers to two $R^1$ groups, each bonded to adjacent carbon atoms on the imidazol-pyridine ring. In the embodiment where two adjacent $R^1$ groups together with the atoms to which they are bonded form a cycloalkyl or heterocyclic group, p is typically 2, 3 or 4; more typically 2.
$R^1$ may be in the 5, 6, 7 or 8 position. In one embodiment, p is 1 and $R^1$ is in the C-8 position. In one embodiment, p is 1 and $R^1$ is in the C-6 position. In one embodiment p is 2 and one $R^1$ is in the C-8 position and one $R^1$ is in the C-6 position.
One class of compounds of formula (I) includes those compounds defined wherein at least one $R^1$ group contains an aryl, heterocyclic or heteroaryl moiety (in one embodiment, at least one $R^1$ group contains a heterocyclic or heteroaryl moiety) and two adjacent $R^1$ groups together with the atoms to which they are bonded do not form a $C_{5-6}$cycloalkyl or 5- or 6-membered heterocyclic group. Another class of compounds of formula (I) includes those compounds defined wherein p is 3 or 4, at least one $R^1$ group contains an aryl, heterocyclic or heteroaryl moiety (in one embodiment, at least one $R^1$ group contains a heterocyclic or heteroaryl moiety) and two adjacent $R^1$ groups together with the atoms to which they are bonded do form a $C_{5-6}$cycloalkyl or 5- or 6-membered heterocyclic group. Another class of compounds of formula (I) includes those compounds defined where no $R^1$ group contains an aryl, heterocyclic or heteroaryl moiety (or in one embodiment no $R^1$ group contains a heterocyclic or heteroaryl moeity) and two adjacent $R^1$ groups together with the atoms to which they are bonded do not form a $C_{5-6}$cycloalkyl or 5- or 6-membered heterocyclic group. Another class of compounds of formula (I) includes those compounds defined wherein p is 2, 3 or 4, no $R^1$ group contains an aryl, heterocyclic or heteroaryl moiety (or in one embodiment no $R^1$ group contains a heterocyclic or heteroaryl moiety) and two adjacent $R^1$ groups together with the atoms to which they are bonded do form a $C_{5-6}$cycloalkyl or 5- or 6-membered heterocyclic group.

Examples of embodiments wherein $R^1$ contains a heterocyclic or heteroaryl moiety are selected from the group consisting of Het, —OHet, —OR$^{10}$Het, —C(O)Het, —C(O)NHR$^{10}$Het, —S(O)$_n$Het, —NHHet, —NHR$^{10}$Het, —R$^{10}$Het, —R$^{10}$O—C(O)Het and —R$^{10}$C(O)NHR$^{10}$Het, or any subset thereof. Examples of embodiments wherein $R^1$ contains an aryl, heterocyclic or heteroaryl moiety are selected from the group consisting of Ay, Het, —OAy, —OR$^{10}$Ay, —OHet, —OR$^{10}$Het, —C(O)Ay, —C(O)Het, —C(O)NR$^7$Ay, —C(O)NHR$^{10}$Ay, —C(O)NHR$^{10}$Het, —C(NH)NR$^7$Ay, —S(O)$_n$Ay, —S(O)$_n$Het, —S(O)$_2$NR$^7$Ay, —NR$^7$Ay, —NHHet, —NHR$^{10}$Ay, —NHR$^{10}$Het, —R$^{10}$Ay, —R$^{10}$Het, —R$^{10}$O—C(O)Ay, —R$^{10}$O—C(O)Het, —R$^{10}$C(O)NR$^7$Ay, —R$^{10}$C(O)NHR$^{10}$Het and —R$^{10}$NR$^7$Ay, or any subset thereof. Examples of embodiments wherein no $R^1$ contains an aryl, heterocyclic or heteroaryl moiety are selected from the group consisting of halo, alkyl, alkenyl, alkynyl, cycloalkyl, cycloalkenyl, —OR$^7$, —C(O)R$^9$, —CO$_2$R$^9$, —C(O)NR$^7$R$^8$, —C(S)NR$^9$R$^{11}$, —C(NH)NR$^7$R$^8$, —S(O)$_n$R$^9$, —S(O)$_2$NR$^7$R$^8$, —NR$^7$R$^8$, —R$^{10}$cycloalkyl, —R$^{10}$O—C(O)R$^9$, —R$^{10}$O—S(O)$_n$R$^9$, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NHC(NH)NR$^9$R$^{11}$, cyano, nitro and azido, or any subset thereof.

In the embodiments where two adjacent $R^1$ groups together with the atoms to which they are bonded form a $C_{5-6}$cycloalkyl or 5- or 6-membered heterocyclic group having 1 or 2 heteroatoms, each $R^1$ group may be the same or different and may be selected from the group consisting of alkyl, alkenyl, —OR$^7$, —S(O)$_n$R$^9$ and —NR$^7$R$^8$. For example, in one embodiment two adjacent $R^1$ groups are —OR$^7$ and together with the atoms to which they are bonded, they form a heterocyclic group such as:

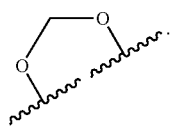

In another embodiment, two adjacent $R^1$ groups are alkyl and together with the atoms to which they are bonded, they form a cycloalkyl group such as:

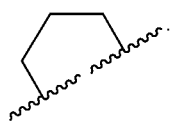

In another embodiment two adjacent $R^1$ groups are defined as —OR$^7$ and —NR$^7$R$^8$ respectively and together with the atoms to which they are bonded, they form a heterocyclic group such as:

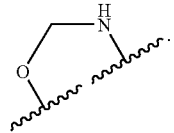

From these examples, additional embodiments can be readily ascertained by those skilled in the art.

In one embodiment, two adjacent $R^1$ groups together with the atoms to which they are bonded do not form a $C_{5-6}$cycloalkyl or a 5 or 6-membered heterocyclic ring containing 1 or 2 heteroatoms.

In one embodiment, each $R^1$ is the same or different and is independently selected from the group consisting of halo, alkyl, alkenyl, alkynyl, cycloalkyl, cycloalkenyl, Ay, Het, —OR$^7$, —OAy, —OR$^{10}$Ay —OHet, —OR$^{10}$Het, —C(O)R$^9$, —C(O)Ay, —C(O)Het, —CO$_2$R$^{10}$, —C(O)NR$^7$Ay, —C(O)NHR$^{10}$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Ay, —R$^{10}$Het, —R$^{10}$O—C(O)R$^9$, —R$^{10}$O—C(O)Ay, —R$^{10}$O—C(O)Het, —R$^{10}$O—S(O)$_n$R$^9$, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent $R^1$ groups together with the atoms to which they are bonded form a $C_{5-6}$cycloalkyl or a 5 or 6-membered heterocyclic ring containing 1 or 2 heteroatoms.

In one embodiment, each $R^1$ is the same or different and is independently selected from the group consisting of halo; alkyl, cycloalkyl, Ay, Het, —OR$^7$, —C(O)R$^9$, —C(O)Het, —CO$_2$R$^9$, —C(O)NR$^7$R$^8$, —C(O)NR$^7$Ay, —C(O)NHR$^{10}$Het, —S(O)$_n$R$^9$, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Het, —R$^{10}$OR$^9$, —R$^{10}$C(O)NR$^7$Ay, —R$^{10}$SO$_2$NHCOR$^9$, —R$^{10}$NR$^7$R$^8$, —R$^{10}$NR$^7$Ay, cyano, nitro and azido, or any subset thereof.

More particularly, each $R^1$ is the same or different and is independently selected from the group consisting of halo, alkyl, Ay, Het, —OR$^7$, —NR$^7$R$^8$, —NR$^7$Ay, —NHHet, —NHR$^{10}$Ay and —NHR$^{10}$Het.

In one particular embodiment, each $R^1$ is the same or different and is independently selected form the group consisting of halo, alkyl, Het, —NR$^7$R$^8$, —NR$^7$Ay, and —NHHet, or any subset thereof. Particularly compounds of formula (I) are defined wherein each $R^1$ is the same or different and is independently selected from the group consisting of halo, Het and —NR$^7$R$^8$, or any subset thereof.

More specific examples of embodiments of the present invention are defined wherein each $R^1$ is the same or different and is independently selected from the group consisting of halo, aryl, Het (and substituted Het), —NH$_2$, —NHalkyl, —NHcycloalkyl, —N(alkyl)(alkyl), —Nalkyl-O-alkyl, and —NHAy, or any subset thereof. Specific examples of some particular $R^1$ groups are selected from the group consisting of Br, Cl, phenyl, —NH$_2$, —NH-methyl, —NH-butyl, —N(CH$_3$)$_2$, —NH-cyclopentyl, —NH-cyclopropyl, —NH-isopropyl, —NH-phenyl, —N(CH$_2$)$_2$OCH$_3$, pyrrolidine, and morpholine, or any subset thereof.

In one embodiment, compounds of formula (I) are defined where R$^2$ contains an aryl, heterocyclic or heteroaryl moiety. In another embodiment, compounds of formula (I) are defined where R$^2$ contains a heterocyclic or heteroaryl moiety. In yet another embodiment, the compounds of formula (I) are defined where R$^2$ contains no aryl, heterocyclic or heteroaryl moiety. In another embodiment, R$^2$ contains no heteroaryl or heterocyclic moiety but may contain an aryl moeity. From the embodiments described above with respect to R$^1$, one skilled in the art can readily determine the groups defining R$^2$ which contain or exclude aryl, heterocyclic and/or heteroaryl moieties.

In one embodiment, R$^2$ is selected from the group consisting of halo, alkenyl, cycloalkyl, cycloalkenyl, Ay, Het, —OR$^7$, —OAy, —OHet, —OR$^{10}$Het, —S(O)$_n$R$^9$, —NR$^7$R$^8$, —NHHet, —NHR$^{10}$Het, —R$^{10}$NR$^7$R$^8$ and —R$^{10}$NR$^7$Ay, or any subset thereof. In particular, R$^2$ is selected from the group consisting of Het, —OR$^7$, —S(O)$_n$R$^9$, —NR$^7$R$^8$, —NHHet and —NHR$^{10}$Het, or any subset thereof. More particularly, R$^2$ is selected from the group consisting of —NR$^7$R$^8$, Het, —NHR$^{10}$Het and —NHHet, or any subset thereof. In one particular embodiment, compounds of formula (I) are defined where R$^2$ is —NR$^7$R$^8$.

More specific examples of embodiments of the present invention are defined wherein R$^2$ is selected from the group consisting of —NH$_2$, —NH-alkyl, —NH-cycloalkyl, —Het, —NHHet and —NH-alkyl-Het, or any subset thereof. Particular embodiments include those compounds of formula (I) wherein R$^2$ is —NH$_2$, —NH-propyl, —NH-isopropyl, —NH-cyclopropyl, —NH-butyl, —NH-isobutyl, —NH-cyclobutyl, —NH-cyclopentyl, —NH-cyclohexyl, —NH(CH$_2$)$_2$OCH$_3$, pyrrolidine (e.g., pyrrolidine bonded through N), and morpholine (e.g., morpholine bonded through N), or any subset thereof.

In one embodiment, R$^7$ and R$^8$ are each the same or different and are independently selected from the group consisting of H, alkyl, cycloalkyl, —C(O)R$^9$, —R$^{10}$-cycloalkyl, —R$^{10}$OR$^9$, —R$^{10}$CO$_2$R$^9$ and —R$^{10}$NR$^9$R$^{11}$, or any subset thereof. More particularly, R$^7$ and R$^8$ are each the same or different and are independently selected from the group consisting of H, alkyl, cycloalkyl, and —R$^{10}$-cycloalkyl, or any subset thereof. In one embodiment, R$^7$ and R$^8$ are each the same or different and are independently selected from the group consisting of H, alkyl and cycloalkyl.

The group —R$^{10}$(OR$^{10}$)$_w$ in the definition of R$^9$ and R$^{11}$ refers to a PEG chain. In one embodiment, R$^9$ and R$^{11}$ are each the same or different and are independently selected from the group consisting of H, alkyl, cycloalkyl, and —R$^{10}$—cycloalkyl, or any subset thereof. More particularly, R$^9$ and R$^{11}$ are each the same or different and are independently selected from the group consisting of H and alkyl.

Preferably R$^{10}$ is alkyl or cycloalkyl; more preferably alkyl.

In another embodiment, the compounds of formula (I) include those compounds defined where at least one of R$^3$ and R$^4$ contains an aryl, heterocyclic or heteroaryl moiety (or contains a heterocyclic or heteroaryl moiety but exclude aryl moeities). Another embodiment includes those compounds of formula (I) where neither R$^3$ nor R$^4$ contain an aryl, heterocyclic or heteroaryl moeity (or neither contains a heterocyclic or heteroaryl moeity but may contain an aryl moeity). Based on the guidance given above for R$^1$, one skilled in the art can readily determine the list of appropriate groups defining R$^3$ and R$^4$ which contain or exclude aryl, heterocyclic and/or heteroaryl moeities.

In one embodiment, R$^3$ is selected from the group consisting of H, halo, alkyl, Ay, —OR$^7$, —CO$_2$R$^7$, —NR$^7$R$^8$, —R$^{10}$OR$^7$ and —R$^{10}$NR$^7$R$^8$, or any subset thereof. More particularly, R$^3$ is selected from the group consisting of H, halo, alkyl, —OR$^7$, and —NR$^7$R$^8$, or any subset thereof. In one embodiment, R$^3$ is H or alkyl. In one embodiment R$^3$ is H.

In one embodiment, R$^4$ is selected from the group consisting of of H, halo, alkyl, Ay, —OR$^7$, —CO$_2$R$^7$, —NR$^7$R$^8$, —R$^{10}$OR$^7$ and —R$^{10}$NR$^7$R$^8$, or any subset thereof. More preferably, R$^4$ is selected from the group consisting of H, halo, alkyl, —OR$^7$, and —NR$^7$R$^8$, or any subset thereof. In one embodiment, R$^4$ is H or alkyl. In one embodiment R$^4$ is H.

In one embodiment, q is 0, 1 or 2. In one embodiment, q is 0. In another embodiment, q is 1. In one embodiment, q is 2 and optionally two adjacent R$^5$ groups together with the atoms which they are bonded, they form a C$_{5-6}$ cycloalkyl or aryl. The phrase "two adjacent R$^5$ groups" refers to two R$^5$ groups, each bonded to adjacent carbon atoms on the phenyl ring. In the embodiment where two adjacent R$^5$ groups together with the atoms to which they are bonded form a cycloalkyl or aryl, q is typically 2, 3, 4 or 5; more typically 2.

R$^5$ may be in the ortho, meta or para position.

Another class of compounds of formula (I) includes those compounds defined wherein at least one R$^5$ group contains an aryl, heterocyclic or heteroaryl moiety (or in one embodiment a heterocyclic or heteroaryl moiety) and two adjacent R$^5$ groups together with the atoms to which they are bonded do not form a C$_{5-6}$ cycloalkyl or aryl. Another class of compounds of formula (I) includes those compounds defined wherein q is 3, 4 or 5, at least one R$^5$ group contains an aryl, heterocyclic or heteroaryl moiety (or in one embodiment, a heterocyclic or heteroaryl moiety) and two adjacent R$^5$ groups together with the atoms to which they are bonded do form a C$_{5-6}$ cycloalkyl or aryl. Another class of compounds of formula (I) includes those compounds defined where no R$^5$ group contains an aryl, heterocyclic or heteroaryl moiety (or in one embodiment no R$^5$ group contains a heterocyclic or heteroaryl moiety) and two adjacent R$^5$ groups together with the atoms to which they are bonded do not form a C$_{5-6}$ cycloalkyl or aryl. Another class of compounds of formula (I) includes those compounds defined wherein q is 2, 3, 4 or 5, no R$^5$ group contains an aryl, heterocyclic or heteroaryl moiety (or in one embodiment no R$^5$ group contains a heterocyclic or heteroaryl moiety) and two adjacent R$^5$ groups together with the atoms to which they are bonded do not form a C$_{5-6}$ cycloalkyl or aryl.

When two adjacent R$^5$ groups together with the atoms to which they are bonded do form a cycloalkyl or aryl, each R$^5$ group may be the same or different and is typically selected from the group consisting of alkyl and alkenyl. A specific example of a cycloalkyl formed from two adjacent R$^5$ groups together with the atoms to which they are bonded is described above in connection with the description of two adjacent R$^1$ groups forming similar rings. Based on the guidance given above, examples of aryl rings formed from two adjacent R$^5$ groups together with the atoms to which they are bonded can be readily determined by those skilled in the art. In one preferred embodiment, two adjacent R$^5$ groups together with the atoms to which they are bonded do not form a C$_{5-6}$ cycloalkyl or aryl.

In one embodiment, each R$^5$ group is the same or different and is independently selected from the group consisting of halo, alkyl, alkenyl, Ay, Het, —OR⁷, —OAy, —CO₂R⁹, —C(O)NR⁷R⁸, —C(O)NR⁷Ay, —S(O)₂NR⁷R⁸, —NR⁷R⁸, —NR⁷Ay, —NHR¹⁰Ay, cyano, nitro and azido, or any subset thereof. More particularly, each R⁵ group is the same or different and is independently selected from the group consisting of halo, alkyl, Het, —OR⁷, —C(O)NR⁷R⁸, —S(O)₂NR⁷R⁸, —NR⁷R⁸, cyano, nitro and azido, or any subset thereof. In one embodiment, each R⁵ group is the same or different and is independently selected from the group consisting of halo, alkyl, —OR⁷, —NR⁷R⁸ and cyano, or any subset thereof.

More specific examples of compounds of formula (I) are defined wherein each R⁵ is the same or different and is each independently selected from the group consisting of halo (e.g., fluoro, chloro or bromo), alkyl (e.g., methyl and trifluoromethyl), O-alkyl (e.g., O-methyl, O-isobutyl, and

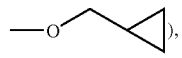

O-allyl, cyano, —NH—CH₃, and —N(CH₃)₂, or any subset thereof.

It is to be understood that the present invention includes all combinations and subsets of the particular and preferred groups defined hereinabove.

Specific examples of compounds of formula (I) include but are not limited to:
3-[2-(Cyclopentylamino)-4-pyrimidinyl]-2-(4-fluorophenyl)imidazo[1,2-α]pyridin-8-amine;
4-[8-Chloro-2-(4-fluorophenyl)imidazo[1,2-α]pyridin-3-yl]-N-cyclopentyl-2-pyrimidinamine;
N-Cyclopentyl-3-[2-(cyclopentylamino)-4-pyrimidinyl]-2-(4-fluorophenyl)imidazo[1,2-α]pyridin-8-amine;
N-Cyclopentyl-4-[2-(4-fluorophenyl)-8-(1-pyrrolidinyl)imidazo[1,2-α]pyridin-3-yl]-2-pyrimidinamine;
N-Butyl-3-[2-(cyclopentylamino)-4-pyrimidinyl]-2-(4-fluorophenyl)imidazo[1,2-α]pyridin-8-amine;
3-[2-(Cyclopentylamino)-4-pyrimidinyl]-2-(4-fluorophenyl)-N-(2-methoxyethyl)imidazo[1,2-α]pyridin-8-amine;
4-[8-Chloro-2-(4-fluorophenyl)imidazo[1,2-α]pyridin-3-yl]-N-methyl-2-pyrimidinamine;
N-Cyclopentyl-2-(4-fluorophenyl)-3-[2-(methylamino)-4-pyrimidinyl]imidazo[1,2-α]pyridin-8-amine;
4-[8-Chloro-2-(4-methoxyphenyl)imidazo[1,2-α]pyridin-3-yl]-N-cyclopentyl-2-pyrimidinamine;
N-Cyclopentyl-3-[2-(cyclopentylamino)-4-pyrimidinyl]-2-(4-methoxyphenyl)imidazo[1,2-α]pyridin-8-amine;
4-{8-(Cyclopentylamino)-3-[2-(cyclopentylamino)-4-pyrimidinyl]imidazo[1,2-α]pyridin-2-yl}phenol;
8-chloro-2-(4-fluorophenyl)-3-(2-fluoro-4-pyridinyl)imidazo[1,2-α]pyridine;
4-[8-Chloro-2-(4-fluorophenyl)imidazo[1,2-α]pyridin-3-yl]-N-cyclopentyl-2-pyridinamine;
N-Cyclopentyl-3-[2-(cyclopentylamino)-4-pyridinyl]-2-(4-fluorophenyl)imidazo[1,2-α]pyridin-8-amine;
4-[8-Chloro-2-(3-methoxyphenyl)imidazo[1,2-α]pyridin-3-yl]-N-cyclopentyl-2-pyrimidinamine;
N-Cyclopentyl-3-[2-(cyclopentylamino)-4-pyrimidinyl]-2-(3-methoxyphenyl)imidazo[1,2-α]pyridin-8-amine;
3-{8-(Cyclopentylamino)-3-[2-(cyclopentylamino)-pyrimidinyl]imidazo[1,2-α]pyridin-2-yl}phenol;
2-[3-(Allyloxy)phenyl]-N-cyclopentyl-3-[2-(cyclopentylamino)-4-pyrimidinyl]imidazo[1,2-α]pyridin-8-amine;
4-[8-Chloro-2-(4-methylphenyl)imidazo[1,2-α]pyridin-3-yl]-N-cyclopentyl-2-pyrimidinamine;
N-Cyclopentyl-3-[2-(cyclopentylamino)-4-pyrimidinyl]-2-(4-methylphenyl)imidazo[1,2-α]pyridin-8-amine;
3-[2-(Cyclopentylamino)-4-pyrimidinyl]-N-(2-methoxyethyl)-2-(4-methylphenyl)imidazo[1,2-α]pyridin-8-amine;
N-Cyclopentyl-4-[2-(4-methylphenyl)-8-(4-morpholinyl)imidazo[1,2α]pyridin-3-yl]-2-pyrimidinamine;
4-[8-Chloro-2-(2-naphthyl)imidazo[1,2α]pyridin-3-yl]-N-cyclopropyl-2-pyrimidinamine;
N-Cyclopropyl-3-[2-(cyclopropylamino)-4-pyrimidinyl]-2-(2-naphthyl)imidazo[1,2α]pyridin-8-amine;
4-{8-Chloro-3-[2-(cyclopentylamino)-4-pyrimidinyl]imidazo[1,2α]pyridin-2-yl}benzonitrile;
4-{8-(Cyclopentylamino)-3-[2-(cyclopentylamino)-4-pyrimidinyl]imidazo[1,2α]pyridin-2-yl}benzonitrile;
4-[3-[2-(Cyclopentylamino)-4-pyrimidinyl]-8-(4-morpholinyl)imidazo[1,2α]pyridin-2-yl]benzonitrile;
4-[3-[2-(Cyclopentylamino)-4-pyrimidinyl]-8-(4-morpholinyl)imidazo[1,2α]pyridin-2-yl]benzamide;
4-{8-(Cyclopentylamino)-3-[2-(cyclopentylamino)-4-pyrimidinyl]imidazo[1,2α]pyridin-2-yl}benzamide;
N-{4-[8-Chloro-2-(3-nitrophenyl)imidazo[1,2α]pyridin-3-yl]-2-pyrimidinyl}-N-cyclopentylamine;
N-Cyclopentyl-4-[8-(4-morpholinyl)-2-(3-nitrophenyl)imidazo[1,2α]pyridin-3-yl]-2-pyrimidinamine;
4-[2-(3-Aminophenyl)-8-chloroimidazo[1,2α]pyridin-3-yl]-N-cyclopentyl-2-pyrimidinamine;
2-(3-Aminophenyl)-N-cyclopentyl-3-[2-(cyclopentylamino)-4-pyrimidinyl]imidazo[1,2α]pyridin-8-amine;
N-Cyclopentyl-3-[2-(cyclopentylamino)-4-pyrimidinyl]-2-{3-[(cyclopropylmethyl)amino]phenyl}imidazo[1,2α]pyridin-8-amine;
2-{3-[Bis(cyclopropylmethyl)amino]phenyl}-N-cyclopentyl-3-[2-(cyclopentylamino)-4-pyrimidinyl]imidazo[1,2α]pyridin-8-amine;
3-{8-Chloro-3-[2-(cyclopentylamino)-4-pyrimidinyl]imidazo[1,2α]pyridin-2-yl}benzonitrile;
3-{8-(Cyclopentylamino)-3-[2-(cyclopentylamino)-4-pyrimidinyl]imidazo[1,2α]pyridin-2-yl}benzonitrile;
N-Cyclopentyl-4-[6,8-dichloro-2-(4-fluorophenyl)imidazo[1,2α]pyridin-3-yl]-2-pyrimidinamine;
N-{4-[6-Chloro-8-(cyclopentylamino)-2-(4-fluorophenyl)imidazo[1,2α]pyridin-3-yl]-2-pyrimidinyl}-N-cyclopentylamine;
N-Cyclopentyl-4-[6,8-dibromo-2-(4-fluorophenyl)imidazo[1,2α]pyridin-3-yl]-2-pyrimidinamine;
N-{4-[6-Bromo-8-(cyclopentylamino)-2-(4-fluorophenyl)imidazo[1,2α]pyridin-3-yl]-2-pyrimidinyl}-N-cyclopentylamine;
6-Bromo-N-butyl-3-[2-(cyclopentylamino)-4-pyrimidinyl]-2-(4-fluorophenyl)imidazo[1,2α]pyridin-8-amine;
N-Cyclopentyl-4-[2-(4-fluorophenyl)-6,8-di(4-morpholinyl)imidazo[1,2α]pyridin-3-yl]-2-pyrimidinamine;
N-{4-[6-Bromo-2-(4-fluorophenyl)-8-methylimidazo[1,2α]pyridin-3-yl]-2-pyrimidinyl}-N-cyclopentylamine;
N-Cyclopentyl-3-[2-(cyclopentylamino)-4-pyrimidinyl]-2-(4-fluorophenyl)-8-methylimidazo[1,2α]pyridin-6-amine;
N-Cyclopentyl-4-[2-(4-fluorophenyl)-8-methylimidazo[1,2-α]pyridin-3-yl]-2-pyrimidinamine;
N-{4-[6-Bromo-2-(4-fluorophenyl)imidazo[1,2α]pyridin-3-yl]-2-pyrimidinyl}-N-cyclopentylamine;
N-Cyclopentyl-3-[2-(cyclopentylamino)-4-pyrimidinyl]-2-(4-fluorophenyl)imidazo[1,2α]pyridin-6-amine;
N-Cyclopentyl-4-[2-(4-fluorophenyl)imidazo[1,2α]pyridin-3-yl]-2-pyrimidinamine;

N-Cyclopentyl-4-[2-(4-fluorophenyl)-6-(4-morpholinyl)imidazo[1,2α]pyridin-3-yl]-2-pyrimidinamine;

3-[2-(cyclopentylamino)-4-pyrimidinyl]-N-cyclopropyl-2-(4-fluorophenyl)imidazo[1,2α]pyridin-8-amine;

2-[4-(Allyloxy)phenyl]-N-cyclopentyl-3-[2-(cyclopentylamino)-4-pyrimidinyl]imidazo[1,2α]pyridin-8-amine;

N-Cyclopentyl-3-[2-(cyclopentylamino)-4-pyrimidinyl]-2-[4-(cyclopropylmethoxy)phenyl]imidazo[1,2α]pyridin-8-amine;

N-Cyclopentyl-3-[2-(cyclopentylamino)-4-pyrimidinyl]-2-(4-fluorophenyl)-6-(trifluoromethyl)imidazo[1,2α]pyridin-8-amine;

3-{8-(Cyclopentylamino)-3-[2-(cyclopentylamino)pyrimidin-4-yl]imidazo[1,2α]pyridin-2-yl}benzoic acid;

2-(3-Azidophenyl)-N-butyl-3-[2-(cyclopentylamino)pyrimidin-4-yl]imidazo[1,2α]pyridin-8-amine;

4-[8-(Benzyloxy)-2-(4-fluorophenyl)imidazo[1,2α]pyridin-3-yl]-N-cyclopentylpyrimidin-2-amine; and 3-[2-(Cyclopentylamino)pyrimidin-4-yl]-2-(4-fluorophenyl)imidazo[1,2α]pyridin-8-ol, and pharmaceutically acceptable salts, solvates and physiologically functional derivatives thereof.

In particular, some compounds of formula (I) include but are not limited to:

3-[2-(Cyclopentylamino)-4-pyrimidinyl]-2-(4-fluorophenyl)imidazo[1,2α]pyridin-8-amine;

N-Cyclopentyl-3-[2-(cyclopentylamino)-4-pyrimidinyl]-2-(4-fluorophenyl)imidazo[1,2α]pyridin-8-amine;

N-Butyl-3-[2-(cyclopentylamino)-4-pyrimidinyl]-2-(4-fluorophenyl)imidazo[1,2α]pyridin-8-amine;

3-[2-(Cyclopentylamino)-4-pyrimidinyl]-2-(4-fluorophenyl)-N-(2-methoxyethyl)imidazo[1,2α]pyridin-8-amine;

N-Cyclopentyl-3-[2-(cyclopentylamino)-4-pyrimidinyl]-2-(4-methoxyphenyl)imidazo[1,2α]pyridin-8-amine;

N-Cyclopentyl-3-[2-(cyclopentylamino)-4-pyrimidinyl]-2-(3-methoxyphenyl)imidazo[1,2α]pyridin-8-amine;

2-[3-(Allyloxy)phenyl]-N-cyclopentyl-3-[2-(cyclopentylamino)-4-pyrimidinyl]imidazo[1,2-α]pyridin-8-amine;

N-Cyclopentyl-3-[2-(cyclopentylamino)-4-pyrimidinyl]-2-(4-methylphenyl)imidazo[1,2-α]pyridin-8-amine;

3-[2-(Cyclopentylamino)-4-pyrimidinyl]-N-(2-methoxyethyl)-2-(4-methylphenyl)imidazo[1,2-α]pyridin-8-amine;

N-Cyclopentyl-4-[2-(4-methylphenyl)-8-(4-morpholinyl)imidazo[1,2-α]pyridin-3-yl]-2-pyrimidinamine;

4-[8-Chloro-2-(2-naphthyl)imidazo[1,2-α]pyridin-3-yl]-N-cyclopropyl-2-pyrimidinamine;

N-Cyclopropyl-3-[2-(cyclopropylamino)-4-pyrimidinyl]-2-(2-naphthyl)imidazo[1,2-a]pyridin-8-amine;

4-{8-Chloro-3-[2-(cyclopentylamino)-4-pyrimidinyl]imidazo[1,2-α]pyridin-2-yl}benzonitrile;

4-{8-(Cyclopentylamino)-3-[2-(cyclopentylamino)-4-pyrimidinyl]imidazo[1,2-a]pyridin-2-yl}benzonitrile;

4-[3-[2-(Cyclopentylamino)-4-pyrimidinyl]-8-(4-morpholinyl)-imidazo[1,2-α]pyridin-2-yl]benzonitrile;

3-{8-Chloro-3-[2-(cyclopentylamino)-4-pyrimidinyl]imidazo[1,2-α]pyridin-2-yl}benzonitrile;

N-Cyclopentyl-4-[6,8-dichloro-2-(4-fluorophenyl)imidazo[1,2-α]pyridin-3-yl]-2-pyrimidinamine;

N-{4-[6-Chloro-8-(cyclopentylamino)-2-(4-fluorophenyl)imidazo[1,2-α]pyridin-3-yl]-2-pyrimidinyl}-N-cyclopentylamine;

N-Cyclopentyl-4-[6,8-dibromo-2-(4-fluorophenyl)imidazo[1,2-α]pyridin-3-yl]-2-pyrimidinamine;

N-{4-[6-Bromo-8-(cyclopentylamino)-2-(4-fluorophenyl)imidazo[1,2-α]pyridin-3-yl]-2-pyrimidinyl}-N-cyclopentylamine;

6-Bromo-N-butyl-3-[2-(cyclopentylamino)-4-pyrimidinyl]-2-(4-fluorophenyl)imidazo[1,2-α]pyridin-8-amine;

N-Cyclopentyl-4-[2-(4-fluorophenyl)-6,8-di(4-morpholinyl)imidazo[1,2-α]pyridin-3-yl]-2-pyrimidinamine;

N-Cyclopentyl-3-[2-(cyclopentylamino)-4-pyrimidinyl]-2-(4-fluorophenyl)-8-methylimidazo[1,2-α]pyridin-6-amine;

N-Cyclopentyl-4-[2-(4-fluorophenyl)-6-(4-morpholinyl)imidazo[1,2-α]pyridin-3-yl]-2-pyrimidinamine;

3-[2-(cyclopentylamino)-4-pyrimidinyl]-N-cyclopropyl-2-(4-fluorophenyl)imidazo[1,2-α]pyridin-8-amine;

2-[4-(Allyloxy)phenyl]-N-cyclopentyl-3-[2-(cyclopentylamino)-4-pyrimidinyl]imidazo[1,2-α]pyridin-8-amine;

N-Cyclopentyl-3-[2-(cyclopentylamino)-4-pyrimidinyl]-2-[4-(cyclopropylmethoxy)phenyl]imidazo[1,2-a]pyridin-8-amine;

N-Cyclopentyl-3-[2-(cyclopentylamino)-4-pyrimidinyl]-2-(4-fluorophenyl)-6-(trifluoromethyl)imidazo[1,2-α]pyridin-8-amine;

4-[8-(Benzyloxy)-2-(4-fluorophenyl)imidazo[1,2-α]pyridin-3-yl]-N-cyclopentylpyrimidin-2-amine; and 3-[2-(Cyclopentylamino)pyrimidin-4-yl]-2-(4-fluorophenyl)imidazo[1,2-α]pyridin-8-ol, and pharmaceutically acceptable salts, solvates and physiologically functional derivatives thereof.

It will be appreciated by those skilled in the art that the compounds of the present invention may also be utilized in the form of a pharmaceutically acceptable salt solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. In one embodiment, the compounds of formula (I) are in the form of the mesylate salt. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the processes for preparing pharmaceutically acceptable salts, solvates and physiologically functional derivatives of the compounds of formula (I).

Certain compounds of formula (I) and intermediates used in the processes of preparing compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from restenosis following angioplasty (RFA), viral infection, particularly by CMV and/or HHV-6 plays a pivotal role in the proliferation of the smooth muscle cells in the coronary vessel. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of conditions or diseases associated with hepatitis B or hepatitis C viruses, human papilloma virus (HPV) and HIV.

The present invention also provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the complete prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject.

As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the compound of formula (I) in the preparation of a medicament for the treatment of conditions or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is preferable to present the active ingredient as a pharmaceutical composition. The pharmaceutical composition may comprise a pharmaceutically acceptable carrier or diluent. The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I) with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules (including soft-gel capsules), cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Liquid preparations may also be formulated as soft-gel capsules for oral administration, e.g., containing conventional soft-gel excipients such as polyethylene glycol.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations suitable for topical (e.g., dermal) or intra-nasal application include ointments, creams, lotions, pastes, gels, sprays, aerosols and oils. Suitable carriers for such formulations include petroleum jelly, lanolin, polyethyleneglycols, alcohols, and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, famcyclovir, ganciclovir, docosanol, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir or valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art Compounds of formula (I) wherein Y is N; $R^2$ is selected from the group consisting of alkenyl, cycloalkyl, cycloalkenyl, Ay, Het, $-OR^7$, $-OAy$, $-OHet$, $-OR^{10}Het$, $-S(O)_nR^9$, $-S(O)_nAy$, $-S(O)_nNR^7R^8$, $-S(O)_nHet$, $-NR^7R^8$, $-NHHet$, $-NHR^{10}Ay$, $-NHR^{10}Het$, $-R^{10}NR^7R^8$ and $-R^{10}NR^7Ay$; and $R^3$ and $R^4$ are both H, may be conveniently prepared by a process outlined in Scheme 1 below.

Scheme 1

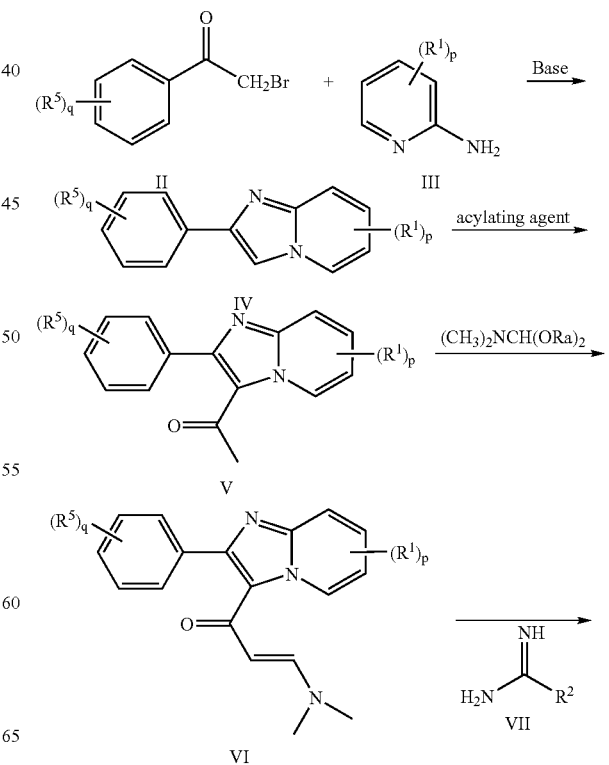

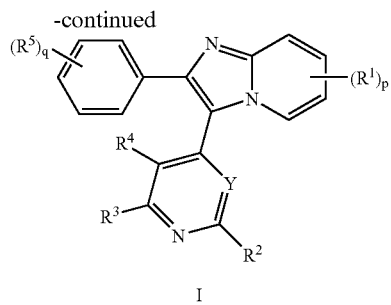

I wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Ay, —$C(O)NHR^{10}$Het, —$C(S)NR^9R^{11}$, —$C(NH)NR^7R^8$, —$C(NH)NR^7$Ay, —$S(O)_nR^9$, —$S(O)_n$Ay, —$S(O)_n$Het, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—$C(O)R^9$, —$R^{10}$O—C(O)Ay, —$R^{10}$O—C(O)Het, —$R^{10}$O—$S(O)_nR^9$, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^1$ groups together with the atoms to which they are bonded form a $C_{5-6}$cycloalkyl or a 5 or 6-membered heterocyclic ring containing 1 or 2 heteroatoms;

each $R^7$ and $R^8$ are the same or different and are independently selected from the group consisting of H, alkyl, cycloalkyl, alkenyl, cycloalkenyl, —$OR^9$, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}OR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$;

each $R^9$ and $R^{11}$ are the same or different and are independently selected from the group consisting of H, alkyl, cycloalkyl, —$R^{10}$cycloalkyl, —$R^{10}$OH, —$R_{10}(OR^{10})_w$ where w is 1–10, and —$R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

$R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_nNR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay;

n is 0, 1 or 2;

Y is N;

$R^3$ and $R^4$ are both H;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, —$OR^7$, —OAy, —OHet, —$OR^{10}$Ay, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Het, —$C(S)NR^9R^{11}$, —$C(NH)NR^7R^8$, —$C(NH)NR^7$Ay, —$S(O)_nR^9$, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^5$ groups together with the atoms to which they are bonded form a $C_{5-6}$ cycloalkyl or aryl; and Ra is alkyl or cycloalkyl.

Generally, the process for preparing the compounds of formula (I) wherein Y is N; $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_nNR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay; and $R^3$ and $R^4$ are both H, (all formulas and all other variables having been defined above in connection with Scheme 1) comprises the steps of:

(a) reacting an aminopyridine of formula (III) with a 2-bromoacetophenone of formula (II) to prepare a compound of formula (IV);

(b) acylating the compound of formula (IV) to prepare a compound of formula (V);

(c) reacting the compound of formula (V) with a dimethylformamide dialkyl acetal of formula $(CH_3)_2NCH(ORa)_2$ to prepare a compound of formula (VI); and (d) reacting the compound of formula (VI) with a compound of formula (VII) to prepare a compound of formula (I).

More specifically, compounds of formula (I) wherein Y is N; $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_nNR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay; and $R^3$ and $R^4$ are both H, can be prepared by reacting a compound of formula (VI) with a compound of formula (VII).

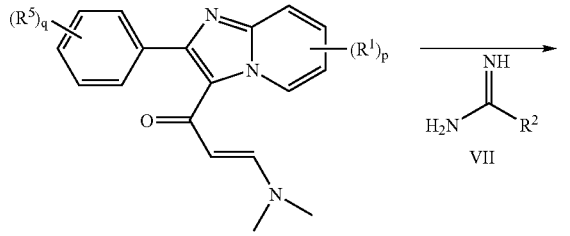

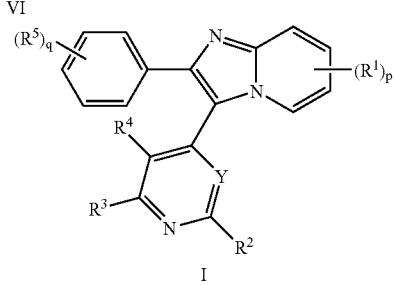

I wherein all variables are as defined above in connection with Scheme 1.

This method can be readily carried out by mixing a compound of formula (VI) with a compound of formula (VII) in a suitable solvent, optionally in the presence of a base (preferably when the amidine is in a salt form), and heating the reaction at 20–150° C. Typical solvents include lower alcohols such as methanol, ethanol, isopropanol, dimethylformamide, 1-methyl-2-pyrrolidinone, and the like. The base is typically a sodium alkoxide, potassium carbonate, or an amine base such as triethylamine. In one embodiment, the solvent is ethanol and the base is potassium carbonate, or an amine base such as triethylamine.

Compounds of the formula (VI) may be conveniently prepared by reacting a compound of formula (V) with a dimethylformamide dialkyl acetal.

Typically the acylation is carried out by treating the compounds of formula (IV) with an acylating agent, optionally in the presence of an acid or Lewis acid catalyst optionally in an inert solvent with optional heating. Typical acylating agents will be readily determined by those skilled in the art. One preferred acylating agent is acetic anhydride. Acid catalysts are also known to those skilled in the art. One preferred acid catalyst for use in this reaction is sulfuric acid. The reaction can also be carried out using N,N-dimethylacetamide and phosphorous oxychloride, optionally in an inert solvent with optional heating.

Compounds of formula (IV) are conveniently prepared by condensation of aminopyridines of formula (III) with 2-bromoacetophenones of formula (II) optionally in the presence of base.

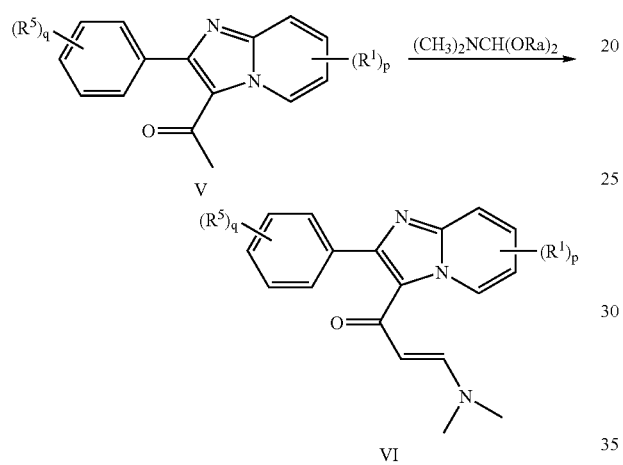

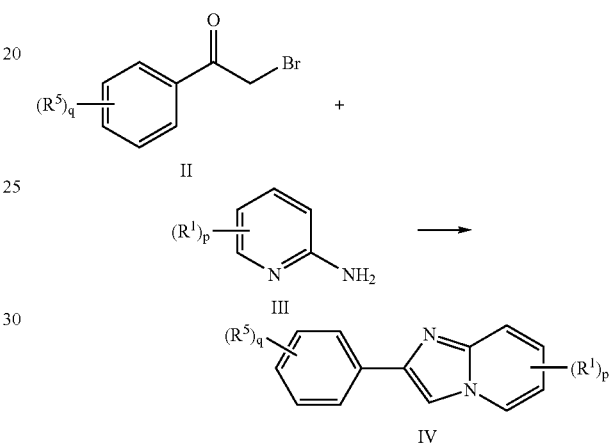

wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (V) with the dimethylformamide dialkyl acetal, optionally with heating and optionally in the presence of solvent such as N,N-dimethylformamide.

Compounds of the formula (V) may be conveniently prepared from compounds of the formula (IV) using an acylation procedure.

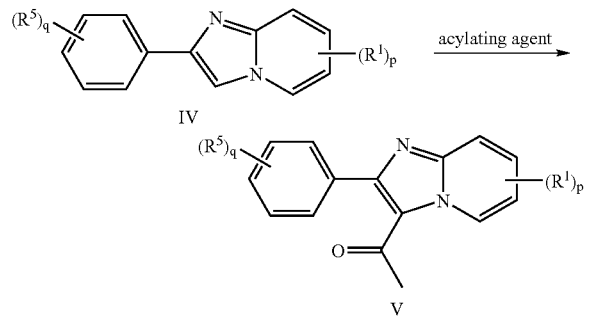

wherein all variables are as defined above in connection with Scheme 1.

wherein all variables are as defined above in connection with Scheme 1.

The condensation of the aminopyridine of formula (III) with the 2-bromoacetophenone of formula (II) can be accomplished in a suitable solvent at a temperature of about 20–200° C., optionally in the presence of base. Suitable inert solvents include, but are not limited to, ethanol, isopropanol and N,N-dimethylformamide and the like. Suitable bases include sodium bicarbonate, sodium carbonate, potassium carbonate, sodium hydroxide and the like.

Compounds of formula (II) and (III) are commercially available or may be prepared using methods known to those skilled in the art.

In addition to the foregoing process for preparing certain compounds of formula (I), the present invention also provides certain intermediate compounds for use in the preparation of such compounds of formula (I) according to the foregoing process. Such intermediates are described in Scheme 1 above.

In a further embodiment of the present invention, compounds of formula (I) wherein Y is N; $R^2$ is selected from the group consisting of alkenyl, cycloalkyl, cycloalkenyl, Ay, Het, —$OR^7$, —OAy, —OHet, —$OR^{10}$Het, —S(O)$_n$$R^9$, —S(O)Ay, —S(O)$_n$$NR^7R^8$, —S(O)$_n$Het, —$NR^7R^8$, —NH-Het, —$NHR^{10}$Ay, —$NHR^{10}$Het, —$R^{10}NR^7R^8$ and —$R^{10}NR^7$Ay; $R^3$ is selected from the group consisting of H, alkyl, alkenyl, cycloalkyl, Ay, Het, —C(O)$R^7$, —$CO_2R^7$, —$SO_2NHR^9$, —$NR^7R^8$ (where $R^7$ and $R^8$ are not H), —$R^{10}OR^7$ and —$R^{10}NR^7R^8$; and $R^4$ is H, may be conveniently prepared by a process outlined in Scheme 2 below.

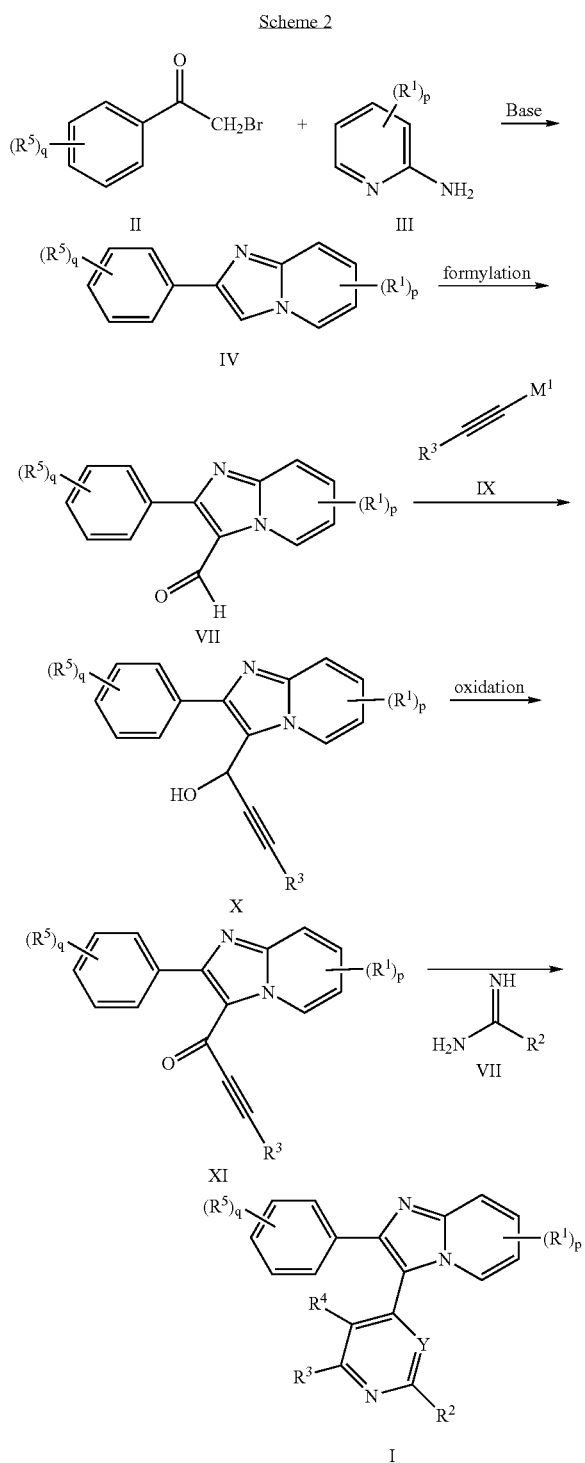

—C(NH)NR⁷R⁸, —C(NH)NR⁷Ay, —S(O)ₙR⁹, —S(O)ₙAy, —S(O)ₙHet, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Ay, —R¹⁰Het, —R¹⁰O—C(O)R⁹, —R¹⁰O—C(O)Ay, —R¹⁰O—C(O)Het, —R¹⁰O—S(O)ₙR⁹, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R¹ groups together with the atoms to which they are bonded form a C₅₋₆cycloalkyl or a 5 or 6-membered heterocyclic ring containing 1 or 2 heteroatoms;

each R⁷ and R⁸ are the same or different and are independently selected from the group consisting of H, alkyl, cycloalkyl, alkenyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R¹⁰, —R¹⁰SO₂NR⁹R¹¹, —R¹⁰SO₂NHCOR⁹, —R¹⁰NR⁹R¹¹, —R¹⁰NHCOR⁹, —R¹⁰NHSO₂R⁹ and —R¹⁰NHC(NH)NR⁹R¹¹;

each R⁹ and R¹¹ are the same or different and are independently selected from the group consisting of H, alkyl, cycloalkyl, —R¹⁰cycloalkyl, —R¹⁰OH, —R₁₀(OR¹⁰)_w where w is 1-10, and —R¹⁰NR¹⁰R¹⁰;

each R¹⁰ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

R² is selected from the group consisting of alkenyl, cycloalkyl, cycloalkenyl, Ay, Het, —OR⁷, —OAy, —OHet, —OR¹⁰Het, —S(O)ₙR⁹, —S(O)ₙAy, —S(O)ₙNR⁷R⁸, —S(O)ₙHet, —NR⁷R⁸, —NHHet, —NHR¹⁰Ay, —NHR¹⁰Het, —R¹⁰NR⁷R⁸ and —R¹⁰NR⁷Ay;

n is 0, 1 or 2;

Y is N;

R³ is selected from the group consisting of H, alkyl, alkenyl, cycloalkyl, Ay, Het, —C(O)R⁷, —CO₂R⁷, —SO₂NHR⁹, —NR⁷R⁸ (where R⁷ and R⁸ are not H), —R¹⁰OR⁷ and —R¹⁰NR⁷R⁸;

R⁴ is H;

q is 0, 1, 2, 3, 4 or 5;

each R⁵ is the same or different and is independently selected from the group consisting of halo, alkyl, alkenyl, alkynyl, cycloalkyl, cycloalkenyl, Ay, Het, —OR⁷, —OAy, —OHet, —OR¹⁰Ay, —OR¹⁰Het, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)ₙR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R⁵ groups together with the atoms to which they are bonded form a C₅₋₆ cycloalkyl or aryl; and M¹ is Li, Mg-halide or cerium-halide, wherein halide is halo.

Generally, the process for preparing compounds of formula (I) wherein Y is N; $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n NR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay; $R^3$ is selected from the group consisting of H, alkyl, alkenyl, cycloalkyl, Ay, Het, —$C(O)R^7$, —$CO_2R^7$, —$SO_2NHR^9$, —$NR^7R^8$ (where $R^7$ and $R^8$ are not H), —$R^{10}OR^7$ and —$R^{10}NR^7R^8$; and $R^4$ is H (all other variables having been defined above in connection with Scheme 2), comprises the following steps:

(a) reacting an aminopyridine of formula (III) with a 2-bromoacetophenone of formula (II) to prepare a compound of formula (IV);
(b) formylating the compound of formula (IV) to prepare a compound of formula (VIII);
(c) reacting the compound of formula (VIII) with a compound of formula (IX) to prepare a compound of formula (X);
(d) oxidizing the compound of formula (X) to prepare a compound of formula (XI); and
(e) reacting a compound of formula (XI) with a compound of formula (VII) to prepare a compound of formula (I).

More specifically, compounds of formula (I) wherein Y is N; $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n NR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay; $R^3$ is selected from the group consisting of H, alkyl, alkenyl, cycloalkyl, Ay, Het, —$C(O)R^7$, —$CO_2R^7$, —$SO_2NHR^9$, —$NR^7R^8$ (where $R^7$ and $R^8$ are not H), —$R^{10}OR^7$ and —$R^{10}NR^7R^8$; and $R^4$ is H, may be prepared by reacting a compound of formula (XI) with a compound of formula (VII).

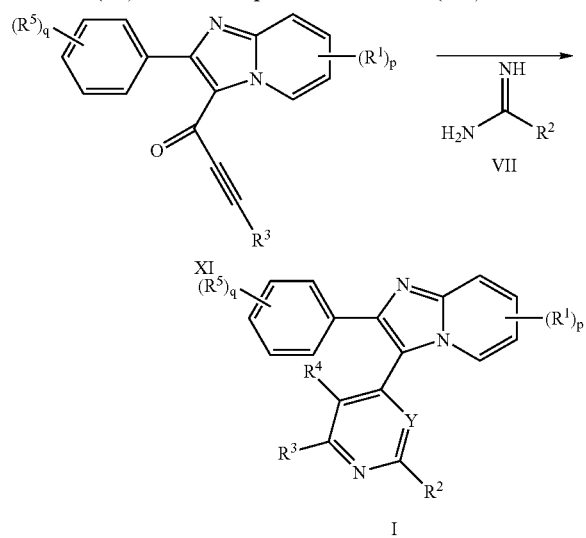

wherein all variables are as defined above in connection with Scheme 2.

This method can be readily carried out by mixing a compound of formula (XI) with a compound of formula (VII) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide, 1-methyl-2-pyrrolidinone and the like and the base is potassium carbonate, or an amine base such as triethylamine.

Compounds of formula (XI) may be conveniently prepared by oxidation of a compound of formula (X).

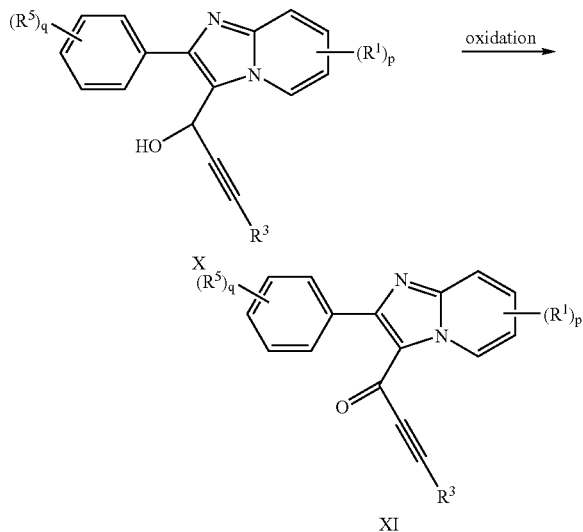

wherein all variables are as defined above in connection with Scheme 2.

Preferred oxidizing agents include but are not limited to, manganese dioxide, and the like, in an inert solvent. Suitable inert solvents include but are not limited to, dichloromethane, chloroform, N,N-dimethylformamide, ether, and the like. In another embodiment compound of formula (X) is oxidized using oxidation methods well known to those skilled in the art of organic chemistry such as Swern oxidation (Omura, K.; Swern, D. *Tetrahedron*, 1978, 34, 1651) or Dess Martin periodinane oxidation (Dess, D. B.; Martin, J. C. *J. Org. Chem.*, 1983, 48, 4155).

Compounds of formula (X) may be conveniently prepared by reacting a compound of formula (VIII) with a compound of formula (IX).

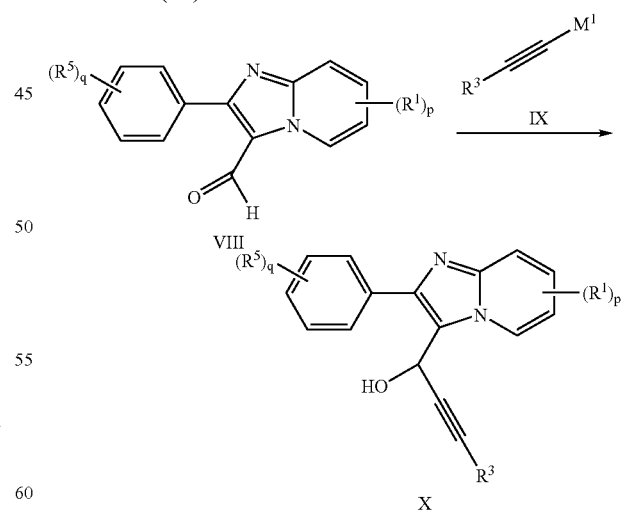

wherein all variables are as defined above in connection with Scheme 2.

Preferred metals ($M^1$) in the compounds of formula (IX) include but are not limited to, lithium, magnesium(II) halides, cerium(II) halides, and the like. Compounds of formula (IX) may be purchased from commercial sources or prepared by methods known to one skilled in the art.

Compounds of the formula (VIII) may be conveniently prepared from compounds of the formula (IV) by a formulation procedure.

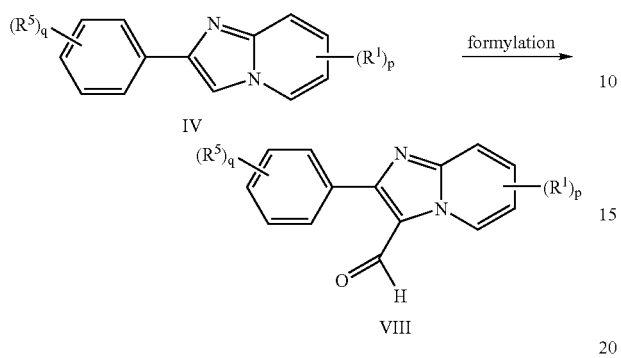

wherein all variables are as defined above in connection with Scheme 2.

Typically the formulation is carried out via the Vilsmeier-Haack reaction. The Vilsmeier-Haack reagents can be purchased from commercial sources or prepared in situ. Preferable conditions include, but are not limited to treating compounds of formula (IV) with a premixed solution of phosphorous oxychloride in N,N-dimethylformamide optionally with heating the reaction to 50–150° C.

The compounds of formula (IV) are prepared according to the process described in connection with Scheme 1 above.

In addition to the foregoing process for preparing certain compounds of formula (I), the present invention also provides certain intermediate compounds for use in the preparation of such compounds of formula (I) according to the foregoing process. Such intermediates are described in Scheme 2 above.

Further, compounds of formula (I) wherein Y is N and $R^2$ is selected from the group consisting of alkenyl, cycloalkyl, cycloalkenyl, Ay, Het, —$OR^7$, —OAy, —OHet, —$OR^{10}$Het, —$S(O)_nR^{10}$, —$S(O)_n$Ay, —$S(O)_nNR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay, may be conveniently prepared by a process outlined in Scheme 3 below.

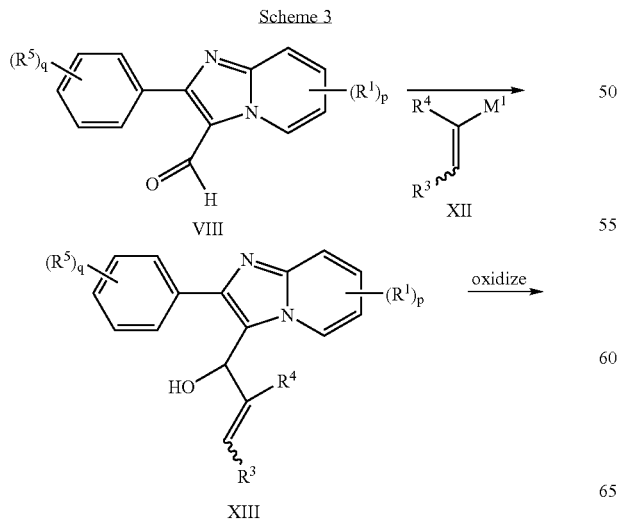

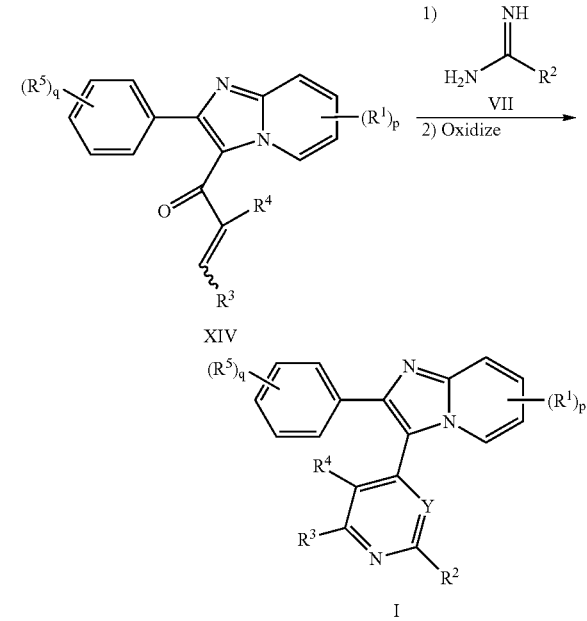

wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay, —OHet, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Ay, —$C(O)NHR^{10}$Het, —$C(S)NR^9R^{11}$, —$C(NH)NR^7R^8$, —$C(NH)NR^7$Ay, —$S(O)_nR^9$, —$S(O)_n$Ay, —$S(O)_n$Het, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}O$—$C(O)R^9$, —$R^{10}O$—C(O)Ay, —$R^{10}O$—C(O)Het, —$R^{10}O$—$S(O)_nR^9$, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^1$ groups together with the atoms to which they are bonded form a $C_{5-6}$cycloalkyl or a 5 or 6-membered heterocyclic ring containing 1 or 2 heteroatoms;

each $R^7$ and $R^8$ are the same or different and are independently selected from the group consisting of H, alkyl, cycloalkyl, alkenyl, cycloalkenyl, —$OR^9$, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}OR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$;

each $R^9$ and $R^{11}$ are the same or different and are independently selected from the group consisting of H, alkyl, cycloalkyl, —$R^{10}$cycloalkyl, —$R^{10}$OH, —$R_{10}(OR^{10})_w$ where w is 1–10, and —$R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

$R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n$$NR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay;

n is 0, 1 or 2;

Y is N;

$R^3$ and $R^4$ are the same or different and are each independently selected from the group consisting of H, halo, alkyl, alkenyl, cycloalkyl, Ay, Het, —$OR^7$, —OAy, —$C(O)R^7$, —C(O)Ay, —$CO_2R^7$, —$CO_2$Ay, —$SO_2NHR^9$, —$NR^7R^8$, —$NR^7$Ay, —NHHet, —$NHR^{10}$Het, —$R^{10}$cycloalkyl, —$R^{10}OR^7$, —$R^{10}$OAy, $R^{10}NR^7R^8$ and —$R^{10}NR^7$Ay;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, —$OR^7$, —OAy, —OHet, —$OR^{10}$Ay, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Het, —$C(S)NR^9R^{11}$, —$C(NH)NR^7R^8$, —$C(NH)NR^7$Ay, —$S(O)_nR^9$, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Het, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^5$ groups together with the atoms to which they are bonded form a $C_{5-6}$ cycloalkyl or aryl; and $M^1$ is Li, Mg-halide or cerium-halide, wherein halide is halo.

Generally, the process for preparing compounds of formula (I) wherein Y is N and $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n NR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay, (all formulas and all other variables having been defined above in connection with Scheme 3), comprises the following steps:

(a) reacting an aminopyridine of formula (III) with a 2-bromoacetophenone of formula (II) to prepare a compound of formula (IV);

(b) formylating the compound of formula (IV) to prepare a compound of formula (VIII);

(c) reacting the compound of formula (VIII) with a compound of formula (XII) to prepare a compound of formula (XIII);

(d) oxidizing the compound of formula (XIII) to prepare a compound of formula (XIV); and (e) reacting a compound of formula (XIV) with a compound of formula (VII) followed by oxidation to prepare a compound of formula (I).

More specifically, compounds of formula (I) wherein Y is N and $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_nNR^7R^8$, —$S(O)_n$Het, —$NR^7R^8$, —NHHet, —$NHR^{10}$Ay, —$NHR^{10}$Het, —$R^{10}NR^7R^8$ and —$R^{10}NR^7$Ay, can be prepared by reacting a compound of formula (XIV) with a compound of formula (VII) followed by oxidative aromatization.

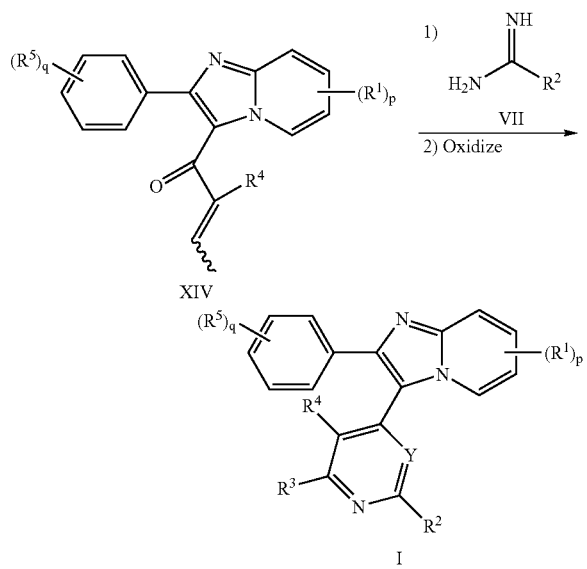

wherein all variables are as defined above in connection with Scheme 3.

The condensation is conveniently carried out by treating the compound of formula (XIV) with a compound of formula (III) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Preferably in the same reaction vessel, the dihydropyrimidine intermediate may be oxidized to a compound of formula (I) by the addition of an oxidizing agent. The reaction may be heated to 50–150° C. or performed at ambient temperature. Preferably, the oxidizing agent is oxygen ($O_2$), palladium on carbon, 2,3-dichloro-5,6-dicyano-1,4-benzoquinone, and the like.

Compounds of formula (XIV) may be conveniently prepared by oxidation of compounds of formula (XIII).

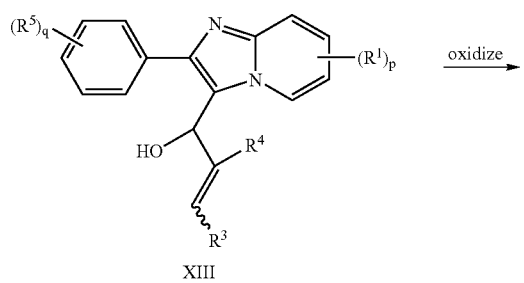

-continued

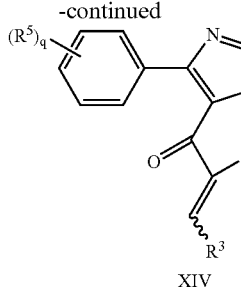

XIV wherein all variables are as defined above in connection with Scheme 3.

Preferred oxidizing agents for the oxidation of compounds of formula (XIII) include but are not limited to manganese dioxide, and the like. The oxidation is typically carried out in an inert solvent such as for example, dichloromethane, chloroform, N,N-dimethylformamide, ether, and the like. In another embodiment the compound of formula (XIII) is oxidized using oxidation methods well known to those skilled in the art of organic chemistry such as Swern oxidation (Omura, K.; Swern, D. *Tetrahedron*, 1978, 34, 1651) or Dess Martin periodinane oxidation (Dess, D. B.; Martin, J. C. *J. Org. Chem.*, 1983, 48, 4155).

Compounds of the formula (XIII) may be conveniently prepared by reacting a compound of formula (VIII) with a compound of formula (XII).

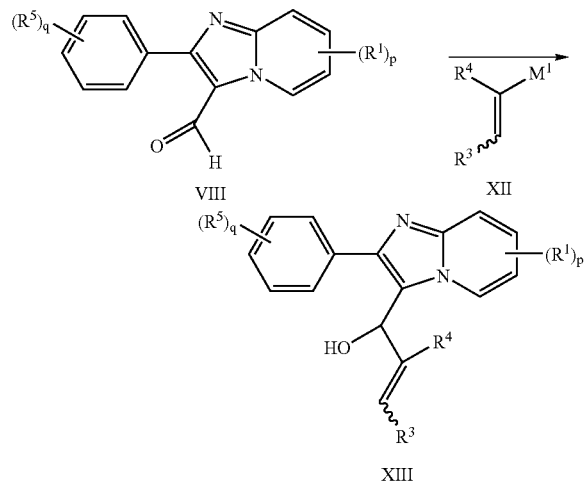

wherein $M^1$ is a metal such as for example, lithium, magnesium(II) halides, Cerium(III) halides, and the like and all other variables are as defined above in connection with Scheme 3.

Compounds of formula (XII) may be purchased from commercial sources or prepared by methods known to one skilled in the art. The compounds of formula (VIII) may be prepared using the methods described above in connection with Scheme 2 above.

In addition to the foregoing process for preparing certain compounds of formula (I), the present invention also provides certain intermediate compounds for use in the preparation of such compounds of formula (I) according to the foregoing process. Such intermediates are described above in Scheme 3.

Compounds of formula (I), may also be conveniently prepared by a process outlined in Scheme 4 below.

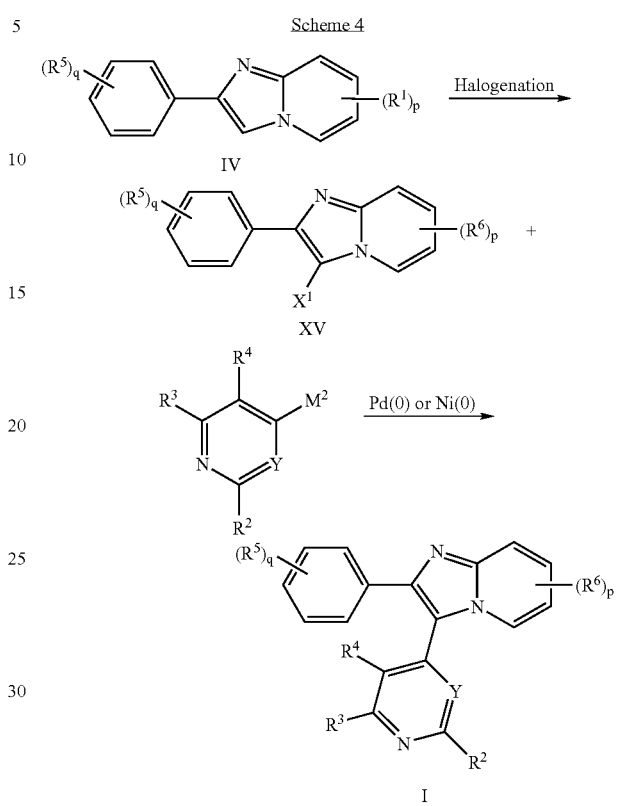

wherein:

p is 0, 1, 2, 3 or 4;

each $R^1$ is the same or different and is independently selected from the group consisting of halo, alkyl, alkenyl, alkynyl, cycloalkyl, cycloalkenyl, Ay, Het, —$OR^7$, —OAy, —$OR^{10}$Ay; —OHet, —$OR^{10}$Het, —$C(O)R^9$, —C(O)Ay, —C(O)Het, —$CO_2R^9$, —$C(O)NR^7R^8$, —$C(O)NR^7$Ay, —$C(O)NHR^{10}$Ay, —$C(O)NHR^{10}$Het, —$C(S)NR^9R^{11}$, —$C(NH)NR^7R^8$, —$C(NH)NR^7$Ay, —$S(O)_nR^9$, —S(O)Ay, —$S(O)_n$Het, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}$Ay, —$R^{10}$Het, —$R^{10}$O—$C(O)R^9$, —$R^{10}$O—C(O)Ay, —$R^{10}$O—C(O)Het, —$R^{10}$O—$S(O)_nR^9$, —$R^{10}OR^9$, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7$Ay, —$R^{10}NHC(NH)NR^9R^{11}$, cyano, nitro and azido; or two adjacent $R^1$ groups together with the atoms to which they are bonded form a $C_{5-6}$cycloalkyl or a 5 or 6-membered heterocyclic ring containing 1 or 2 heteroatoms;

each $R^7$ and $R^8$ are the same or different and are independently selected from the group consisting of H, alkyl, cycloalkyl, alkenyl, cycloalkenyl, —$OR^9$, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}OR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^{10}$, —R$^{10}$SO$_2$NR$^9$R$^{11}$, —R$^{10}$SO$_2$NHCOR$^9$, —R$^{10}$NR$^9$R$^{11}$, —R$^{10}$NHCOR$^9$, —R$^{10}$NHSO$_2$R$^9$ and —R$^{10}$NHC(NH)NR$^9$R$^{11}$;

each R$^9$ and R$^{11}$ are the same or different and are independently selected from the group consisting of H, alkyl, cycloalkyl, —Rcycloalkyl, —R$^{10}$OH, —R$_{10}$(OR$^{10}$)$_w$ where w is 1–10, and —R$^{10}$NR$^{10}$R$^{10}$;

each R$^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

R$^2$ is selected from the group consisting of halo, alkenyl, cycloalkyl, cycloalkenyl, Ay, Het, —OR$^7$, —OAy, —OHet, —OR$^{10}$Het, —S(O)$_n$R$^9$, —S(O)$_n$Ay, —S(O)$_n$NR$^7$R$^8$, —S(O)$_n$Het, —NR$^7$R$^8$, —NHHet, —NHR$^{10}$Ay, —NHR$^{10}$Het, —R$^{10}$NR$^7$R$^8$ and —R$^{10}$NR$^7$Ay;

n is 0, 1 or 2;

Y is N or CH;

R$^3$ and R$^4$ are the same or different and are each independently selected from the group consisting of H, halo, alkyl, alkenyl, cycloalkyl, Ay, Het, —OR$^7$, —OAy, —C(O)R$^7$, —C(O)Ay, —CO$_2$R$^7$, —CO$_2$Ay, —SO$_2$NHR$^9$, —NR$^7$R$^8$, —NR$^7$Ay, —NHHet, —NHR$^{10}$Het, —R$^{10}$cycloalkyl, —R$^{10}$OR$^7$, —R$^{10}$OAy, —R$^{10}$NR$^7$R$^8$ and —R$^{10}$NR$^7$Ay;

q is 0, 1, 2, 3, 4 or 5;

each R$^5$ is the same or different and is independently selected from the group consisting of halo, alkyl, alkenyl, alkynyl, cycloalkyl, cycloalkenyl, Ay, Het, —OR$^7$, —OAy, —OHet, —OR$^{10}$Ay, —OR$^{10}$Het, —C(O)R$^9$, —C(O)Ay, —C(O)Het, —CO$_2$R$^9$, —C(O)NR$^7$R$^8$, —C(O)NR$^7$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Het, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent R$^5$ groups together with the atoms to which they are bonded form a C$_{5-6}$ cycloalkyl or aryl;

X$^1$ is halo, preferably bromo or iodo; and

M$^2$ is —B(OH)$_2$, —B(ORa)$_2$, —B(Ra)$_2$, —Sn(Ra)$_3$, Zn-halide, ZnRa, Mg-halide where Ra is alkyl or cycloalkyl and halide is halo.

Generally, the process for preparing compounds of formula (I) (all formulas and variables having been defined above in connection with Scheme 4), comprises the following steps:

(a) reacting an aminopyridine of formula (III) with a 2-bromoacetophenone of formula (II) to prepare a compound of formula (IV);

(b) halogenating the compound of formula (IV) to prepare a compound of formula (XV); and (c) reacting a compound of formula (XV) with a compound of formula (XVI) to prepare a compound of formula (I).

More specifically, compounds of formula (I) can be prepared by by reacting a compound of formula (XV) with a compound of formula (XVI).

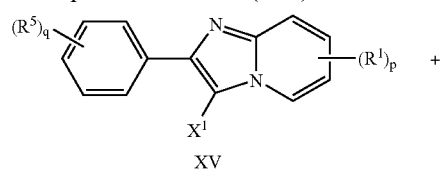

XV

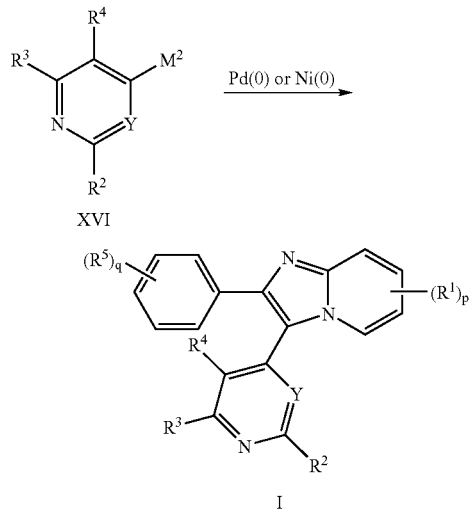

wherein all variables are as defined above in connection with Scheme 4.

The reaction may be carried out in an inert solvent, in the presence of a palladium(0) or nickel(0) catalyst. The reaction may optionally be heated to about 50–150° C. Preferably the reaction is performed by reacting equimolar amounts of a compound of formula (XV) with a Het-metal compound of formula (XVI), but the reaction may also be performed in the presence of an excess of the compound of formula (XVI). The palladium or nickel catalyst is preferably present in 1–10 mol % compared to the compound of formula (XV). Examples of suitable palladium catalysts include but are not limited to, tetrakis(triphenylphosphine) palladium(0), dichlorobis(triphenylphosphine)palladium (II), tris(dibenzylideneacetone)dipalladium(0), and bis (diphenylphosphinoferrocene)palladium(II) dichloride. Suitable solvents include but are not limited to, N,N-dimethylformamide, toluene, tetrahydrofuran, dioxane, and 1-methyl-2-pyrrolidinone. When the Het-metal compound of formula (XVI) is an arylboronic acid or ester or an arylborinate the reaction is more conveniently carried out by adding a base in a proportion equivalent to, or greater than, that of the compound of formula (XVI). Het-metal compounds of formula (XVI) may be obtained from commercial sources or prepared either as discreet isolated compounds or generated in situ using methods known to one skilled in the art (Suzuki, A. J. Organomet. Chem. 1999, 576, 147; Stille, J. Angew. Chem. Int. Ed. Engl. 1986, 25, 508; Snieckus, V. J. Org. Chem. 1995, 60, 292).

Compounds of formula (XV) can be prepared from compounds of formula (IV) by a halogenation procedure.

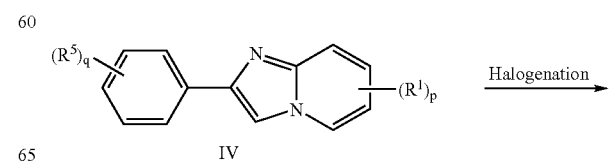

IV

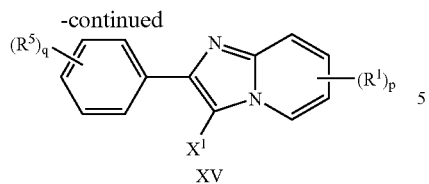

XV wherein all variables are as defined above in connection with Scheme 4.

Typically, the halogenation reaction is carried out by treating the compounds of formula (IV) with a halogenating agent in a suitable solvent. Suitable halogenating agents include but are not limited to, iodine, N-bromosuccinimide, trialkylammonium tribromides; bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

The compounds of formula (IV) can be prepared according to the methods described above in connection with Scheme 1.

In addition to the foregoing process for preparing compounds of formula (I), the present invention also provides certain intermediate compounds for use in the preparation of such compounds of formula (I) according to the foregoing process. Such intermediates are described in connection with Scheme 4 above.

Each of the foregoing processes may further comprise the step of converting the compounds of formula (I) to a salt, solvate, or physiologically functional derivative thereof, using techniques well known to those skilled in the art.

As will be apparent to those skilled in the art, a compound of formula (I) may be converted to another compound of formula (I) using techniques well known in the art. For example, one method of converting a compound of formula (I) to another compound of formula (I) comprises a) oxidizing a compound of formula (I-A) to prepare a compound of formula (I-B) and then b) optionally reacting a compound of formula (I-B) with an oxygen or amine nucleophile selected from the group consisting of Het bonded through N, —OR$^7$, —OAy, —OHet, —OR$^{10}$Het, —NR$^7$R$^8$, —NHHet, —NHR$^{10}$Ay and —NHR$^{10}$Het to produce a compound of formula (I) wherein R$^2$ is selected from the group consisting of Het bonded through N, —OR$^7$, —OAy, —OHet, —OR$^{10}$Het, —NR$^7$R$^8$, —NHHet, —NHR$^{10}$Ay and —NHR$^{10}$Het.

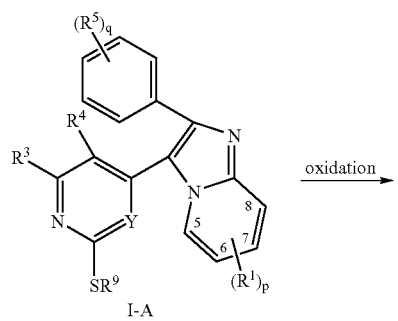

I-A

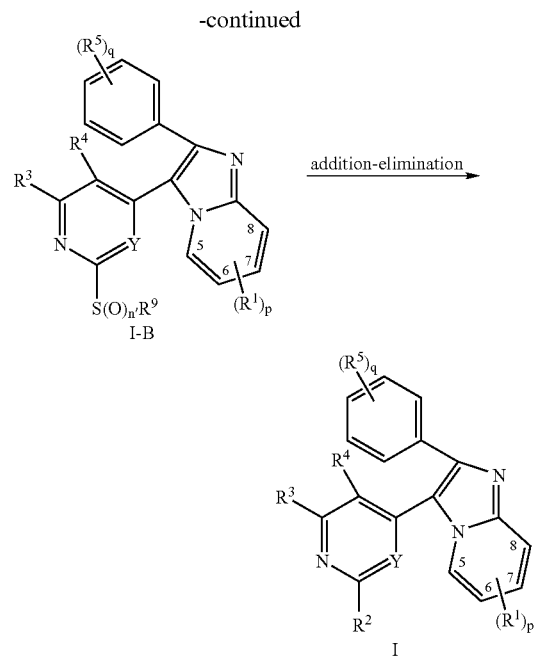

wherein R$^2$ is selected from the group consisting of Het bonded through N —OR$^7$, —OAy, —OHet, —OR$^{10}$Het, —NR$^7$R$^8$, —NHHet, —NHR$^{10}$Ay and —NHR$^{10}$Het and n' is 1 or 2; and all other variables are as defined in connection with any of the processes described above.

More specifically, a compound of formula (I) can be prepared by reacting a compound of formula (I-B) (i.e., a compound of formula (I) wherein R$^2$ is —S(O)$_n$R$^9$ where n' is 1 or 2) with an oxygen or amine nucleophile selected from the group consisting of Het bonded through N, —OR$^7$, —OAy, —OHet, —OR$^{10}$Het, —NR$^7$R$^8$, —NHHet, —NHR$^{10}$Ay and —NHR$^{10}$Het. The reaction may be carried out neat or in a suitable solvent and may be heated to 50–150° C. Typically the solvent is a lower alcohol such as methanol, ethanol, isopropanol and the like or solvent such as N,N-dimethylformamide or tetrahydrofuran, and the like. Optionally a base may be used to facilitate the reaction. Typically the base can be potassium carbonate, or an amine base such as triethylamine. Compounds of the formula (I-B) may be conveniently prepared by reacting a compound of formula (I-A) (i.e., a compound of formula (I) wherein R$^2$ is —S(O)$_n$R$^9$ where n is 0) with an oxidizing agent in an inert solvent, optionally in the presence of a base.

Typically the oxidizing agent is a peracid such as m-chloroperbenzoic acid or the like optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like.

Compounds of the formula (I-A) are prepared by methods described above wherein R$^2$ is —SR$^9$ from the reaction of a compound selected from the group consisting of a compound of formula (VI), a compound of formula (XI) and a compound of formula (XIV) with a compound of formula (VII-A) (i.e., a compound of formula (VII) wherein R$^2$ is —SR$^9$). The requisite compound of formula (VII-A) can be obtained from commercial sources or prepared by methods known to one skilled in the art.

Another particularly useful method for converting a compound of formula (I) to another compound of formula (I) comprises reacting a compound of formula (I-C) (i.e., a compound of formula (I) wherein R² is fluoro) with an amine nucleophile (including substituted amines, heterocycles and heteroaryls, particularly those linked through N), and optionally heating the mixture to 50–150° C. to prepare a compound of formula (I-D) (i.e., a compound of formula (I) wherein R² is selected from the group consisting of Het, —NR⁷R⁸, —NHHet, —NHR¹⁰Ay and —NHR¹⁰Het).

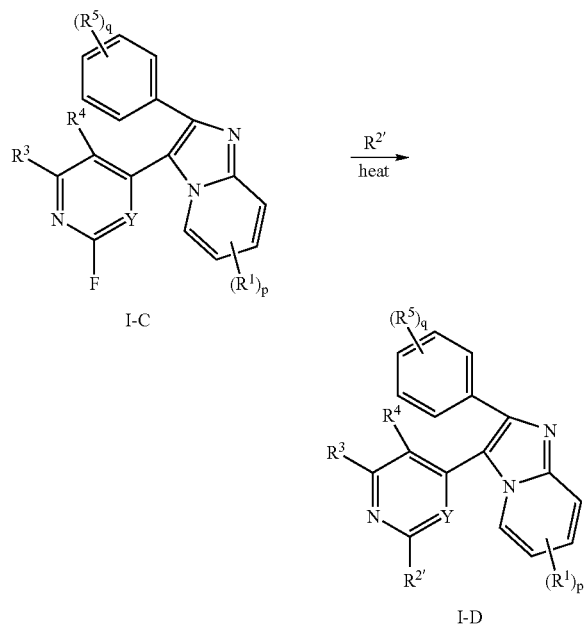

wherein R²' is an amine nucleophile selected from the group consisting of Het, —NR⁷R⁸, —NHHet, —NHR¹⁰Ay, and —NHR¹⁰Het all other variables are as defined in connection with any of the processes described above.

This procedure may be carried out by mixing a compound of formula (I-C) in a neat amine, or in a suitable solvent with an excess of amine to produce a compound of formula (I-D). Typically the solvent is a lower alcohol such as methanol, ethanol, isopropanol or the like. Other suitable solvents may include N,N-dimethylform-amide, 1-methyl-2-pyrrolidine and the like. One skilled in the art will appreciate that other amines such as amines of the formula NH₂Het, H-Het bonded through N, H—NHR¹⁰Het, H—NHR¹⁰Ay, and the like may also be employed in the foregoing conversion and are contemplated by the instant invention.

As a further example, a compound of formula (I-E) where X is halogen, may be converted to a compound of formula (I-F) using amination techniques known to those skilled in the art.

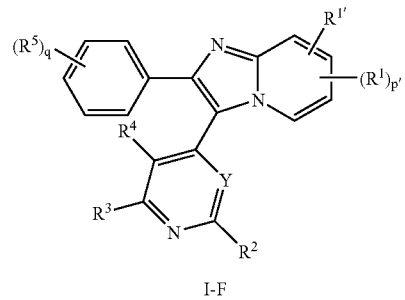

wherein:

X is halo, such as chloro, bromo or iodo;

R¹' is an amine nucleophile selected from the group consisting of Het bonded through N, —NR⁷R⁸, —NHHet, —NHR¹⁰Ay and —NHR¹⁰Het;

p' is 0, 1, 2 or 3;

and all other variables are as defined in connection with any of the Schemes described above.

The reaction can be carried out via an adaptation of procedures found in the literature (Wolfe, J. P.; Buchwald, S. L *J. Org. Chem.* 2000, 65, 1144) wherein a compound of the formula (I-E) is treated with an amine, a palladium (0) or nickel (0) source and a base, optionally in a suitable solvent, at a temperature ranging from ambient temperature to 200° C. Suitable sources of palladium (0) include but are not limited to palladium(II) acetate and tris(dibenzylideneacetone) dipalladium (0). Typical bases for use in the reaction include, for example sodium tert-butoxide and cesium carbonate. The reaction can be carried out in neat amine or in a suitable solvent. Toluene is an example of a suitable solvent.

As a further example, a compound of formula (I-G) (i.e., a compound of formula (I) wherein q is 1 or more and at least one R⁵ is —O-methyl) may be converted to a compound of formula (I-H) (i.e., a compound of formula (I) wherein q is 1 or more and at least one R⁵ is —OH) using conventional demethylation techniques. Additionally, a compound of formula (I-H) may optionally be converted to a compound of formula (I-J) (i.e., a compound of formula (I) wherein q is 1 or more and at least one R⁵ is —OR¹⁰). For example, the foregoing conversions are represented schematically as follows:

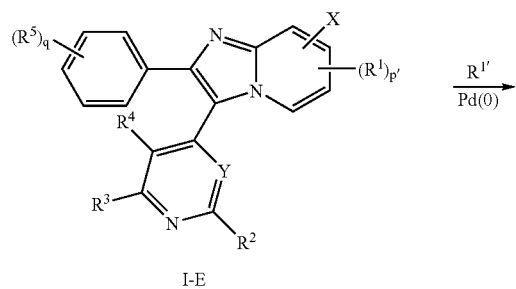
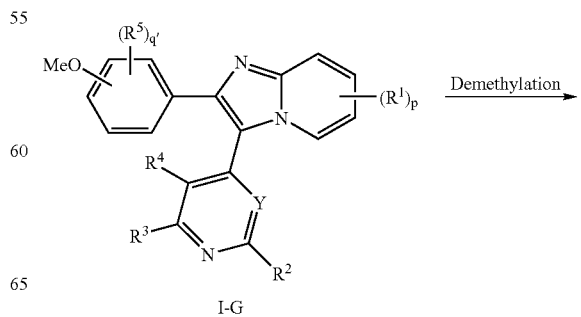

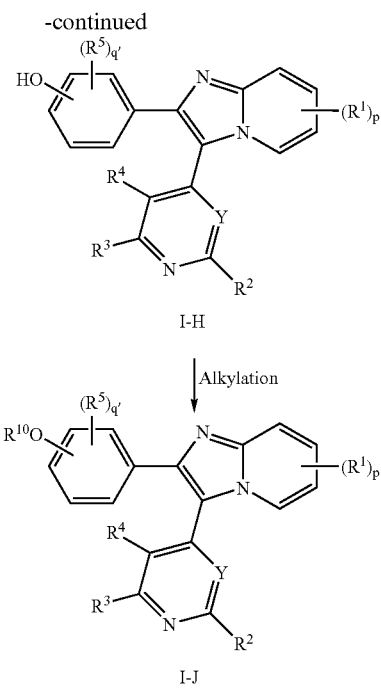

wherein q' is 1, 2, 3 or 4; Me is methyl, and all other variables are as defined in connection with any of the processes described above.

The demethylation reaction may be carried out by treating a compound of formula (I-G) in a suitable solvent with a Lewis acid at a temperature of −78° C. to room temperature, to produce a compound of formula (I-H). Typically the solvent is an inert solvent such as dichloromethane, chloroform, acetonitrile, toluene and the like. The Lewis acid may be boron tribromide, trimethylsilyl iodide and the like.

Optionally, a compound of formula (I-H) may be further converted to a compound of formula (I-J) by an alkylation reaction. The alkylation reaction may be carried out by treating a compound of formula (I-H) in suitable solvent with an alkyl halide of formula $R^{10}$-Halo where $R^{10}$ is as defined above, to form another compound of formula (I-J). The reaction is preferably carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

The foregoing reaction methods can also be used to convert a compound of formula (I) wherein at least one $R^1$ is —OMe to a compound of formula (I) wherein at least one $R^1$ is —OH and a compound of formula (I) wherein at least one $R^1$ is —$OR^{10}$. In another embodiment, the foregoing methods are employed to make the same conversion when $R^3$ or $R^4$ is —OMe, to prepare a compound of formula (I) wherein $R^3$ or $R^4$ is —OH or a compound of formula (I) wherein $R^3$ or $R^4$ is —$OR^{10}$.

In yet another example, a compound of formula (I-K) (i.e., a compound of formula (I) wherein q is 1 or more and at least one $R^5$ is halo) or a compound of formula (I-M) (i.e. a compound of formula (I) wherein q is 1 or more and at least one $R^5$ is nitro) can be converted to a compound of formula (I-L) (i.e., a compound of formula (I) wherein q is 1 or more and at least one $R^5$ is —$NH_2$). Optionally, a compound of formula (I-L) may then be converted to a compound of formula (I-N) (i.e., a compound of formula (I) wherein q is 1 or more and at least one $R^5$ is —$NR^7R^8$ where $R^7$ and $R^8$ are not both H). For example, the foregoing conversions are represented schematically as follows:

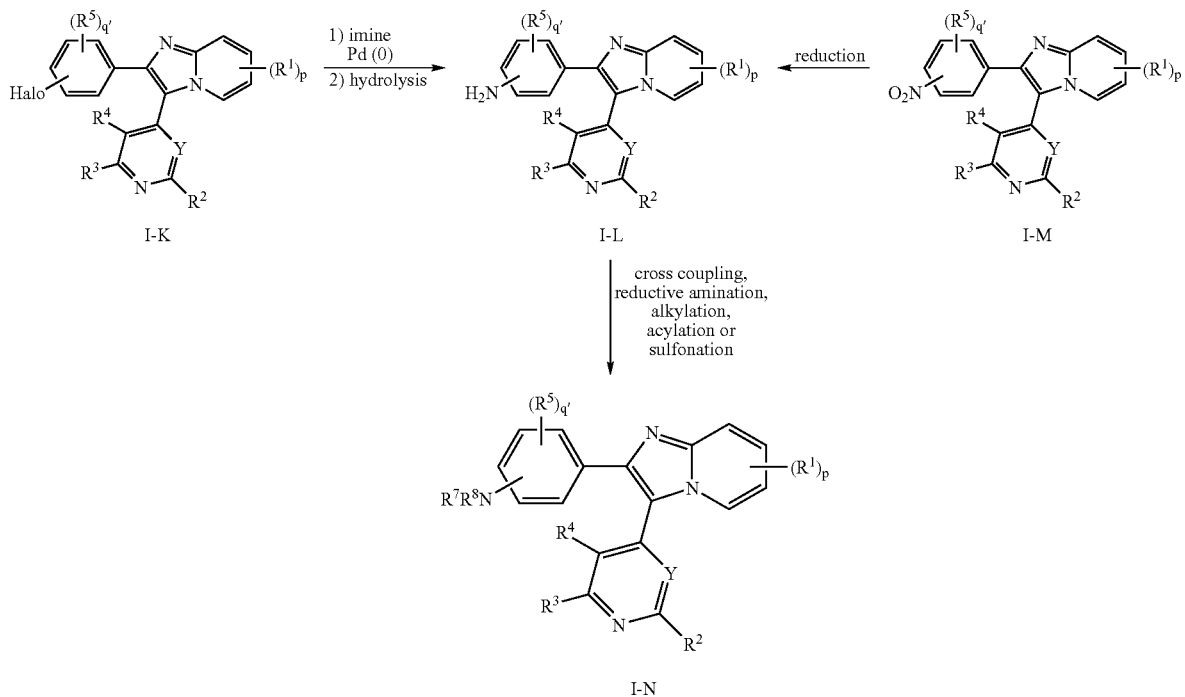

wherein q' is 1, 2, 3 or 4, and all other variables are as defined in connection with any of the processes described above.

The process of converting a compound of formula (I-K) to a compound of formula (I-L) is carried out by reacting a compound of formula (I-K) with an imine in the presence of a palladium (0) source, a base and a suitable ligand, followed by hydrolysis to give a compound of formula (I-L). See J. Wolfe, et al., *Tetrahedron Letters* 38:6367–6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

A compound of formula (I-L) can also be obtained from a compound of formula (I-M) by reduction. The reduction can conveniently be carried out by using zinc, tin or iron and acid, by using tin(II)chloride, or by using palladium or platinum catalysts under hydrogen atmosphere in a suitable solvent as obvious to one skilled in the art of organic synthesis.

Reaction of a compound of formula (I-L) with a compound of formula $R^7$-halogen in a suitable solvent in the presence of base, optionally with heating may be used to prepare a compound of formula (I-N). Typically the base is triethylamine or pyridine and the solvent is N,N-dimethylformamide and the like.

Additional compounds of formula (I-N) can be obtained by reductive amination of a compound of formula (I-L) with a ketone or aldehyde. See, A. Abdel-Magid, et al., *J. Org. Chem.* 61:3849–3862 (1996). Typically a compound of formula (I-L) is treated with an aldehyde or a ketone in the presence of an acid, such as acetic acid, and a reducing agent, such as sodium triacetoxyborohydride and the like, in an inert solvent such as dichloroethane and the like.

The foregoing reaction methods can also be used to convert a compound of formula (I) wherein at least one $R^1$ is halo to a compound of formula (I) wherein at least one $R^1$ is —$NH_2$ or a compound of formula (I) wherein at least one $R^6$ is —$NR^7R^8$ (where $R^7$ and $R^8$ are not both H). In another embodiment, the foregoing methods are employed to make the same conversion when $R^3$ or $R^4$ is halo, to prepare a compound of formula (I) wherein $R^3$ or $R^4$ is —$NH_2$ or a compound of formula (I) wherein $R^3$ or $R^4$ is —$NR^7R^8$ (where $R^7$ and $R^8$ are not both H).

Other transformations well known to those skilled in the art for use with anilines may be used to convert a compound of formula (I-L) to a compound of formula (I-N).

As obvious to those skilled in the art, the steps of the foregoing synthesis reactions and the conversion reactions described above can be rearranged in any manner suitable according to conventional knowledge in the art. Hence, the order of the steps in the foregoing synthesis schemes and in the conversion reactions described above is not critical to the practice of the present invention.

Based upon this disclosure and the examples contained herein one skilled in the art can readily convert compounds of formula (I) or a pharmaceutically acceptable salt, solvate or physiologically functional derivative thereof into another compound of formula (I), or a pharmaceutically acceptable salt, solvate or physiologically functional derivative thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one preferred embodiment, the compounds of formula (I) are tritiated.

The radiolabeled compounds of formula (I) and the biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compounds of formula (I) to the target protein. More specifically, suitable assay methods will include competition binding assays. The radiolabeled compounds of formula (I) can be employed in assays according to the methods conventional in the art.

The following examples are illustrative embodiments of the invention, not limiting the scope of the invention in any way, the invention being defined by the claims which follow. Reagents are commercially available or are prepared according to procedures in the literature. Example numbers refer to those compounds listed in the tables above. $^1H$ and $^{13}C$ NMR spectra were obtained on Varian Unity Plus NMR spectrophotometers at 300 or 400 MHz, and 75 or 100 MHz respectively. $^{19}F$ NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

3-[2-(Cyclopentylamino)-4-pyrimidinyl]-2-(4-fluorophenyl)imidazo[1,2-α]pyridin-8-amine

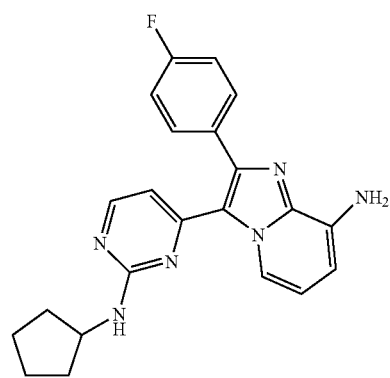

a) 2-(4-Fluorophenyl)-8-nitroimidazo[1,2-α]pyridine.

To a solution of 2-amino-3-nitropyridine (1.3 g, 9.3 mmol) in N,N-dimethylformamide (20 mL) was added 2-bromo-4'-fluoroacetophenone (2 g, 9.3 mmol) and the reaction mixture was heated at reflux for 6 hours. The resulting mixture was concentrated to a solid in vacuo. This residue was dissolved in dichloromethane and the organic phase was washed with aqueous sodium bicarbonate and an aqueous sodium chloride solution. The organic phase was dried (magnesium sulfate), filtered through a silica gel pad and concentrated to give a solid. This solid was recrystallized from methanol to give 870 mg (36%) of 2-(4-fluorophenyl)-8-nitroimidazo[1,2-α]pyridine as a brown solid. $^1$H NMR ($d_6$-DMSO): δ 8.98 (d, 1H), 8.69 (s,1H), 8.32 (d, 1H), 8.10 (q, 2H), 7.36 (t, 2H), 7.15 (t, 1H); $^{19}$F NMR (DMSO-$d_6$) δ −113.7; MS m/z 258 (M+1).

b) 1-[2-(4-Fluorophenyl)-8-nitroimidazo[1,2-α]pyridin-3-yl]ethanone.

2-(4-Fluorophenyl)-8-nitroimidazo[1,2-α]pyridine (2 g, 7.8 mmol) was added to acetic anhydride (15 mL). To this mixture was added a catalytic amount of concentrated sulfuric acid and the reaction mixture was heated to reflux for 1 hour. The resulting mixture was concentrated to a slurry, neutralized by addition of saturated aqueous sodium bicarbonate and extracted with ethyl acetate. The organic phase was dried (magnesium sulfate), filtered and concentrated to a solid. This solid was purified by silica gel chromatography (1:1 ethyl acetate:hexane) to give 1.3 g (55%) of 1-[2-(4-fluorophenyl)-8-nitroimidazo[1,2-α]pyridin-3-yl]ethanone as a brown solid. $^1$H NMR (DMSO-$d_6$): δ 9.93 (d, 1H), 8.62 (d, 1H), 7.78 (q, 2H), 7.46 (m, 3H), 2.20 (s, 3H); MS m/z 300 (M+1).

c) 1-[8-Amino-2-(4-fluorophenyl)imidazo[1,2-α]pyridin-3-yl]ethanone.

A solution of 1-[2-(4-fluorophenyl)-8-nitroimidazo[1,2-α]pyridin-3-yl]ethanone (100 mg, 0.33 mmol) in methanol (3 mL) was added to a suspension of iron (93 mg, 1.7 mmol) and ammonium chloride (149 mg, 2.8 mmol) in aqueous methanol. This reaction mixture was heated to reflux for 10 hours. The reaction mixture was filtered and the filtrate concentrated under reduced pressure to a solid. This solid was purified by silica gel chromatography (5% methanol in dichloromethane) to give 63 mg (70%) of 1-[8-amino-2-(4-fluorophenyl)imidazo[1,2-α]pyridin-3-yl]ethanone as a foam. $^1$H NMR (CDCl$_3$): δ 9.21 (d, 1H), 7.61 (m, 2H), 7.25 (m, 2H), 6.94 (t, 1H) 6.72 (d, 1H), 4.63 (broad s, 2H), 2.19 (s, 3H); MS m/z 270 (M+1).

d) N'-[3-[(2E)-3-(Dimethylamino)-2-propenoyl]-2-(4-fluorophenyl)imidazo[1,2-α]pyridin-8-yl]-N,N-dimethylimidoformamide.

A solution of 1-[8-amino-2-(4-fluorophenyl)imidazo[1,2-α]pyridin-3-yl]ethanone (150 mg, 0.56 mmol) in N,N-dimethylformamide dimethyl acetal (5 mL) was heated at reflux for 6 days. The mixture was cooled to room temperature, ethyl acetate and water were added. The phases were separated and the organic layer was washed with brine. The aqueous layer was extracted with ethyl acetate and the combined organics were dried over magnesium sulfate. Filtration and concentration followed by silica gel chromatography (1:1 acetone:ethyl acetate) gave 130 mg (62%) of N'-[3-[(2E)-3-(dimethylamino)-2-propenoyl]-2-(4-fluorophenyl)imidazo[1,2-α]pyridin-8-yl]-N,N-dimethylimidoformamide as a foam. $^1$H NMR (CDCl$_3$): δ 9.28 (d, 1H), 8.53 (s, 1H), 7.76 (q, 2H), 7.62 (d, 1H), 7.13 (t, 2H), 6.87 (m, 2H), 5.12 (d, 1H), 2.4–3.3 (m, 12H); MS m/z 380 (M+1).

e) N-Cyclopentylguanidine hydrochloride.

(Prepared by modification of a procedure from Bannard, R. A. B.; Casselman, A. A.; Cockburn, W. F.; and Brown, G. M. Can. J. Chem. 1958, 36, 1541–1549). To a solution of 2-methyl-2-thiopseudourea sulfate (13.9 g, 50.0 mmol) in water (40 mL) was added cyclopentylamine (14.8 mL, 150 mmol). The resultant mixture was heated to 55° C. for 20 minutes and then to reflux for 2.5 hours. The mixture was cooled to room temperature and concentrated in vacuo and azeotroped with methanol. Water was added (~100 mL) and Amberlite IRA 400 (Cl$^−$) resin was added. The mixture was stirred for 1 hour and then the resin was removed by filtration. The solution was concentrated in vacuo and azeotroped with methanol. The residue was recrystallized from methanol-acetone to yield N-cyclopentylguanidine hydrochloride (7.0 g, 86%) as a fine white solid. $^1$H NMR (D$_2$O): δ 3.62 (m, 1H), 1.75 (m, 2H), 1.52–1.32 (m, 6H); $^{13}$C NMR (D$_2$O) δ 156.23, 53.11, 32.15, 23.13; MS m/z 128 (M+1).

f) N'-[3-[2-(Cyclopentylamino)-4-pyrimidinyl]-2-(4-fluorophenyl)imidazo[1,2-α]pyridin-8-yl]-N,N-dimethylimidoformamide.

To a solution of N'-[3-[(2E)-3-(dimethylamino)-2-propenoyl]-2-(4-fluorophenyl)imidazo[1,2-α]pyridin-8-yl]-N,N-dimethylimidoformamide (130 mg, 0.34 mmol) in N,N-dimethylformamide was added N-cyclopentylguanidine hydrochloride (168 mg, 1.02 mmol), followed by anhydrous potassium carbonate (140 mg, 1.02 mmol). The resulting solution was heated at 100° C. for 16 hours. Upon cooling to room temperature, ethyl acetate and water were added. The phases were separated and the organics were washed with brine. The aqueous layer was extracted with ethyl acetate. The combined organics were dried over magnesium sulfate, filtered and concentrated in vacuo. The residue was purified by silica gel chromatography (ethyl acetate) to give N'-[3-[2-(cyclopentylamino)-4-pyrimidinyl]-2-(4-fluorophenyl)imidazo[1,2-α]pyridin-8-yl]-N,N-dimethylimidoformamide (80 mg, 53%) as a solid. $^1$H NMR (CDCl$_3$): δ 9.09 (broad s, 1H), 8.60 (s, 1H), 8.04 (d, 1H), 7.63 (q, 2H), 7.04 (t, 2H), 6.78 (m, 2H), 6.36 (d, 1H), 5.14 (d, 1H), 4.31 (m, 1H), 3.10 (s, 3H), 3.05 (s, 3H), 2.0–2.1 (m, 2H), 1.4–1.9 (m, 6H); MS m/z 444 (M+1).

g) 3-[2-(Cyclopentylamino)-4-pyrimidinyl]-2-(4-fluorophenyl)imidazo[1,2-α]pyridin-8-amine.

N'-[3-[2-(Cyclopentylamino)-4-pyrimidinyl]-2-(4-fluorophenyl)imidazo[1,2-α]pyridin-8-yl]-N,N-dimethylimidoformamide (70 mg, 0.16 mmol) was dissoved in methanol. To this solution was added 1N aqueous sodium hydroxide and the resulting mixture heated at reflux for 6 hours. The resulting mixture was concentrated in vacuo followed by addition of ethyl acetate and water. The phases were separated and the ethyl acetate phase dried (magnesium sulfate), filtered and concentrated. The resulting solid was purified by silica gel chromatography (ethyl acetate) to give 55 mg (88%) of 3-[2-(Cyclopentylamino)-4-pyrimidinyl]-2-(4-fluorophenyl)imidazo[1,2-α]pyridin-8-amine as a solid. $^1$H NMR (CDCl$_3$): δ 8.97 (d, 1H), 8.12 (d, 1H), 7.68 (q, 2H), 7.15 (t, 2H), 6.78 (t, 1H), 6.54 (d, 1H), 6.41 (d, 1H), 5.24 (d, 1H), 4.60 (s, 2H), 4.40 (m, 1H), 2.0–2.1 (m, 2H), 1.4–1.9 (m, 6H); $^{19}$F NMR (CDCl$_3$) δ −113.7; MS m/z 389 (M+1).

EXAMPLE 2

4-[8-Chloro-2-(4-fluorophenyl)imidazo[1,2-α]pyridin-3-yl]-N-cyclopentyl-2-pyrimidinamine

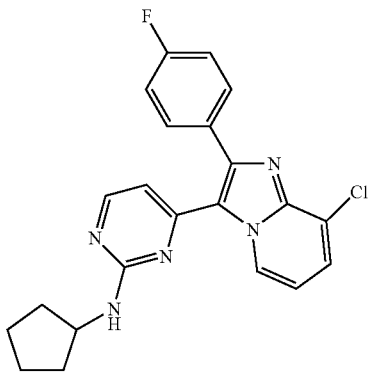

a) 2-Amino-3-chloropyridine.

2,3-Dichloropyridine (20 g, 0.14 moles) was placed in a steel bomb. To this was added concentrated ammonium hydroxide (300 mL), the bomb sealed and heated at 190° C. for 48 hours. The vessel was cooled to room temperature and opened. Ethyl acetate and water were added. The phases were separated and the ethyl acetate phase washed with water, dried (magnesium sulfate), filtered and concentrated to a solid. This solid was crystallized from a small volume of ethyl acetate to give 12.6 g (70%) of 2-amino-3-chloropyridine as a white solid. $^1$H NMR (CDCl$_3$) δ 7.95 (dd, 1H), 7.46 (dd, 1H). 6.58 (q, 1H), 5.0 (broad s, 2H); MS m/z 129 (M+H).

b) 8-Chloro-2-(4-fluorophenyl)imidazo[1,2-α]pyridine.

To a solution of 2-amino-3-chloropyridine (6.51 g, 51 mmol) and 2-bromo-4'-fluoroacetophenone (13.0 g, 60 mmol) in ethanol (100 mL) was added sodium bicarbonate (4.91 g, 60 mmol) and the reaction mixture was heated at reflux for 6 hours. The resulting mixture was concentrated to a solid in vacuo. This residue was dissolved in ethyl acetate and the organic phase was washed with water and an aqueous sodium chloride solution. The organic phase was dried (magnesium sulfate), filtered through a silica gel pad and concentrated to give a solid. This solid was recrystallized from acetonitrile, to give 10.1 g (80%) 8-chloro-2-(4-fluorophenyl)imidazo[1,2-α]pyridine as a solid. $^1$H NMR (CDCl$_3$): δ 8.06 (d, 1H), 7.96 (q, 2H), 7.86 (s, 1H), 7.25 (d, 1H), 7.13 (t, 2H), 6.73 (t, 1H); $^{19}$F NMR (CDCl$_3$) δ −114.0; MS m/z 247 (M+1).

c) 8-Chloro-2-(4-fluorophenyl)imidazo[1,2-α]pyridine-3-carbaldehyde.

N,N-Dimethylformamide (10 mL) was cooled to 0° C. and treated with phosphorous oxychloride (1.0 mL, 11 mmol). After the addition was complete, the mixture was warmed to room temperature and stirred for 10 minutes. To this was added 8-chloro-2-(4-fluorophenyl)imidazo[1,2-α]pyridine (1.15 g, 4.7 mmol) and the resulting solution was stirred overnight. Water was added to the reaction. The mixture was neutralized to pH 7 with ammonium hydroxide. The aqueous phase was extracted with dichloromethane (3×50 mL). The combined organics were washed with brine, dried over magnesium sulfate, filtered and concentrated. The residue was recrystallized from acetonitrile to give 8-chloro-2-(4-fluorophenyl)imidazo[1,2-α]pyridine-3-carbaldehyde (1.1 g, 85%) as a white solid. $^1$H NMR (CDCl$_3$): δ 10.05 (s, 1H), 9.60 (d, 1H), 7.86 (q, 2H), 7.65 (d, 1H), 7.23 (t, 2H), 7.08 (t, 1H); $^{19}$F NMR (CDCl$_3$) δ −110.8; MS m/z 275 (M+1).

d) 1-[8-Chloro-2-(4-fluorophenyl)imidazo[1,2-α]pyridin-3-yl]-2-propyn-1-one.

To a cold (−78° C.) suspension of 8-chloro-2-(4-fluorophenyl)imidazo[1,2-α]pyridine-3-carbaldehyde (0.94 g, 3.42 mmol) in tetrahydrofuran (20 mL) was added ethynylmagnesium bromide (15 mL, 0.5 M in tetrahydrofuran, 7.5 mmol) dropwise. The reaction mixture was stirred at −78° C. for 1 hour, then at 0° C. for 2 hours. The resulting solution was poured into water and extracted with ethyl acetate. The organic layer was washed with water and brine and the combined organics were dried over magnesium sulfate. Filtration and concentration gave a white solid. This solid was dissolved in dichlormethane (60 mL) and to this solution was added manganese dioxide (10 g, 115 mmol). The reaction mixture was stirred at room temperature for 1 hour. The suspension was filtered through a pad of Celite and the filtrate was concentrated and purified by silica gel chromatography (1:1 hexanes:ethyl acetate) to give 1-[8-chloro-2-(4-fluorophenyl)imidazo[1,2-α]pyridin-3-yl]-2-propyn-1-one (0.56 g, 55%) as a white solid. $^1$H NMR (CDCl$_3$) δ 9.67 (d, 1H), 7.68 (m, 3H), 7.12 (m, 3H), 2.89 (s, 1H); $^{19}$F NMR (CDCl$_3$) δ −111.6; MS m/z 299 (M+1).

e) 4-[8-Chloro-2-(4-fluorophenyl)imidazo[1,2-α]pyridin-3-yl]-N-cyclopentyl-2-pyrimidinamine.

To a solution of 1-[8-chloro-2-(4-fluorophenyl)imidazo[1,2-α]pyridin-3-yl]-2-propyn-1-one (740 mg, 2.5 mmol) in ethanol (20 mL) was added cyclopentyl guanidine hydrochloride (600 mg, 3.7 mmol), followed by solid potassium carbonate (510 mg, 3.7 mmol). The resulting solution was heated at 80° C. for 12 hours. The reaction mixture was concentrated to a solid. Water and dichloromethane were added. The phases were separated and the organics were washed with brine, dried over magnesium sulfate, filtered and concentrated in vacuo. The resulting solid was crystallized from acetonitrile, to give 4-[8-chloro-2-(4-fluorophenyl)imidazo[1,2-α]pyridin-3-yl]-N-cyclopentyl-2-pyrimidinamine (600 mg, 59%) as a white solid. $^1$H NMR (CDCl$_3$) δ 9.48 (d, 1H), 8.11 (d, 1H), 7.68 (q, 2H), 7.42 (d, 1H), 7.11 (t, 2H), 6.86 (t, 1H), 6.40 (d, 1H), 5.28 (d, 1H), 4.35 (m, 1H), 2.0–2.1 (m, 2H), 1.4–1.9 (m, 6H); $^{19}$F NMR (CDCl$_3$) δ −113.0; MS m/z 408 (M+1).

EXAMPLE 3

N-Cyclopentyl-3-[2-(cyclopentylamino)-4-pyrimidinyl]-2-(4-fluorophenyl)imidazo[1,2-α]pyridin-8-amine

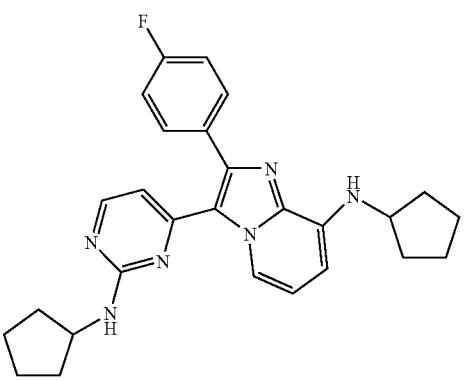

To a solution of 4-[8-chloro-2-(4-fluorophenyl)imidazo[1,2-α]pyridin-3-yl]-N-cyclopentyl-2-pyrimidinamine (200 mg, 0.49 mmol) in cyclopentylamine (10 mL) was added, successively, racemic-2,2'-bis(diphenylphosphino)-1,1'-binaphthyl (91 mg, 0.15 mmol), cesium carbonate (0.24 g, 0.7 mmol) and palladium(II) acetate (22 mg, 0.1 mmol). The resulting mixture was heated in a sealed tube at 100° C. for 18 hours at which time the reaction was judged complete by thin layer chromatography. The solution was cooled to room temperature and ethyl acetate and water were added. The phases were separated and the organic layer was washed with water and brine. The combined organics were dried (magnesium sulfate), filtered and concentrated to a solid. This solid was purified by silica gel chromatography (1:1 hexanes:ethyl acetate) to give N-cyclopentyl-3-[2-(cyclopentylamino)-4-pyrimidinyl]-2-(4-fluorophenyl)imidazo[1,2-α]pyridin-8-amine (120 mg, 55%) as a solid. $^1$H NMR (CDCl$_3$) δ 8.80 (d, 1H), 8.06 (d, 1H), 7.62 (q, 2H), 7.10 (t, 2H), 6.76 (t, 1H), 6.34 (d, 1H), 6.27 (d, 1H), 5.22 (d, 2H), 4.34 (m, 1H), 3.93 (m, 1H), 2.0–2.1 (m, 4H), 1.4–1.9 (m, 12H); $^{19}$F NMR (CDCl$_3$) δ −113.9; MS m/z 457 (M+1).

EXAMPLE 4

N-Cyclopentyl-4-[2-(4-fluorophenyl)-8-(1-pyrrolidinyl)imidazo[1,2-α]pyridin-3-yl]-2-pyrimidinamine

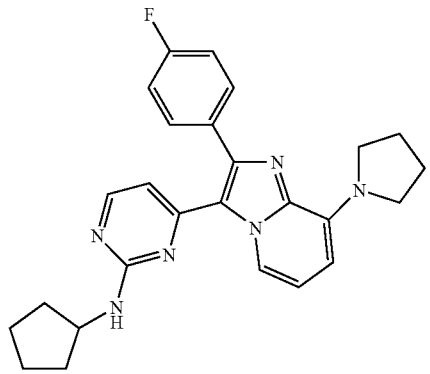

In a similar manner as described in Example 3, from 4-[8-chloro-2-(4-fluorophenyl)imidazo[1,2-α]pyridin-3-yl]-N-cyclopentyl-2-pyrimidinamine (150 mg, 0.37 mmol) and pyrrolidine (5 mL) was obtained N-cyclopentyl-4-[2-(4-fluorophenyl)-8-(1-pyrrolidinyl)imidazo[1,2-α]pyridin-3-yl]-2-pyrimidinamine (70 mg, 43%) as a solid. $^1$H NMR (CDCl$_3$) δ 8.77 (d, 1H), 8.10 (d, 1H), 7.66 (q, 2H), 7.07 (t, 2H), 6.72 (t, 1H), 6.41 (d, 1H), 6.17 (d, 1H), 5.22 (d, 1H), 4.36 (m, 1H), 3.81 (m, 4H), 2.0–2.1 (m, 6H), 1.4–1.9 (m, 6H); $^{19}$F NMR (CDCl$_3$) δ −114.5; MS m/z 443 (M+1).

EXAMPLE 5

N-Butyl-3-[2-(cyclopentylamino)-4-pyrimidinyl]-2-(4-fluorophenyl)imidazo[1,2-α]pyridin-8-amine

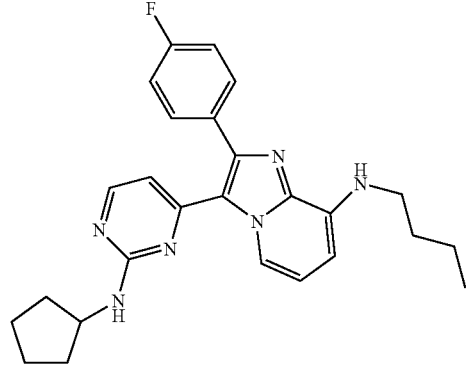

In a similar manner as described in Example 3, from 4-[8-chloro-2-(4-fluorophenyl)imidazo[1,2-α]pyridin-3-yl]-N-cyclopentyl-2-pyrimidinamine (150 mg, 0.37 mmol) and n-butylamine (10 mL) was obtained N-butyl-3-[2-(cyclopentylamino)-4-pyrimidinyl]-2-(4-fluorophenyl)imidazo[1,2-α]pyridin-8-amine (90 mg, 55%) as a solid. $^1$H NMR (CDCl$_3$) δ 8.81 (d, 1H), 8.07 (d, 1H), 7.62 (q, 2H), 7.07 (t, 2H), 6.76 (t, 1H), 6.35 (d, 1H), 6.24 (d, 1H), 5.24 (m, 2H), 4.35 (m, 1H), 3.27 (q, 2H), 2.0–2.1 (m, 2H), 1.4–1.9 (m, 10H), 0.98 (t, 3H); $^{19}$F NMR (CDCl$_3$) δ −113.9; MS m/z 445 (M+1).

EXAMPLE 6

3-[2-(Cyclopentylamino)-4-pyrimidinyl]-2-(4-fluorophenyl)-N-(2-methoxyethyl)imidazo[1,2-α]pyridin-8-amine

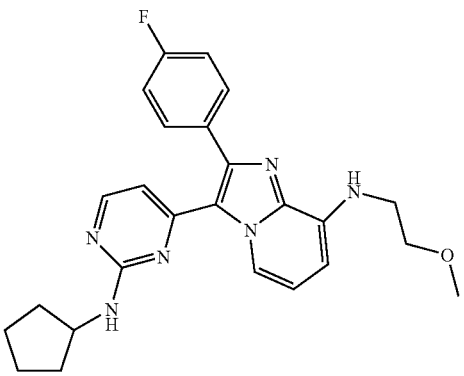

In a similar manner as described in Example 3, from 4-[8-chloro-2-(4-fluorophenyl)imidazo[1,2-α]pyridin-3-yl]-N-cyclopentyl-2-pyrimidinamine (150 mg, 0.37 mmol) and methoxyethylamine (5 mL) was obtained 3-[2-(cyclopentylamino)-4-pyrimidinyl]-2-(4-fluorophenyl)-N-(2-methoxyethyl)imidazo[1,2-α]pyridin-8-amine (70 mg, 42%) as a solid. $^1$H NMR (CDCl$_3$) δ 8.83 (d, 1H), 8.07 (d, 1H), 7.65 (q, 2H), 7.10 (t, 2H), 6.77 (t, 1H), 6.36 (d, 1H), 6.28 (d, 1H), 5.48 (t, 1H), 5.22 (d, 1H), 4.35 (m, 1H), 3.69 (q, 2H), 3.48 (m, 2H), 3.41 (s, 3H), 2.0–2.1 (m, 2H), 1.4–1.9 (m, 6H); $^{19}$F NMR (CDCl$_3$) δ −113.9; MS m/z 447 (M+1).

EXAMPLE 7

4-[8-Chloro-2-(4-fluorophenyl)imidazo[1,2-α]pyridin-3-yl]-N-methyl-2-pyrimidinamine

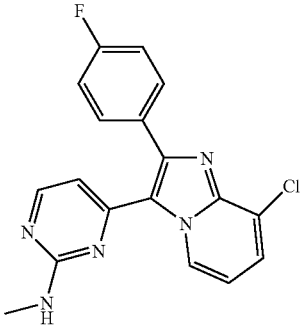

In a similar manner as described in Example 2, from 1-[8-chloro-2-(4-fluorophenyl)imidazo[1,2-α]pyridin-3-yl]-2-propyn-1-one (300 mg, 1.0 mmol), 1-methylguanidine hydrochloride (164 mg, 1.5 mmol) and potassium carbonate (210 mg, 1.5 mmol) was obtained 4-[8-chloro-2-(4-fluorophenyl)imidazo[1,2-α]pyridin-3-yl]-N-methyl-2-pyrimidinamine (270 mg, 76%) as a solid. $^1$H NMR (CDCl$_3$) δ

9.47 (s, 1H), 8.13 (d, 1H), 7.65 (q, 2H), 7.40 (d, 1H), 7.10 (t, 2H), 6.84 (t, 1H), 6.41 (d, 1H), 5.33 (s, 1H), 3.08 (d, 3H); $^{19}$F NMR (CDCl$_3$) δ −113.0; MS m/z 354 (M+1).

EXAMPLE 8

N-Cyclopentyl-2-(4-fluorophenyl)-3-[2-(methylamino)-4-pyrimidinyl]imidazo[1,2-α]pyridin-8-amine

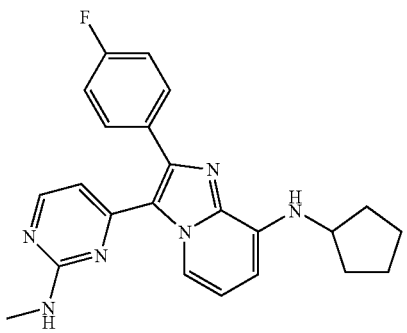

In a similar manner as described in Example 3, from 4-[8-chloro-2-(4-fluorophenyl)imidazo[1,2-α]pyridin-3-yl]-N-methyl-2-pyrimidinamine (126 mg, 0.36 mmol) and cyclopentylamine (5 mL) was obtained N-cyclopentyl-2-(4-fluorophenyl)-3-[2-(methylamino)-4-pyrimidinyl]imidazo[1,2-α]pyridin-8-amine (70 mg, 48%) as a solid. $^1$H NMR (CDCl$_3$) δ 8.80 (d, 1H), 8.09 (d, 1H), 7.63 (q, 2H), 7.10 (t, 2H), 6.77 (t, 1H), 6.37 (d, 1H), 6.28 (d, 1H), 5.24 (m, 2H), 3.95 (m, 1H), 3.09 (d, 3H), 2.0–2.1 (m, 2H), 1.4–1.9 (m, 6H); $^{19}$F NMR (CDCl$_3$) δ −113.9; MS m/z 403 (M+1).

EXAMPLE 9

4-[8-Chloro-2-(4-methoxyphenyl)imidazo[1,2-α]pyridin-3-yl]-N-cyclopentyl-2-pyrimidinamine

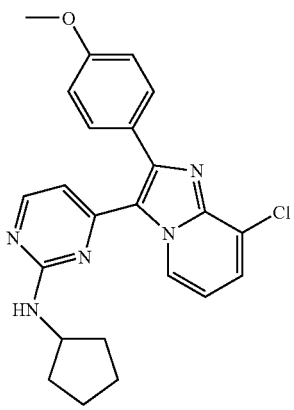

a) 8-Chloro-2-(4-methoxyphenyl)imidazo[1,2-α]pyridine.

In a similar manner as described in Example 2, from 2-amino-3-chloropyridine (6.0 g, 47 mmol), 2-bromo-4'-methoxyacetophenone (11.8 g, 52 mmol) and sodium bicarbonate (4.34 g, 52 mmol) in ethanol (80 mL) was obtained, after recrystallization from ethyl acetate, 8-chloro-2-(4-methoxyphenyl)imidazo[1,2-α]pyridine (8.9 g, 73%) as a solid. $^1$H NMR (CDCl$_3$) δ 8.04 (d, 1H), 7.92 (d, 2H), 7.82 (s, 1H), 7.23 (t, 1H), 6.96 (d, 2H), 6.69 (t, 1H), 3.85 (s, 3H); MS m/z 259 (M+1).

b) 8-Chloro-2-(4-methoxyphenyl)imidazo[1,2-α]pyridine-3-carbaldehyde.

In a similar manner as described in Example 2, from 8-chloro-2-(4-methoxyphenyl)imidazo[1,2-α]pyridine (5 g, 19.4 mmol) and phosphorous oxychloride (2.72 mL, 29.1 mmol) in N,N-dimethylformamide was obtained, after recrystallization from acetonitrile, 8-chloro-2-(4-methoxyphenyl)imidazo[1,2-α]pyridine-3-carbaldehyde (4.8 g, 86%) as a white solid. $^1$H NMR (CDCl$_3$) δ 10.06 (s, 1H) 9.59 (d, 1H), 7.81 (d, 2H), 7.62 (d, 1H), 7.03 (m, 3H), 3.89 (s, 3H); MS m/z 287 (M+1).

c) 1-[8-Chloro-2-(4-methoxyphenyl)imidazo[1,2-α]pyridin-3-yl]-2-propyn-1-one.

In a similar manner as described in Example 2, from 8-chloro-2-(4-methoxyphenyl)imidazo[1,2-α]pyridine-3-carbaldehyde (4 g, 14 mmol) was obtained 1-[8-chloro-2-(4-methoxyphenyl)imidazo[1,2-α]pyridin-3-yl]-2-propyn-1-one (2.2 g, 51% for 2 steps) as a white solid. $^1$H NMR (CDCl$_3$) δ 9.67 (d, 1H), 7.68 (m, 3H), 7.08 (t, 1H), 6.97 (d, 2H), 3.88 (s, 3H), 2.90 (s, 1H); MS m/z 311 (M+1).

d) 4-[8-Chloro-2-(4-methoxyphenyl)imidazo[1,2-α]pyridin-3-yl]-N-cyclopentyl-2-pyrimidinamine.

In a similar manner as described in Example 2, from 1-[8-chloro-2-(4-methoxyphenyl)imidazo[1,2-α]pyridin-3-yl]-2-propyn-1-one (1.6 g, 5.2 mmol), cyclopentyl guanidine hydrochloride (1.26 g, 7.7 mmol) and potassium carbonate (1.26 g, 7.7 mmol) was obtained 4-[8-chloro-2-(4-methoxyphenyl)imidazo[1,2-α]pyridin-3-yl]-N-cyclopentyl-2-pyrimidinamine (1.1 g, 50%) as a white solid. $^1$H NMR (CDCl$_3$) δ 9.52 (d, 1H), 8.10 (d, 1H), 7.62 (d, 2H), 7.39 (d, 1H), 6.95 (d, 2H), 6.83 (t, 1H), 6.47 (d, 1H), 5.24 (d, 1H), 4.35 (m, 1H), 3.86 (s, 3H), 2.0–2.1 (m, 2H), 1.4–1.9 (m, 6H); MS m/z 420 (M+1).

EXAMPLE 10

N-Cyclopentyl-3-[2-(cyclopentylamino)-4-pyrimidinyl]-2-(4-methoxyphenyl)imidazo[1,2-α]pyridin-8-amine

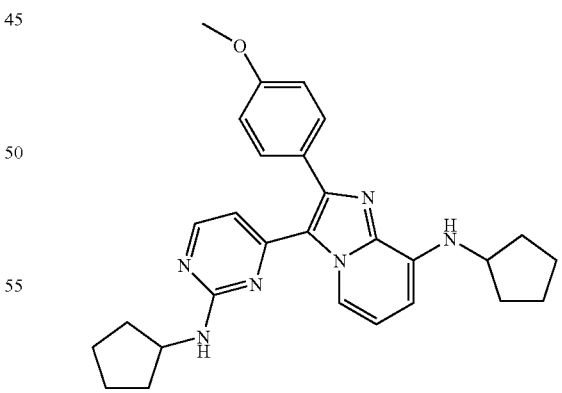

In a similar manner as described in Example 3, from 4-[8-chloro-2-(4-methoxyphenyl)imidazo[1,2-α]pyridin-3-yl]-N-cyclopentyl-2-pyrimidinamine (670 mg, 1.6 mmol) and cyclopentylamine (10 mL) was obtained N-cyclopentyl-3-[2-(cyclopentylamino)-4-pyrimidinyl]-2-(4-methoxyphenyl)imidazo[1,2-α]pyridin-8-amine (397 mg, 53%) as a solid. $^1$H NMR (CDCl$_3$) δ 8.86 (d, 1H), 8.04 (d, 1H), 7.57 (d, 2H), 6.94 (d, 2H), 6.76 (t, 1H), 6.40 (d, 1H), 6.28 (d, 1H), 5.27 (d, 1H), 5.17 (d, 1H), 4.36 (m, 1H), 3.91 (m, 1H), 3.86 (s, 3H), 2.0–2.1 (m, 4H), 1.4–1.9 (m, 12H); MS m/z 469 (M+1).

EXAMPLE 11

4-{8-(Cyclopentylamino)-3-[2-(cyclopentylamino)-4-pyrimidinyl]imidazo[1,2-α]pyridin-2-yl}phenol

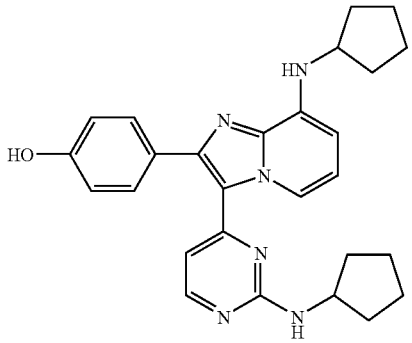

To a solution of N-cyclopentyl-3-[2-(cyclopentylamino)-4-pyrimidinyl]-2-(4-methoxyphenyl)imidazo[1,2-α]pyridin-8-amine (0.4 g, 0.9 mmol) in dichloromethane (10 mL) at −78° C. was added boron tribromide (2.6 mL, 1.0 M in dichloromethane, 2.6 mmol) dropwise. The resulting solution was allowed to warm to room temperature. After stirring for 15 hours at room temperature, the mixture was cooled to 0° C. and quenched by the addition of water and aqueous sodium bicarbonate. The mixture was extracted with ethyl acetate. The organic phase was dried (magnesium sulfate), filtered and concentrated to give a solid residue which was purified by silica gel chromatography (95:5 chloroform-methanol) to give 4-{8-(cyclopentylamino)-3-[2-(cyclopentylamino)-4-pyrimidinyl]imidazo[1,2-α]pyridin-2-yl}phenol as a solid (280 mg, 70%). $^1$H NMR (DMSO-d$_6$): δ 9.63 (s, 1H), 8.86 (broad s, 1H), 8.07 (d, 1H), 7.37 (d, 2H), 7.30 (d, 1H), 6.80 (m, 3H), 6.30 (m, 2H), 5.60 (d, 1H), 4.19 (m, 1H), 3.89 (m, 1H), 1.9–2.1 (m, 4H), 1.4–1.9 (m, 12H); MS m/z 455 (M+1).

EXAMPLE 12

8-Chloro-2-(4-fluorophenyl)-3-(2-fluoro-4-pyridinyl)imidazo[1,2-α]pyridine

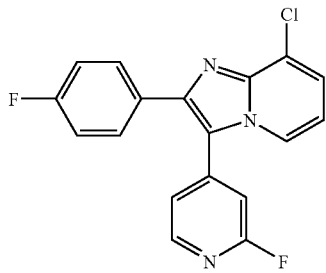

a) 8-Chloro-2-(4-fluorophenyl)-3-iodoimidazo[1,2-α]pyridine.

8-Chloro-2-(4-fluorophenyl)imidazo[1,2-α]pyridine (2 g, 8.1 mmol) was dissolved in dichloromethane (30 mL). To this solution was added N-iodosuccinimide (2.7 g, 12.1 mmol) and the resulting mixture stirred at room temperature overnight. Additional dichloromethane was added to the reaction mixture and this solution was extracted with 1 M sodium hydroxide (2×60 mL) and water, dried (magnesium sulfate), filtered and concentrated to a solid. Recrystallization from acetonitrile gave 8-chloro-2-(4-fluorophenyl)-3-iodoimidazo[1,2-α]pyridine (2.4 g, 80%) as a white solid. $^1$H NMR (CDCl$_3$): δ 8.22 (d, 1H), 8.11 (q, 2H), 7.41 (d, 1H), 7.20 (t, 2H), 6.94 (t, 1H); $^{19}$F NMR (CDCl$_3$) δ −113.2; MS m/z 373 (M+1).

b) 2-Fluoropyridin-4-ylboronic acid.

To a stirred solution of n-butyl lithium (3.2 mL, 2.5M, 8.0 mmol) in dry diethyl ether (20 mL) at −78° C. was added a solution of 2-fluoro-4-iodopyridine (1.5 g, 6.7 mmol) in dry ether (10 mL) and the reaction mixture was stirred at −78° C. for 10 minutes. Tributyl borate (2.4 mL, 2.01 g, 8.7 mmol) was added and the reaction mixture was allowed to warm to room temperature over 2 hours. Water (5 mL) was added followed by 2N aqueous sodium hydroxide solution (10 mL) to dissolve the solids. The organic phase was separated. The aqueous phase was acidified to pH 3 using 6N hydrochloric acid and the resulting white solid was collected by filtration and dried under vacuum to give the title compound, 0.74 g (78%). $^1$H NMR (DMSO-d$_6$) δ 8.65 (br s, 2H), 8.21 (d, 1H), 7.59 (t, 1H), 7.37 (d, 1H).

c) 8-Chloro-2-(4-fluorophenyl)-3-(2-fluoro-4-pyridinyl)imidazo[1,2-α]pyridine.

8-Chloro-2-(4-fluorophenyl)-3-iodoimidazo[1,2-α]pyridine (0.15 g, 0.4 mmol) was dissolved in N,N-dimethylformamide (5 mL). To this solution was added 2-fluoro-4-pyridinylboronic acid (120 mg, 0.8 mmol), dichlorobis(triphenylphosphine)palladium (II) (60 mg, 0.08 mmol) and aqueous sodium carbonate (170 mg, 1.6 mmol). The resulting solution was heated at 100° C. overnight. Water was added to the reaction mixture and the mixture was extracted with ethyl acetate. The organic phase was dried (magnesium sulfate), filtered and concentrated to a solid. Purification by silca gel chromatography (1:1 ethyl acetate:hexane) gave 8-chloro-2-(4-fluorophenyl)-3-(2-fluoropyridin-4-yl)imidazo[1,2-α]pyridine (110 mg, 81%) as a white solid. $^1$H NMR (CDCl$_3$): δ 8.41 (d, 1H), 8.09 (d, 1H), 7.62 (q, 2H), 7.42 (d, 1H), 7.29 (d, 1H), 7.07 (m, 3H), 6.87 (t, 1H); $^{19}$F NMR (CDCl$_3$) δ −65.46 and −112.94; MS m/z 342 (M+1).

EXAMPLE 13

4-[8-Chloro-2-(4-fluorophenyl)imidazo[1,2-α]pyridin-3-yl]-N-cyclopentyl-2-pyridinamine

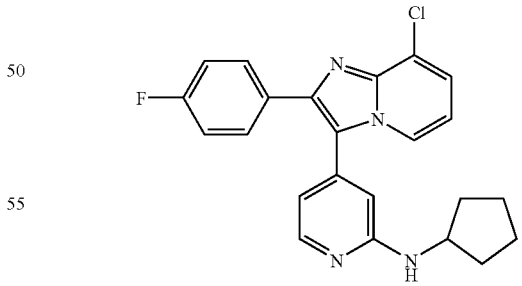

8-Chloro-2-(4-fluorophenyl)-3-(2-fluoro-4-pyridinyl)imidazo[1,2-α]pyridine (0.10 g, 0.29 mmol) was dissolved in cyclopentylamine (5 mL). This solution was heated in a glass tube at 150° C. for 72 hours. Ethyl acetate and water were added to the reaction mixture and the phases were separated. The organic phase was washed with water, dried (magnesium sulfate), filtered and concentrated to a solid. This solid was purified by silica gel chromatography (1:1 ethyl acetate:hexane) to give 4-[8-chloro-2-(4-fluorophenyl)

imidazo[1,2-α]pyridin-3-yl]-N-cyclopentyl-2-pyridinamine (90 mg, 76%) as a white foam. $^1$H NMR (CDCl$_3$): δ 8.26 (d, 1H), 8.06 (d, 1H), 7.73 (q, 2H), 7.34 (d, 1H), 7.05 (t, 2H), 6.77 (t, 1H), 6.65 (dd, 1H), 6.4 (s, 1H), 4.85 (d, 1H), 3.92 (m, 1H), 2.0–1.4 (m, 8H); $^{19}$F NMR (CDCl$_3$) δ –114.07; MS m/z 407 (M+1).

EXAMPLE 14

N-Cyclopentyl-3-[2-(cyclopentylamino)-4-pyridinyl]-2-(4-fluorophenyl)imidazo[1,2-α]pyridin-8-amine

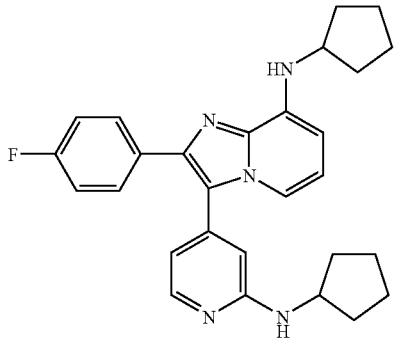

In a similar manner as described in Example 3, from 4-[8-chloro-2-(4-fluorophenyl)imidazo[1,2-α]pyridin-3-yl]-N-cyclopentyl-2-pyridinamine (80 mg, 0.2 mmol) and cyclopentylamine was obtained, after silica gel chromatography (1:1 ethyl acetate:hexane) N-cyclopentyl-3-[2-(cyclopentylamino)-4-pyridinyl]-2-(4-fluorophenyl)imidazo[1,2-α]pyridin-8-amine (25 mg, 27%) as a solid. $^1$H NMR (CDCl$_3$): δ 8.21 (d, 1H), 7.67 (q, 2H), 7.52 (d, 1H), 7.05 (t, 2H), 6.69 (d, 1H), 6.65 (d, 1H), 6.41 (s, 1H), 6.19 (d, 1H), 5.34 (d, 1H), 4.72 (d, 1H), 4.00–3.8 (m, 2H), 1.3–2.2 (m, 16H); $^{19}$F NMR (CDCl$_3$) δ –115.10; MS m/z 457 (M+1).

EXAMPLE 15

4-[8-Chloro-2-(3-methoxyphenyl)imidazo[1,2-α]pyridin-3-yl]-N-cyclopentyl-2-pyrimidinamine

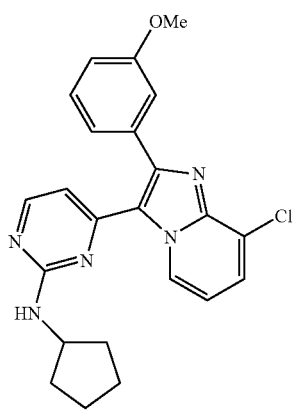

a) 8-Chloro-2-(3-methoxyphenyl)imidazo[1,2-α]pyridine.

In a similar manner as described in Example 2 from 3-chloro-2-pyridinamine (4.8 g, 37.4 mmol) and 2-bromo-1-(3-methoxyphenyl)ethanone (8.56 g, 37.4 mmol) was obtained 8-chloro-2-(3-methoxyphenyl)imidazo[1,2-α]pyridine (6.7 g, 70%) as a tan powder. $^1$H NMR (CDCl$_3$): δ 8.03 (d, 1H), 7.89 (s, 1H), 7.57–7.52 (m, 2H), 7.33 (t, 1H), 7.23 (d, 1H), 6.89 (dd, 1H), 6.71 (t, 1H), 3.89 (s, 3H); $^{13}$C NMR (CDCl$_3$): δ 159.94, 146.31, 142.96, 134.61, 129.65, 124.30, 123.58, 123.26, 118.81, 114.33, 112.02, 111.44, 109.91, 55.39; MS m/z 259 (M+1); Anal. Calcd for C$_{14}$H$_{11}$ClN$_2$O: C, 64.93; H, 4.29; N, 10.83. Found: C, 64.58; H, 4.51; N, 10.52.

b) 8-Chloro-2-(3-methoxyphenyl)imidazo[1,2-α]pyridine-3-carbaldehyde.

In a similar manner as described in Example 2 from 8-chloro-2-(3-methoxyphenyl)imidazo[1,2-α]pyridine (2.0 g, 7.75 mmol) and phosphorous oxychloride (1.08 mL, 11.62 mmol) in N,N-dimethylformamide (30 mL) was formed 8-chloro-2-(3-methoxyphenyl)imidazo[1,2-α]pyridine-3-carbaldehyde (2.2 g, 99%) as a white solid. $^1$H NMR (CDCl$_3$): δ 10.09 (s, 1H), 9.60 (d, 1H), 7.64 (d, 1H), 7.45–7.37 (m, 3H), 7.09–7.05 (m, 2H), 3.90 (s, 3H); MS m/z 287 (M+1); Anal. Calcd. for C$_{15}$H$_{11}$ClN$_2$O$_2$: C, 62.84; H, 3.87; N, 9.77. Found: C, 62.79; H, 3.92; N, 9.64.

c) 1-[8-Chloro-2-(3-methoxyphenyl)imidazo[1,2-α]pyridin-3-yl]-2-propyn-1-ol.

In a similar manner as described in Example 2 from 8-chloro-2-(3-methoxyphenyl)imidazo[1,2-α]pyridine-3-carbaldehyde (1.06 g, 3.70 mmol) and ethynyl magnesium bromide (18.53 mL, 0.5 M in tetrahydrofuran, 9.26 mmol) was formed 1-[8-chloro-2-(3-methoxyphenyl)imidazo[1,2-α]pyridin-3-yl]-2-propyn-1-ol (910 mg, 79%) as a white solid. $^1$H NMR (CDCl$_3$): δ 8.61 (d, 1H), 7.33–7.26 (m, 2H), 7.16–7.11 (m, 2H), 6.88 (m, 1H), 6.79 (m, 1H), 6.14 (m, 1H), 3.85 (s, 3H), 3.27 (broad, 1H), 2.64 (d, 1H); $^{13}$C NMR (CDCl$_3$): δ 159.64, 144.46, 134.12, 129.56, 124.99, 124.51, 123.03, 121.37, 119.43, 114.54, 114.13, 111.81, 111.27, 79.96, 75.03, 55.88, 55.38; MS m/z 313 (M+1); Anal. Calcd. for C$_{17}$H$_{13}$ClN$_2$O$_2$: C, 65.29; H, 4.19; N, 8.96. Found: C, 65.23; H, 4.34; N, 8.81.

d) 1-[8-Chloro-2-(3-methoxyphenyl)imidazo[1,2-α]pyridin-3-yl]-2-propyn-1-one.

In a similar manner as described in Example 2 from 1-[8-chloro-2-(3-methoxyphenyl)imidazo[1,2-α]pyridin-3-yl]-2-propyn-1-ol (870 mg, 2.78 mmol) was formed 1-[8-chloro-2-(3-methoxyphenyl)imidazo[1,2-α]pyridin-3-yl]-2-propyn-1-one (680 mg, 78%) as a golden foam. $^1$H NMR (CDCl$_3$): δ 9.66 (d, 1H), 7.65 (d, 1H), 7.34 (t, 1H), 7.28–7.22 (m, 2H), 7.10 (t, 1H), 7.02 (m, 1H), 3.86 (s, 3H), 2.86 (s, 1H); MS m/z 311 (M+1).

e) 4-[8-Chloro-2-(3-methoxyphenyl)imidazo[1,2-α]pyridin-3-yl]-N-cyclopentyl-2-pyrimidinamine.

In a similar manner as described in Example 2 from 1-[8-chloro-2-(3-methoxyphenyl)imidazo[1,2-α]pyridin-3-yl]-2-propyn-1-one (530 mg, 1.70 mmol), N-cyclopentyl guanidine hydrochloride (557 mg, 3.41 mmol) and potassium carbonate in ethanol was formed 4-[8-chloro-2-(3-methoxyphenyl)imidazo[1,2-α]pyridin-3-yl]-N-cyclopentyl-2-pyrimidinamine (390 mg, 55%) as a white solid. $^1$H NMR (CDCl$_3$): δ 9.53 (broad, 1H), 8.10 (d, 1H), 7.40 (d, 1H), 7.31 (t, 1H), 7.26–7.21 (m, 2H), 6.94 (m, 1H), 6.85 (t, 1H), 6.44 (d, 1H), 5.18 (d, 1H), 4.33 (m, 1H), 3.82 (s, 3H), 2.14–2.07 (m, 2H), 1.82–1.74 (m, 2H), 1.72–1.64 (m, 2H), 1.63–1.54 (m, 2H); $^{13}$C NMR (CDCl$_3$): δ 1161.79, 159.68, 157.90, 157.70, 148.82, 143.61, 135.54, 129.61, 126.08, 125.30, 123.18, 122.21, 114.93, 114.61, 112.43, 111.27, 110.04, 55.39, 53.06, 33.54, 23.81; MS m/z 420 (M+1); Anal. Calcd. for C$_{23}$H$_{22}$ClN$_5$O: C, 65.79; H, 5.28; N, 16.68. Found: C, 65.78; H, 5.09; N, 16.70.

EXAMPLE 16

N-Cyclopentyl-3-[2-(cyclopentylamino)-4-pyrimidinyl]-2-(3-methoxyphenyl)imidazo[1,2-α]pyridin-8-amine

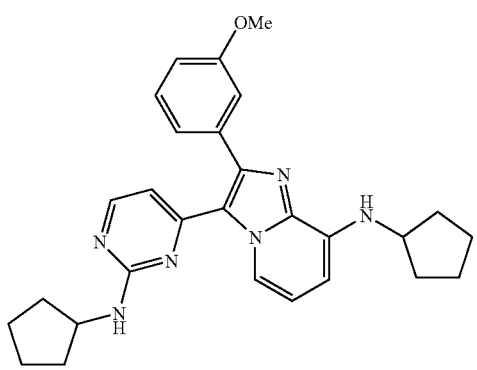

In a similar manner as described in Example 3 from 4-[8-chloro-2-(3-methoxyphenyl)imidazo[1,2-α]pyridin-3-yl]-N-cyclopentyl-2-pyrimidinamine (162 mg, 0.39 mmol) and cyclopentylamine was formed N-cyclopentyl-3-[2-(cyclopentylamino)-4-pyrimidinyl]-2-(3-methoxyphenyl)imidazo[1,2-α]pyridin-8-amine (55 mg, 31%) as a white solid. $^1$H NMR (CDCl$_3$): δ 8.90 (m, 1H), 8.08 (d, 1H), 7.37–7.22 (m, 2H), 6.96 (m, 1H), 6.79 (t, 1H), 6.43 (d, 1H), 6.30 (d, 1H), 5.40 (d, 1H), 5.31 (d, 1H), 4.37 (m, 1H), 3.94 (m, 1H), 3.85 (s, 3H), 2.14–2.07 (m, 4H), 1.82–1.56 (m, 12H); MS m/z 469 (M+1).

EXAMPLE 17

3-{8-(Cyclopentylamino)-3-[2-(cyclopentylamino)-4-pyrimidinyl]imidazo[1,2-α]pyridin-2-yl}phenol

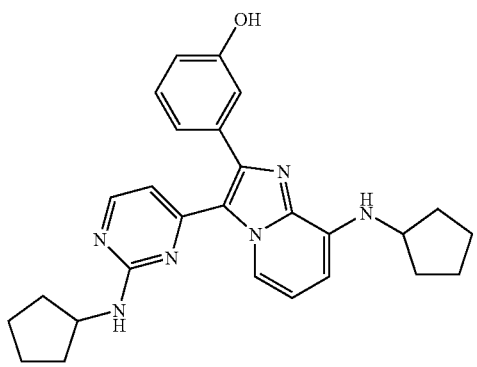

To a cold (−78° C.) solution of formed N-cyclopentyl-3-[2-(cyclopentylamino)-4-pyrimidinyl]-2-(3-methoxyphenyl)imidazo[1,2-α]pyridin-8-amine (42 mg, 0.09 mmol) in dichloromethane (5 mL) was added boron tribromide (0.5 mL, 1 M in dichloromethane, 0.5 mmol) dropwise. The solution was allowed to warm to room temperature over 4 hours and stirred for an additional 16 hours. The reaction was quenched by the addition of methanol followed by saturated aqueous sodium bicarbonate. Ether was added and the layers separated. The organic layer was washed with brine. The aqueous layer was extracted with ether and the combined organics were dried over magnesium sulfate. Filtration and concentration followed by flash chromatography (1:1 hexanes:ethyl acetate) provided 3-{8-(cyclopentylamino)-3-[2-(cyclopentylamino)-4-pyrimidinyl]imidazo[1,2-α]pyridin-2-yl}phenol (30 mg, 73%) as a yellow solid. $^1$H NMR (CDCl$_3$): δ 8.90 (broad, 1H), 7.96 (d, 1H), 7.31 (s, 1H), 7.17 (t, 1H), 7.01 (d, 1H), 6.81–6.75 (m, 2H), 6.38 (d, 1H), 6.27 (d, 1H), 5.53 (d, 1H), 5.28 (d, 1H), 4.30 (m, 1H), 3.88 (m, 1H), 2.10–1.93 (m, 4H), 1.78–1.48 (m, 12H); MS m/z 455 (M+1).

EXAMPLE 18

2-[3-(Allyloxy)phenyl]-N-cyclopentyl-3-[2-(cyclopentylamino)-4-pyrimidinyl]imidazo[1,2-α]pyridin-8-amine

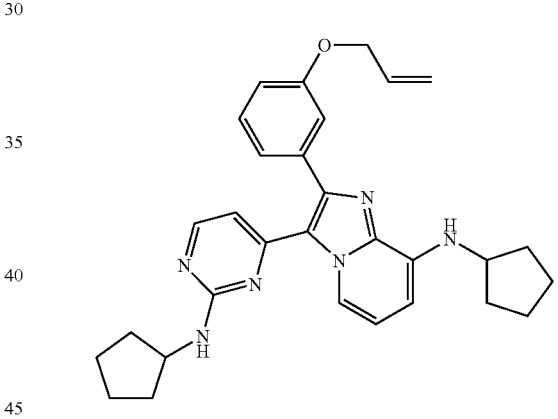

To a solution of 3-{8-(cyclopentylamino)-3-[2-(cyclopentylamino)-4-pyrimidinyl]imidazo[1,2-α]pyridin-2-yl}phenol (12 mg, 0.03 mmol) in N,N-dimethylformamide was added cesium carbonate (11 mg, 0.04 mmol) followed by allyl bromide (0.1 mL, 1.15 mmol). The resulting mixture was stirred at room temperature for 5 hours. Ether was added followed by water. The organic layer was washed with brine. The aqueous layer was extracted with ether and the combined organics were dried over magnesium sulfate. Filtration and concentration followed by flash chromatography (2:1 hexanes:ethyl acetate) provided 2-[3-(allyloxy)phenyl]-N-cyclopentyl-3-[2-(cyclopentylamino)-4-pyrimidinyl]imidazo[1,2-α]pyridin-8-amine (10 mg, 77%) as an oil. $^1$H NMR (CDCl$_3$): δ 8.87 (broad, 1H), 8.01 (d, 1H), 7.30 (t, 1H), 7.20–7.17 (m, 2H), 6.95 (m, 1H), 6.78 (t, 1H), 6.38 (d, 1H), 6.28 (d, 1H), 6.03 (m, 1H), 30 5.43–5.24 (m, 4H), 4.54 (d, 2H), 4.34 (m, 1H), 3.91 (m, 1H), 2.12–2.04 (m, 4H), 1.82–1.55 (m, 12H); MS m/z 495 (M+1). This material was treated with anhydrous hydrochloric acid in ether to provide the corresponding hydrochoride salt as a yellow solid.

EXAMPLE 19

4-[8-Chloro-2-(4-methylphenyl)imidazo[1,2-α]pyridin-3-yl]-N-cyclopentyl-2-pyrimidinamine.

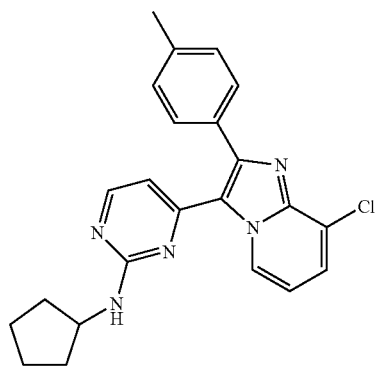

a) 8-Chloro-2-(4-methylphenyl)imidazo[1,2-α]pyridine.

In a similar manner as described in Example 2 from 2-bromo-1-(4-methylphenyl)ethanone (3.5 g, 16.4 mmol) and 3-chloro-2-pyridinamine (2.1 g, 16.4 mmol) was formed 8-chloro-2-(4-methylphenyl)imidazo[1,2-α]pyridine (4 g, 99%) as a white solid. $^1$H NMR (CDCl$_3$): δ 8.06 (d, 1H), 7.90 (d, 2H), 7.89 (s, 1H), 7.26 (d, 2H), 7.24 (d, 1H), 6.72 (t, 1H), 2.40 (s, 3H); MS m/z 243 (M+1).

b) 8-Chloro-2-(4-methylphenyl)imidazo[1,2-α]pyridine-3-carbaldehyde.

In a similar manner as described in Example 2 from 8-chloro-2-(4-methylphenyl)imidazo[1,2-α]pyridine (4 g, 16.4 mmol) and phosphorous oxychloride (2.29 mL, 24.6 mmol) in N,N-dimethylformamide (50 mL) was formed 8-chloro-2-(4-methylphenyl)imidazo[1,2-α]pyridine-3-carbaldehyde (1.7 g, 38%) as a white solid. $^1$H NMR (CDCl$_3$): δ 10.09 (s, 1H), 9.61 (d, 1H), 7.77 (d, 2H), 7.64 (d, 1H), 7.35 (d, 2H), 7.06 (t, 1H), 2.46 (s, 3H); $^{13}$C NMR (CDCl$_3$): δ 180.07, 158.51, 145.16, 140.34, 129.93, 129.62, 129.15, 129.01, 127.26, 123.40, 121.69, 114.81, 21.42; MS m/z 271 (M+1).

c) 1-[8-Chloro-2-(4-methyl phenyl)imidazo[1,2-α]pyridin-3-yl]-2-propyn-1-ol.

In a similar manner as described in Example 2 from 8-chloro-2-(4-methylphenyl)imidazo[1,2-α]pyridine-3-carbaldehyde (1.04 g, 3.85 mmol) and ethynyl magnesium bromide (19.25 mL, 0.5 M in tetrahydrofuran, 9.62 mmol) was formed 1-[8-chloro-2-(4-methylphenyl)imidazo[1,2-α]pyridin-3-yl]-2-propyn-1-ol (1.1 g, 99%) as a white solid. $^1$H NMR (CDCl$_3$): δ 8.57 (d, 1H), 7.37 (d, 2H), 7.26 (m, 1H), 7.10 (d, 2H), 6.75 (t, 1H), 6.10 (d, 1H), 3.71 (broad, 1H), 2.62 (d, 1H), 2.33 (s, 3H); MS m/z 297 (M+1).

d) 1-[8-Chloro-2-(4-methylphenyl)imidazo[1,2-α]pyridin-3-yl]-2-propyn-1-one.

In a similar manner as described in Example 2 from 1-[8-chloro-2-(4-methylphenyl)imidazo[1,2-α]pyridin-3-yl]-2-propyn-1-ol (1.10 g, 3.71 mmol) was formed 1-[8-chloro-2-(4-methylphenyl)imidazo[1,2-α]pyridin-3-yl]-2-propyn-1-one (943 mg, 87%) as a brown solid. $^1$H NMR (CDCl$_3$): δ 9.68 (d, 1H), 7.67–7.61 (m, 3H), 7.27–7.07 (m, 3H), 2.86 (s, 1H), 2.44 (s, 3H); MS m/z 295 (M+1).

e) 4-[8-Chloro-2-(4-methylphenyl)imidazo[1,2-α]pyridin-3-yl]-N-cyclopentyl-2-pyrimidinamine.

In a similar manner as described in Example 2 from 1-[8-chloro-2-(4-methylphenyl)imidazo[1,2-α]pyridin-3-yl]-2-propyn-1-one (743 mg, 2.52 mmol), N-cyclopentyl guanidine hydrochloride (618 mg, 3.79 mmol) and potassium carbonate in ethanol was formed 4-[8-chloro-2-(4-methylphenyl)imidazo[1,2-α]pyridin-3-yl]-N-cyclopentyl-2-pyrimidinamine (513 mg, 51%) as a yellow solid. $^1$H NMR (CDCl$_3$): δ 9.51 (broad, 1H), 8.08 (d, 1H), 7.56 (d, 2H), 7.38 (d, 1H), 7.21 (d, 2H), 6.83 (t, 1H), 6.45 (d, 1H), 5.19 (d, 1H), 4.33 (m, 1H), 2.40 (s, 3H), 2.14–2.07 (m, 2H), 1.82–1.74 (m, 2H), 1.72–1.65 (m, 2H), 1.64–1.53 (m, 2H); $^{13}$C NMR (CDCl$_3$): δ 161.81, 157.91, 157.85, 149.12, 143.64, 138.64, 131.25, 129.52, 129.25, 125.97, 125.16, 123.08, 119.52, 112.26, 110.02, 53.06, 33.53, 23.80, 21.39; MS m/z 404 (M+1).

EXAMPLE 20

N-Cyclopentyl-3-[2-(cyclopentylamino)-4-pyrimidinyl]-2-(4-methylphenyl)imidazo[1,2-α]pyridin-8-amine.

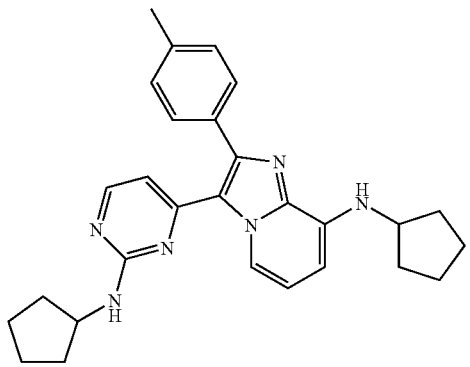

In a similar manner as described in Example 3 from 4-[8-chloro-2-(4-methylphenyl)imidazo[1,2-α]pyridin-3-yl]-N-cyclopentyl-2-pyrimidinamine (130 mg, 0.32 mmol) and cyclopentylamine was formed N-cyclopentyl-3-[2-(cyclopentylamino)-4-pyrimidinyl]-2-(4-methylphenyl)imidazo[1,2-α]pyridin-8-amine (110 mg, 76%) as a yellow solid. $^1$H NMR (CDCl$_3$): δ 8.86 (broad, 1H), 8.02 (d, 1H), 7.52 (d, 2H), 7.20 (d, 2H), 6.74 (t, 1H), 6.38 (d, 1H), 6.25 (d, 1H), 5.28–5.26 (m, 2H), 4.34 (m, 1H), 3.90 (m, 1H), 2.39 (s, 3H), 2.12–2.04 (m, 4H), 1.80–1.53 (m, 12H); $^{13}$C NMR (CDCl$_3$): δ 161.79, 158.57, 157.17, 146.77, 139.94, 138.08, 136.70, 132.14, 129.29, 129.24, 119.10, 115.25, 114.18, 109.70, 99.69, 54.22, 52.98, 33.48, 33.17, 24.16, 23.77, 21.32; MS m/z 453 (M+1).

EXAMPLE 21

3-[2-(Cyclopentylamino)-4-pyrimidinyl]-N-(2-methoxyethyl)-2-(4-methylphenyl)imidazo[1,2-α]pyridin-8-amine.

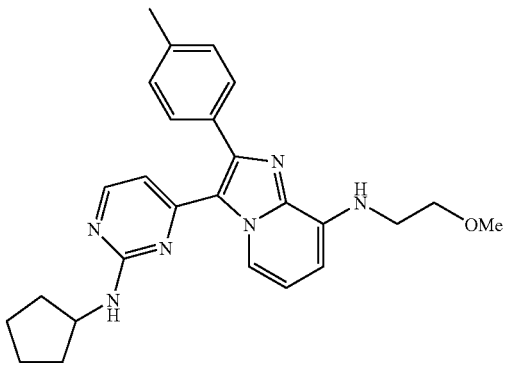

In a similar manner as described in Example 3 from 4-[8-chloro-2-(4-methylphenyl)imidazo[1,2-α]pyridin-3-yl]-N-cyclopentyl-2-pyrimidinamine (128 mg, 0.32 mmol) and 2-methoxyethylamine was formed 3-[2-(cyclopentylamino)-4-pyrimidinyl]-N-(2-methoxyethyl)-2-(4-methylphenyl)imidazo[1,2-α]pyridin-8-amine (37 mg, 30%) as a yellow solid. $^1$H NMR (CDCl$_3$): δ 8.88 (broad, 1H), 8.03 (d, 1H), 7.52 (d, 2H), 7.20 (d, 2H), 6.75 (t, 1H), 6.40 (d, 1H), 6.26 (d, 1H), 5.48 (m, 1H), 5.21 (d, 1H), 4.34 (m, 1H), 3.68 (m, 2H), 3.45 (m, 2H), 3.40 (s, 3H), 2.39 (s, 3H), 2.14–2.06 (m, 2H), 1.80–1.54 (m, 6H); MS m/z 443 (M+1).

EXAMPLE 22

N-Cyclopentyl-4-[2-(4-methylphenyl)-8-(4-morpholinyl)imidazo[1,2-α]pyridin-3-yl]-2-pyrimidinamine.

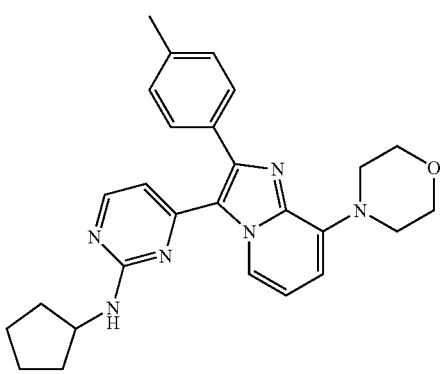

In a similar manner as described in Example 3 from 4-[8-chloro-2-(4-methylphenyl)imidazo[1,2-α]pyridin-3-yl]-N-cyclopentyl-2-pyrimidinamine (120 mg, 0.30 mmol) and morpholine was formed N-cyclopentyl-4-[2-(4-methylphenyl)-8-(4-morpholinyl)imidazo[1,2-α]pyridin-3-yl]-2-pyrimidinamine (89 mg, 66%) as a yellow solid. $^1$H NMR (CDCl$_3$): δ 9.11 (broad, 1H), 8.07 (d, 1H), 7.57 (d, 2H), 7.19 (d, 2H), 6.77 (t, 1H), 6.56 (d, 1H), 6.45 (d, 1H), 5.26 (broad, 1H), 4.34 (m, 1H), 3.97 (m, 4H), 3.56 (m, 4H), 2.38 (s, 3H), 2.13–2.06 (m, 2H), 1.80–1.51 (m, 6H); MS m/z 455 (M+1).

EXAMPLE 23

4-[8-Chloro-2-(2-naphthyl)imidazo[1,2-α]pyridin-3-yl]-N-cyclopropyl-2-pyrimidinamine.

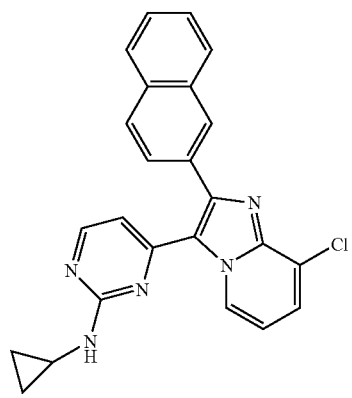

a) 8-Chloro-2-(2-naphthyl)imidazo[1,2-α]pyridine.

In a similar manner as described in Example 2 from 2-bromo-1-(2-naphthyl)ethanone (2.7 g, 21.0 mmol) and 3-chloro-2-pyridinamine (5.23 g, 21.0 mmol) was formed 8-chloro-2-(2-naphthyl)imidazo[1,2-α]pyridine (3.18 g, 54%) was a tan solid. $^1$H NMR (DMSO-d$_6$): δ 8.65 (s, 1H), 8.55 (m, 2H), 8.09 (dd, 1H), 8.03–7.90 (m, 3H), 7.54–7.44 (m, 3H), 6.90 (t, 1H); $^{13}$C NMR (DMSO-d$_6$): δ 145.34, 142.84, 133.92, 133.45, 131.47, 129.01, 128.89, 128.33, 127.19, 126.93, 126.83, 124.99, 124.84, 124.74, 121.82, 112.86, 112.39; MS m/z 279 (M+1); Anal. Calcd. for C$_{17}$H$_{11}$ClN$_2$: C, 73.25; H, 3.98; N, 10.05. Found: C, 72.98; H, 3.97; N, 9.92.

b) 8-Chloro-2-(2-naphthyl)imidazo[1,2-α]pyridine-3-carbaldehyde.

In a similar manner as described in Example 2 from 8-chloro-2-(2-naphthyl)imidazo[1,2-α]pyridine (1.75 g, 6.3 mmol) and phosphorous oxychloride (0.88 mL, 9.4 mmol) in N,N-dimethylformamide (15 mL) was formed 8-chloro-2-(2-naphthyl)imidazo[1,2-α]pyridine-3-carbaldehyde (1.92 g, 99%) as a white solid. $^1$H NMR (CDCl$_3$): δ 10.18 (s, 1H), 9.63 (d, 1H), 8.33 (s, 1H), 8.02–7.91 (m, 4H), 7.66 (d, 1H), 7.59–7.55 (m, 2H), 7.08 (t, 1H); $^{13}$C NMR (CDCl$_3$): δ 180.17, 158.30, 145.27, 133.90, 133.10, 130.13, 129.29, 129.24, 128.76, 128.66, 127.82, 127.30, 126.82, 126.80, 123.54, 122.03, 115.00; MS m/z 307 (M+1); Anal. Calcd. for C$_{18}$H$_{11}$ClN$_2$O.1H$_2$O: C, 66.66; H, 3.39; N, 8.64. Found: C, 66.32; H, 3.63; N, 8.76.

c) 1-[8-Chloro-2-(2-naphthyl)imidazo[1,2-α]pyridin-3-yl]-2-propyn-1-ol.

In a similar manner as described in Example 2 from 8-chloro-2-(2-naphthyl)imidazo[1,2-α]pyridine-3-carbaldehyde (1.05 g, 3.42 mmol) and ethynyl magnesium bromide (17.1 mL, 0.5 M in tetrahydrofuran, 8.55 mmol) was formed 1-[8-chloro-2-(2-naphthyl)imidazo[1,2-α]pyridin-3-yl]-2- propyn-1-ol (1.1 g, 99%) as a white solid. $^1$H NMR (DMSO-$d_6$): δ 8.71 (d, 1H), 8.23 (s, 1H), 8.07–8.03 (m, 2H), 7.97 (m, 1H), 7.87 (dd, 1H), 7.61–7.56 (m, 3H), 7.08 (t, 1H), 6.59 (d, 1H), 6.10 (dd, 1H), 3.67 (d, 1H); MS m/z 333 (M+1).

d) 1-[8-Chloro-2-(2-naphthyl)imidazo[1,2-α]pyridin-3-yl]-2-propyn-1-one.

In a similar manner as described in Example 2 from 1-[8-chloro-2-(2-naphthyl)imidazo[1,2-α]pyridin-3-yl]-2-propyn-1-ol (1.11 g, 3.34 mmol) was formed 1-[8-chloro-2-(2-naphthyl)imidazo[1,2-α]pyridin-3-yl]-2-propyn-1-one (800 mg, 72%) as a solid. $^1$H NMR (CDCl$_3$): δ 9.72 (d, 1H), 8.25 (s, 1H), 7.94–7.82 (m, 4H), 7.69 (d, 1H), 7.55 (m, 2H), 7.13 (t, 1H), 2.68 (s, 1H); MS m/z 331 (M+1).

e) 4-[8-Chloro-2-(2-naphthyl)imidazo[1,2-α]pyridin-3-yl]-N-cyclopropyl-2-pyrimidinamine.

In a similar manner as described in Example 2 from 1-[8-chloro-2-(2-naphthyl)imidazo[1,2-α]pyridin-3-yl]-2-propyn-1-one (800 mg, 2.42 mmol), N-cyclopropyl guanidine sulfate (711 mg, 2.42 mmol) and potassium carbonate in ethanol was formed 4-[8-chloro-2-(2-naphthyl)imidazo[1, 2-α]pyridin-3-yl]-N-cyclopropyl-2-pyrimidinamine (170 mg, 17%) as a yellow solid. $^1$H NMR (CDCl$_3$): δ 9.87 (broad, 1H), 8.29 (s, 1H), 8.10 (d, 1H), 7.93–7.88 (m, 3H), 7.76 (m, 1H), 7.58–7.52 (m, 2H), 7.46 (d, 1H), 6.90 (t, 1H), 6.52 (d, 1H), 5.71 (broad, 1H), 2.90 (m, 1H), 0.96–0.90 (m, 2H), 0.73–0.69 (m, 2H); MS m/z 412 (M+1).

EXAMPLE 24

N-Cyclopropyl-3-[2-(cyclopropylamino)-4-pyrimidinyl]-2-(2-naphthyl)imidazo[1,2-α]pyridin-8-amine.

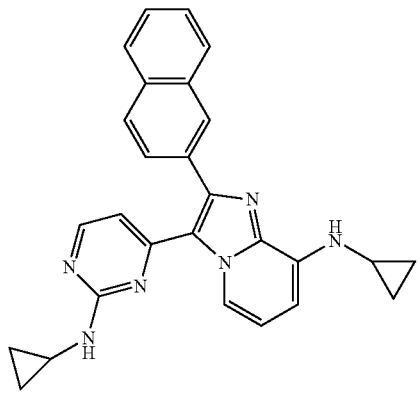

In a similar manner as described in Example 3 from 4-[8-chloro-2-(2-naphthyl)imidazo[1,2-α]pyridin-3-yl]-N-cyclopropyl-2-pyrimidinamine (83 mg, 0.20 mmol) and cyclopropylamine was formed N-cyclopropyl-3-[2-(cyclopropylamino)-4-pyrimidinyl]-2-(2-naphthyl)imidazo[1,2-α]pyridin-8-amine (25 mg, 30%) as a white solid. $^1$H NMR (CDCl$_3$): δ 9.19 (broad, 1H), 8.17 (s, 1H), 8.01 (d, 1H), 7.88–7.84 (m, 3H), 7.70 (d, 1H), 7.51–7.48 (m, 2H), 6.82 (t, 1H), 6.68 (d, 1H), 6.44 (d, 1H), 5.64 (s, 1H), 5.50 (s, 1H), 2.86 (m, 1H), 2.58 (m, 1H), 0.91–0.86 (m, 2H), 0.83–0.79 (m, 2H), 0.66 (m, 4H); $^{13}$C NMR (CDCl$_3$): δ 163.03, 158.41, 157.31, 147.00, 139.99, 137.51, 133.48, 133.20, 132.60, 128.62, 128.37, 128.18, 127.70, 127.25, 126.37, 126.20, 119.40, 116.73, 114.31, 110.34, 101.19, 24.48, 24.08, 7.44, 7.03; MS m/z 433 (M+1).

EXAMPLE 25

4-{8-Chloro-3-[2-(cyclopentylamino)-4-pyrimidinyl]imidazo[1,2-α]pyridin-2-yl}benzonitrile.

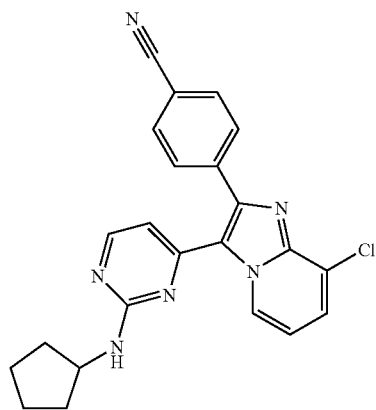

a) 4-(8-Chloroimidazo[1,2-α]pyridin-2-yl)benzonitrile.

In a similar manner as described in Example 2 from 4-(bromoacetyl)benzonitrile (3.68 g, 16.4 mmol) and 3-chloro-2-pyridinamine (2.1 g, 16.4 mmol) was formed 4-(8-chloroimidazo[1,2-α]pyridin-2-yl)benzonitrile (1.5 g, 36%) as a white solid. $^1$H NMR (CDCl$_3$): δ 8.09–8.07 (m, 3H), 7.99 (s, 1H), 7.69 (d, 2H), 7.29 (d, 1H), 6.77 (t, 1H); $^{13}$C NMR (CDCl$_3$): δ 144.23, 143.38, 137.64, 132.51, 126.65, 124.49, 124.33, 123.64, 118.95, 112.63, 111.42, 110.97; MS m/z 254 (M+1); Anal. Calcd. for $C_{14}H_8ClN_3 \cdot \frac{1}{3}H_2O$: C, 64.61; H, 3.07; N, 16.15. Found: C, 64.34; H, 3.02; N, 15.93.

b) 4-(8-Chloro-3-formylimidazo[1,2-α]pyridin-2-yl)benzonitrile.

In a similar manner as described in Example 2 from 4-(8-chloroimidazo[1,2-α]pyridin-2-yl)benzonitrile (1.47 g, 5.81 mmol) and phosphorous oxychloride (0.81 mL, 8.71 mmol) in N,N-dimethylformamide (15 mL) was formed 4-(8-chloro-3-formylimidazo[1,2-α]pyridin-2-yl)benzonitrile (1.63 g, 99%) as a white solid. $^1$H NMR (DMSO-$d_6$): δ 10.09 (s, 1H), 9.55 (d, 1H), 8.17 (d, 2H), 8.06 (d, 2H), 8.00 (d, 1H), 7.37 (t, 1H); $^{13}$C NMR (DMSO-$d_6$): δ 179.83, 153.83, 144.13, 136.27, 132.76, 130.52, 130.13, 127.29, 122.04, 121.88, 118.50, 116.31, 112.28; MS m/z 282 (M+1).

c) 4-[8-Chloro-3-(1-hydroxy-2-propynyl)imidazo[1,2-α]pyridin-2-yl]benzonitrile.

In a similar manner as described in Example 2 from 4-(8-chloro-3-formylimidazo[1,2-α]pyridin-2-yl)benzonitrile (830 mg, 2.95 mmol) and ethynyl magnesium bromide (7.08 mL, 0.5 M in tetrahydrofuran, 3.54 mmol) was formed 4-[8-chloro-3-(1-hydroxy-2-propynyl)imidazo[1,2-α]pyridin-2-yl]benzonitrile (910 mg, 99%) as a white solid. $^1$H NMR (DMSO-d₆): δ 8.71 (d, 1H), 7.99 (d, 2H), 7.93 (d, 2H), 7.63 (d, 1H), 7.10 (t, 1H), 6.62 (d, 1H), 6.04 (m, 1H), 3.68 (d, 1H); MS m/z 308 (M+1).

d) 4-(8-Chloro-3-propioloylimidazo[1,2-α]pyridin-2-yl)benzonitrile.

In a similar manner as described in Example 2 from 4-[8-chloro-3-(1-hydroxy-2-propynyl)imidazo[1,2-α]pyridin-2-yl]benzonitrile (832 mg, 2.71 mmol) was formed 4-(8-chloro-3-propioloylimidazo[1,2-α]pyridin-2-yl)benzonitrile (800 mg, 96%) as a brown solid. ¹H NMR (CDCl₃): δ 9.68 (d, 1H), 7.86 (d, 2H), 7.77 (d, 2H), 7.71 (d, 1H), 7.17 (m, 1H), 2.90 (m, 1H); MS m/z 306 (M+1).

e) 4-{8-Chloro-3-[2-(cyclopentylamino)-4-pyrimidinyl]imidazo[1,2-α]pyridin-2-yl}benzonitrile.

In a similar manner as described in Example 2 from 4-(8-chloro-3-propioloylimidazo[1,2-α]pyridin-2-yl)benzonitrile (690 mg, 2.26 mmol), N-cyclopentyl guanidine hydrochloride (553 mg, 3.39 mmol) and sodium ethoxide in ethanol was formed 4-{8-chloro-3-[2-(cyclopentylamino)-4-pyrimidinyl]imidazo[1,2-α]pyridin-2-yl}benzonitrile (300 mg, 32%) as a white solid. ¹H NMR (CDCl₃): δ 9.30 (broad, 1H), 8.17 (d, 1H), 7.84 (d, 2H), 7.69 (d, 2H), 7.43 (d, 1H), 6.88 (t, 1H), 6.37 (d, 1H), 5.25 (d, 1H), 4.32 (m, 1H), 2.15–2.06 (m, 2H), 1.80–1.53 (m, 6H); MS m/z 415 (M+1).

EXAMPLE 26

4-{8-(Cyclopentylamino)-3-[2-(cyclopentylamino)-4-pyrimidinyl]imidazo[1,2-α]pyridin-2-yl}benzonitrile.

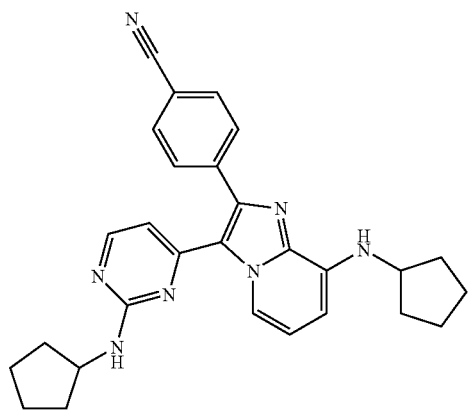

In a similar manner as described in Example 3 from 4-{8-chloro-3-[2-(cyclopentylamino)-4-pyrimidinyl]imidazo[1,2-α]pyridin-2-yl}benzonitrile (73 mg, 0.18 mmol) and cyclopentylamine was formed 4-{8-(cyclopentylamino)-3-[2-(cyclopentylamino)-4-pyrimidinyl]imidazo[1,2-α]pyridin-2-yl}benzonitrile (30 mg, 37%) as a yellow solid. ¹H NMR (CDCl₃): δ 8.65 (d, 1H), 8.17 (d, 1H), 7.86 (d, 2H), 7.71 (d, 2H), 6.82 (t, 1H), 6.39 (d, 1H), 6.31 (d, 1H), 5.33 (d, 1H), 5.25 (d, 1H), 4.36 (m, 1H), 3.96 (m, 1H) 2.19–2.08 (m, 4H), 1.84–1.56 (m, 12H); IR (neat) 2225 (cm⁻¹); MS m/z 464 (M+1).

EXAMPLE 27

4-[3-[2-(Cyclopentylamino)-4-pyrimidinyl]-8-(4-morpholinyl)-imidazo[1,2-α]pyridin-2-yl]benzonitrile.

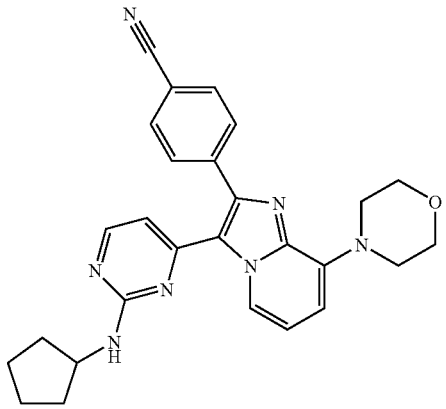

In a similar manner as described in Example 3 from 4-{8-chloro-3-[2-(cyclopentylamino)-4-pyrimidinyl]imidazo[1,2-α]pyridin-2-yl}benzonitrile (88 mg, 0.21 mmol) and morpholine was formed 4-[3-[2-(cyclopentylamino)-4-pyrimidinyl]-8-(4-morpholinyl)imidazo[1,2-α]pyridin-2-yl]benzonitrile (30 mg, 31%) as a yellow solid. ¹H NMR (CDCl₃): δ 8.90 (broad, 1H), 8.22 (m, 1H), 7.89 (d, 2H), 7.70 (d, 2H), 6.86 (t, 1H), 6.63 (d, 1H), 6.45 (d, 1H), 5.28 (broad, 1H), 4.37 (m, 1H), 4.05–4.02 (m, 4H), 3.63–3.59 (m, 4H), 2.20–2.08 (m, 2H), 1.86–1.58 (m, 6H); MS m/z 466 (M+1).

EXAMPLE 28

4-[3-[2-(Cyclopentylamino)-4-pyrimidinyl]-8-(4-morpholinyl)imidazo[1,2-α]pyridin-2-yl]benzamide.

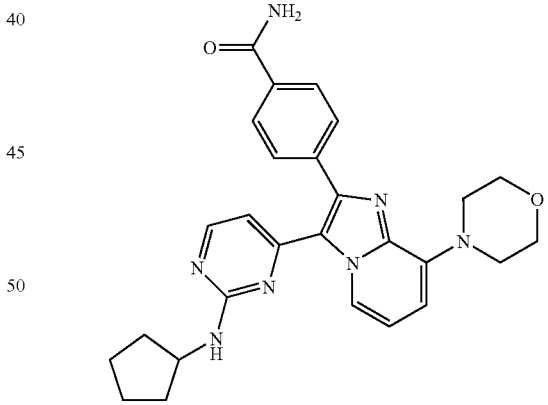

To a cold (0° C.) solution of 4-[3-[2-(cyclopentylamino)-4-pyrimidinyl]-8-(4-morpholinyl)imidazo[1,2-α]pyridin-2-yl]benzonitrile (16 mg, 0.03 mmol) in methanol (2 mL) and tetrahydrofuran (2 mL) was added concentrated ammonium hydroxide (1 mL, 28%) followed by hydrogen peroxide (0.1 mL, 30%). The cold bath was removed and the mixture was stirred at room temperature for 2 hours at which time an additional 0.1 mL of 30% hydrogen peroxide was added. After an additional 14 hours, the reaction was quenched by the addition of saturated aqueous sodium thiosulfate. Ether was added and the layers separated. The organic layer was washed with brine. The aqueous layer was extracted with ether and the combined organics were dried over magnesium sulfate. Filtration and concentration followed by flash chromatography (3% to 10% methanol in dichloromethane) provided 4-[3-[2-(cyclopentylamino)-4-pyrimidinyl]-8-(4-morpholinyl)imidazo[1,2-α]pyridin-2-yl]benzamide (17 mg, 99%) as a white solid. $^1$H NMR (CDCl$_3$): δ 9.03 (broad, 1H), 8.15 (d, 1H), 7.89–7.82 (m, 4H), 6.85 (t, 1H), 6.64 (d, 1H), 6.44 (d, 1H), 6.22–5.79 (broad, 2H), 5.36 (m, 1H), 4.37 (m, 1H), 4.02 (m, 4H), 3.61 (m, 4H), 2.20–2.11 (m, 2H), 1.84–1.57 (m, 6H); MS m/z 484 (M+1).

EXAMPLE 29

4-{8-(Cyclopentylamino)-3-[2-(cyclopentylamino)-4-pyrimidinyl]imidazo[1,2-α]pyridin-2-yl}benzamide.

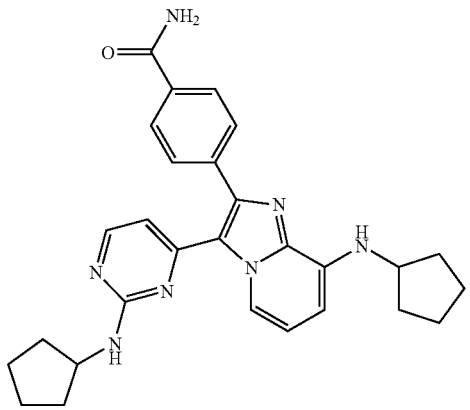

In a similar manner as described in Example 28 from 4-{8-(cyclopentylamino)-3-[2-(cyclopentylamino)-4-pyrimidinyl]imidazo[1,2-α]pyridin-2-yl}benzonitrile (15 mg, 0.03 mmol), ammonium hydroxide, and hydrogen peroxide in tetrahydrofuran/methanol was formed 4-{8-(cyclopentylamino)-3-[2-(cyclopentylamino)-4-pyrimidinyl]imidazo[1,2-α]pyridin-2-yl}benzamide (8 mg, 52%) as a yellow solid. $^1$H NMR (CDCl$_3$): δ 8.76 (broad, 1H), 8.12 (d, 1H), 7.88 (d, 2H), 7.81 (d, 2H), 6.82 (t, 1H), 6.40 (d, 1H), 6.31 (d, 1H), 5.27 (m, 2H), 4.38 (m, 1H), 3.97 (m, 1H), 2.19–2.10 (m, 4H), 1.84–1.58 (m, 12H); MS m/z 482 (M+1).

EXAMPLE 30

N-{4-[8-Chloro-2-(3-nitrophenyl)imidazo[1,2-α]pyridin-3-yl]-2-pyrimidinyl}-N-cyclopentylamine.

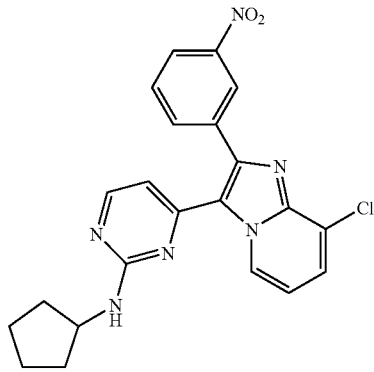

a) 8-Chloro-2-(3-nitrophenyl)imidazo[1,2-α]pyridine.

In a similar manner as described in Example 2 from 2-bromo-1-(3-nitrophenyl)ethanone (4.27 g, 17.5 mmol) and 3-chloro-2-pyridinamine (2.25 g, 17.5 mmol) was formed 8-chloro-2-(3-nitrophenyl)imidazo[1,2-α]pyridine (2.80 g, 59%) as a white solid. $^1$H NMR (CDCl$_3$): δ 8.76 (m, 1H), 8.40 (d, 1H), 8.18 (m, 1H), 8.11 (d, 1H), 8.04 (s, 1H), 7.62 (t, 1H), 7.30 (d, 1H), 6.79 (t, 1H); $^{13}$C NMR (CDCl$_3$): δ 148.65, 144.03, 143.35, 135.11, 132.26, 129.72, 124.51, 124.33, 123.66, 122.82, 120.97, 112.64, 110.56; MS m/z 274 (M+1); Anal. Calcd. for C$_{13}$H$_8$ClN$_3$O$_2$: C, 57.05; H, 2.95; N, 15.35. Found: C, 57.13; H, 3.01; N, 15.20.

b) 8-Chloro-2-(3-nitrophenyl)imidazo[1,2-α]pyridine-3-carbaldehyde.

In a similar manner as described in Example 2 from 8-chloro-2-(3-nitrophenyl)imidazo[1,2-α]pyridine (2.40 g, 8.79 mmol) and phosphorous oxychloride (1.23 mL, 13.18 mmol) in N,N-dimethylformamide (25 mL) was formed 8-chloro-2-(3-nitrophenyl)imidazo[1,2-α]pyridine-3-carbaldehyde (1.7 g, 38%) as a white solid. $^1$H NMR (DMSO-d$_6$): δ 10.11 (s, 1H), 9.54 (d, 1H), 8.72 (s, 1H), 8.43–8.40 (m, 2H), 7.98 (d, 1H), 7.87 (t, 1H), 7.36 (t, 1H); MS m/z 302 (M+1).

c) 1-[8-Chloro-2-(3-nitrophenyl)imidazo[1,2-α]pyridin-3-yl]-2-propyn-1-ol.

In a similar manner as described in Example 2 from 8-chloro-2-(3-nitrophenyl)imidazo[1,2-α]pyridine-3-carbaldehyde (2.70 g, 8.97 mmol) and ethynyl magnesium bromide (54 mL, 0.5 M in tetrahydrofuran, 26.9 mmol) was formed 1-[8-chloro-2-(3-nitrophenyl)imidazo[1,2-α]pyridin-3-yl]-2-propyn-1-ol (2.60 g, 89%) as a white solid. $^1$H NMR (DMSO-d$_6$): δ 8.73 (d, 1H), 8.57 (m, 1H), 8.29 (dd, 1H), 8.19 (d, 1H), 7.83 (t, 1H), 7.64 (d, 1H), 7.11 (t, 1H), 6.64 (d, 1H), 6.09 (m, 1H), 3.67 (d, 1H); MS m/z 328 (M+1).

d) 1-[8-Chloro-2-(3-nitrophenyl)imidazo[1,2-α]pyridin-3-yl]-2-propyn-1-one.

In a similar manner as described in Example 2 from 1-[8-chloro-2-(3-nitrophenyl)imidazo[1,2-α]pyridin-3-yl]-2-propyn-1-ol (2.5 g, 7.64 mmol) was formed 1-[8-chloro-2-(3-nitrophenyl)imidazo[1,2-α]pyridin-3-yl]-2-propyn-1-one (2.20 g, 88%) as a brown solid. $^1$H NMR (DMSO-d$_6$): δ 9.54 (d, 1H), 8.57 (s, 1H), 8.39 (d, 1H), 8.18 (d, 1H), 7.98 (d, 1H), 7.77 (t, 1H), 7.37 (t, 1H), 4.46 (s, 1H); MS m/z 326 (M+1).

e) N-{4-[8-Chloro-2-(3-nitrophenyl)imidazo[1,2-α]pyridin-3-yl]-2-pyrimidinyl}-N-cyclopentylamine.

In a similar manner as described in Example 2 from 1-[8-chloro-2-(3-nitrophenyl)imidazo[1,2-α]pyridin-3-yl]-2-propyn-1-one (1.95 g, 6.0 mmol) and N-cyclopentyl guanidine hydrochloride (1.46 g, 9.0 mmol) and sodium ethoxide in ethanol was formed N-{4-[8-chloro-2-(3-nitrophenyl)imidazo[1,2-α]pyridin-3-yl]-2-pyrimidinyl}-N-cyclopentylamine (1.0 g, 38%) as a yellow solid. $^1$H NMR (CDCl$_3$): δ 9.38–9.20 (broad, 1H), 8.49 (s, 1H), 8.29–8.24 (m, 2H), 8.10 (d, 1H), 7.76–7.68 (m, 2H), 7.52 (d, 1H), 7.10 (t, 1H), 6.47 (broad, 1H), 4.18 (broad, 1H), 1.98–1.85 (m, 2H), 1.75–1.53 (m, 6H); MS m/z 435 (M+1).

EXAMPLE 31

N-Cyclopentyl-4-[8-(4-morpholinyl)-2-(3-nitrophenyl)imidazo[1,2-α]pyridin-3-yl]-2-pyrimidinamine.

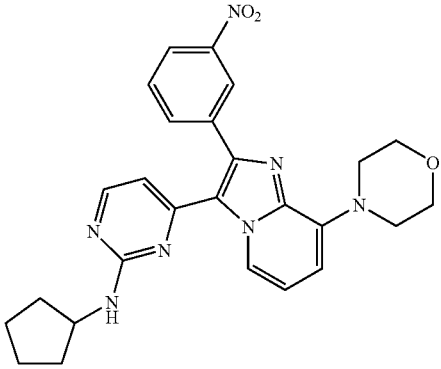

A thick walled glass tube was charged with N-{4-[8-chloro-2-(3-nitrophenyl)imidazo[1,2-α]pyridin-3-yl]-2-pyrimidinyl}-N-cyclopentylamine (44 mg, 0.10 mmol) and morpholine (4 mL). The vessel was sealed and heated to 150° C. for 4 days. The mixture was concentrated in vacuo and purified via flash chromatography on silica gel (2:1 to 1:1 hexanes:ethyl acetate) to provide N-cyclopentyl-4-[8-(4-morpholinyl)-2-(3-nitrophenyl)imidazo[1,2-α]pyridin-3-yl]-2-pyrimidinamine (3 mg, 6%) as a yellow solid. $^1$H NMR (CDCl$_3$): δ 8.92 (m, 1H), 8.67 (s, 1H), 8.21 (d, 1H), 8.13 (m, 1H), 8.01 (d, 1H), 7.53 (t, 1H), 6.83 (t, 1H), 6.61 (d, 1H), 6.40 (d, 1H), 5.33 (m, 1H), 4.33 (m, 1H), 4.00 (m, 4H), 3.58 (m, 4H), 2.14–2.06 (m, 2H), 1.83–1.54 (m, 6H); MS m/z 486 (M+1).

EXAMPLE 32

4-[2-(3-Aminophenyl)-8-chloroimidazo[1,2-α]pyridin-3-yl]-N-cyclopentyl-2-pyrimidinamine.

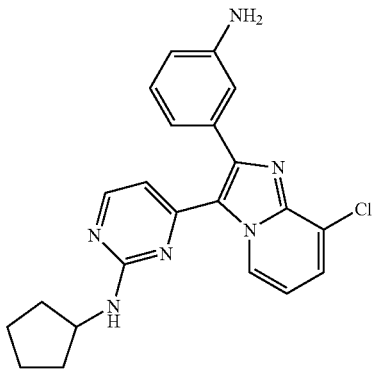

To a solution of N-{4-[8-chloro-2-(3-nitrophenyl)imidazo[1,2-α]pyridin-3-yl]-2-pyrimidinyl}-N-cyclopentylamine (744 mg, 1.71 mmol) in ethanol (25 mL) was added tin(II) chloride dihydrate (1.62 g, 8.57 mmol). The mixture was heated at 80° C. for 4 hours. The solution was cooled to room temperature and quenched by the dropwise addition of saturated aqueous sodium bicarbonate. Dichloromethane was added and the organic layer was washed with brine. The aqueous layer was extracted with dichloromethane and the combined organics were dried over magnesium sulfate. Filtration and concentration followed by flash chromatography (1:1 to 1:2 hexanes:ethyl acetate) provided 4-[2-(3-aminophenyl)-8-chloroimidazo[1,2-α]pyridin-3-yl]-N-cyclopentyl-2-pyrimidinamine (690 mg, 99%) as a foam. $^1$H NMR (CDCl$_3$): δ 9.54 (broad, 1H), 8.10 (d, 1H), 7.39 (d, 1H), 7.16 (t, 1H), 7.05 (m, 1H), 6.97 (d, 1H), 6.84 (t, 1H), 6.72 (m, 1H), 6.51 (d, 1H), 5.18 (d, 1H), 4.33 (m, 1H), 3.72 (broad, 2H), 2.14–2.06 (m, 2H), 1.82–1.54 (m, 6H); MS m/z 405 (M+1).

EXAMPLE 33

2-(3-Aminophenyl)-N-cyclopentyl-3-[2-(cyclopentylamino)-4-pyrimidinyl]imidazo[1,2-α]pyridin-8-amine.

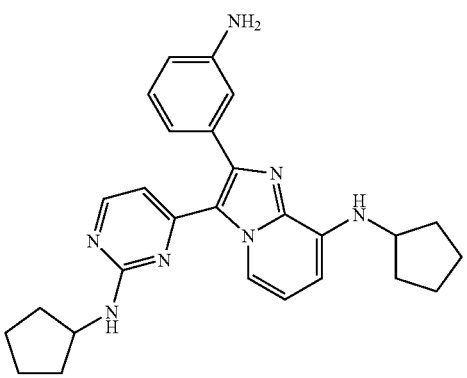

In a similar manner as described in Example 3 from 4-[2-(3-aminophenyl)-8-chloroimidazo[1,2-α]pyridin-3-yl]-N-cyclopentyl-2-pyrimidinamine (100 mg, 0.25 mmol) and cyclopentylamine was formed 2-(3-aminophenyl)-N-cyclopentyl-3-[2-(cyclopentylamino)-4-pyrimidinyl]imidazo[1,2-α]pyridin-8-amine (40 mg, 36%) as a yellow solid. $^1$H NMR (CDCl$_3$): δ 8.89 (broad, 1H), 8.03 (s, 1H), 7.16 (m, 1H), 6.97–6.95 (m, 2H), 6.76–6.68 (m, 2H), 6.43 (d, 1H), 6.25 (d, 1H), 5.28 (broad, 2H), 4.33 (m, 1H), 3.91 (m, 1H), 3.72 (broad, 2H), 2.09–2.03 (m, 4H), 1.82–1.54 (m, 12H); MS m/z 454 (M+1).

EXAMPLE 34

N-Cyclopentyl-3-[2-(cyclopentylamino)-4-pyrimidinyl]-2-{3-[(cyclopropylmethyl)amino]phenyl}imidazo[1,2-α]pyridin-8-amine and

EXAMPLE 35

2-{3-[Bis(cyclopropylmethyl)amino]phenyl}-N-cyclopentyl-3-[2-(cyclopentylamino)-4-pyrimidinyl]imidazo[1,2-α]pyridin-8-amine.

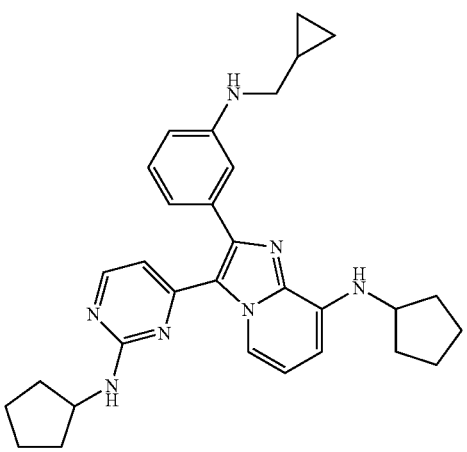

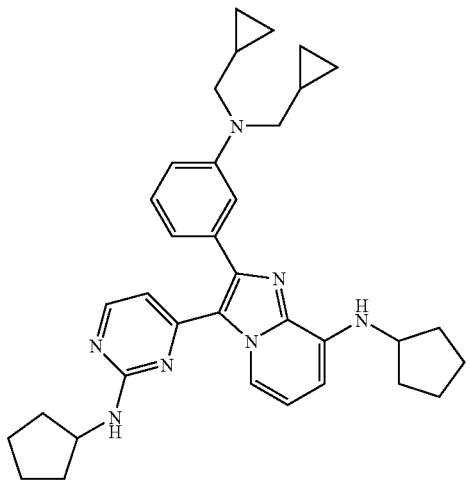

To a solution of 2-(3-aminophenyl)-N-cyclopentyl-3-[2-(cyclopentylamino)-4-pyrimidinyl]imidazo[1,2-α]pyridin-8-amine (26 mg, 0.06 mmol) in 1,2-dichloroethane (3 mL) was added cyclopropane carboxaldehyde (5.3 μL, 0.08 mmol), acetic acid (2 drops) and sodium triacetoxyborohydride (25 mg, 0.11 mmol). The mixture was stirred at room temperature for 2 hours and then quenched by the addition of saturated aqueous sodium bicarbonate. Ether was added and the layers separated. The organic layer was washed with brine. The aqueous layer was extracted with ether and the combined organics were dried over magnesium sulfate. Filtration and concentration followed by flash chromatography (3:1 to 2:1 hexanes:ethyl acetate) eluted first 2-{3-[bis(cyclopropylmethyl)amino]phenyl}-N-cyclopentyl-3-[2-(cyclopentylamino)-4-pyrimidinyl]imidazo[1,2-α]pyridin-8-amine (3.5 mg, 10%) (Example 35) as an oil followed by N-cyclopentyl-3-[2-(cyclopentylamino)-4-pyrimidinyl]-2-{3-[(cyclopropylmethyl)amino]phenyl}imidazo[1,2-α]pyridin-8-amine (11.5 mg, 40%) (Example 34) as a yellow solid. For Example 34: $^1$H NMR (CDCl$_3$): δ 8.96 (d, 1H), 8.06 (d, 1H), 7.23 (t, 1H), 6.95–6.92 (m, 2H), 6.80 (t, 1H), 6.67 (d, 1H), 6.30 (d, 1H), 5.32 (m, 1H), 5.21 (m, 1H), 4.39 (m, 1H), 3.95 (m, 1H), 3.00 (d, 2H), 2.17–2.09 (m, 4H), 1.82–1.59 (m, 12H), 1.12 (m, 1H), 0.57 (m, 2H), 0.26 (m, 2H); MS m/z 508 (M+1). For Example 35: $^1$H NMR (CDCl$_3$): δ 8.91 (broad, 1H), 8.00 (d, 1H), 7.23 (m, 1H), 7.00 (s, 1H), 6.90 (d, 1H), 6.84 (dd, 1H), 6.76 (t, 1 h), 6.46 (d, 1H), 6.26 (d, 1H), 5.28 (d, 1H), 5.14 (m, 1H), 4.34 (m, 1H), 3.91 (m, 1H), 3.23 (d, 4H), 2.14–2.04 (m, 4H), 1.82–1.53 (m, 12H), 0.99 (m, 2H), 0.45 (m, 4H), 0.17 (m, 4H); MS m/z 562 (M+1). For Example 35 this material was treated with anhydrous hydrochloric acid in ether to provide the corresponding hydrochloride salt as a yellow solid.

EXAMPLE 36

3-{8-Chloro-3-[2-(cyclopentylamino)-4-pyrimidinyl]imidazo[1,2-α]pyridin-2-yl}benzonitrile.

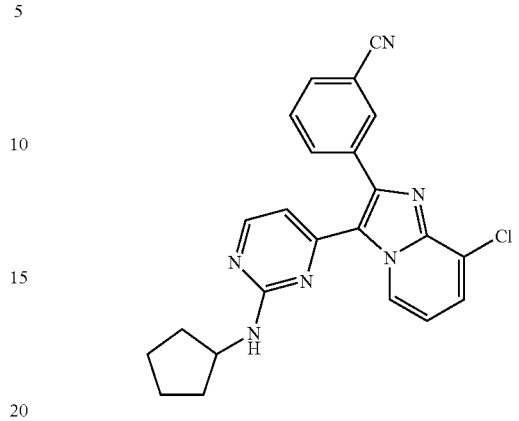

a) 3-(8-Chloroimidazo[1,2-α]pyridin-2-yl)benzonitrile.

In a similar manner as described in Example 2 from 3-(bromoacetyl)benzonitrile (2.45 g, 10.9 mmol) and 3-chloro-2-pyridinamine (1.40 g, 10.9 mmol) was formed 3-(8-chloroimidazo[1,2-α]pyridin-2-yl)benzonitrile (1.67 g, 61%) as a tan solid. $^1$H NMR (DMSO-d$_6$): δ 8.67 (s, 1H), 8.56 (d, 1H), 8.39 (s, 1H), 8.32 (d, 1H), 7.80 (d, 1H), 7.67 (t, 1H), 7.49 (d, 1H), 6.93 (t, 1H); MS m/z 254 (M+1).

b) 3-(8-Chloro-3-formylimidazo[1,2-α]pyridin-2-yl)benzonitrile.

In a similar manner as described in Example 2 from 3-(8-chloroimidazo[1,2-α]pyridin-2-yl)benzonitrile (1.65 g, 6.52 mmol) and phosphorous oxychloride (0.91 mL, 9.78 mmol) in N,N-dimethylformamide (20 mL) was formed 3-(8-chloro-3-formylimidazo[1,2-α]pyridin-2-yl)benzonitrile (1.80 g, 98%) as a white solid. $^1$H NMR (DMSO-d$_6$): δ 10.07 (s, 1H), 9.53 (d, 1H), 8.40 (s, 1H), 8.28 (d, 1H), 8.03 (d, 1H), 7.97 (d, 1H), 7.78 (t, 1H), 7.35 (t, 1H); MS m/z 282 (M+1).

c) 3-[8-Chloro-3-(1-hydroxy-2-propynyl)imidazo[1,2-α]pyridin-2-yl]benzonitrile.

In a similar manner as described in Example 2 from 3-(8-chloro-3-formylimidazo[1,2-α]pyridin-2-yl)benzonitrile (1.79 g, 6.34 mmol) and ethynyl magnesium bromide (15.23 mL, 0.5 M in tetrahydrofuran, 7.62 mmol) was formed 3-[8-chloro-3-(1-hydroxy-2-propynyl)imidazo[1,2-α]pyridin-2-yl]benzonitrile (1.94 g, 99%) as a white solid. $^1$H NMR (CDCl$_3$): δ 8.62 (d, 1H), 8.85 (s, 1H), 7.80 (d, 1H), 7.58 (d, 1H), 7.49 (t, 1H), 7.35 (d, 1H), 6.84 (t, 1H), 6.02 (d, 1H), 3.72 (broad, 1H), 2.69 (d, 1H); MS m/z 308 (M+1).

d) 3-(8-Chloro-3-propioloylimidazo[1,2-α]pyridin-2-yl)benzonitrile.

In a similar manner as described in Example 2 from 3-[8-chloro-3-(1-hydroxy-2-propynyl)imidazo[1,2-α]pyridin-2-yl]benzonitrile (1.0 g, 3.25 mmol) was formed 3-(8-chloro-3-propioloylimidazo[1,2-α]pyridin-2-yl)benzonitrile (950 mg, %) as a brown solid. $^1$H NMR (CDCl$_3$): δ 9.72 (d, 1H), 8.09 (s, 1H), 8.01 (d, 1H), 7.83 (d, 1H), 7.75 (d, 1H), 7.63 (t, 1H), 7.20 (t, 1H), 2.95 (s, 1H); MS m/z 306 (M+1).

e) 3-{8-Chloro-3-[2-(cyclopentylamino)-4-pyrimidinyl]imidazo[1,2-α]pyridin-2-yl}benzonitrile.

In a similar manner as described in Example 2 from 3-(8-chloro-3-propioloylimidazo[1,2-α]pyridin-2-yl)benzonitrile (950 mg, 3.11 mmol) and N-cyclopentyl guanidine hydrochloride (1.01 g, 6.23 mmol) and potassium carbonate in ethanol was formed 3-{8-chloro-3-[2-(cyclopentylamino)-4-pyrimidinyl]imidazo[1,2-α]pyridin-2-yl}benzonitrile (170 mg, 13%) as a yellow solid. $^1$H NMR (CDCl$_3$): δ 9.39 (broad, 1H), 8.20 (d, 1H), 8.08 (s, 1H), 7.96 (d, 1H), 7.71 (d, 1H), 7.55 (t, 1H), 7.47 (d, 1H), 6.92 (t, 1H), 6.38 (d, 1H), 5.39 (broad, 1H), 4.36 (m, 1H), 2.22–2.07 (m, 2H), 1.84–1.58 (m, 6H); MS m/z 415 (M+1).

EXAMPLE 37

3-{8-(Cyclopentylamino)-3-[2-(cyclopentylamino)-4-pyrimidinyl]imidazo[1,2-α]pyridin-2-yl}benzonitrile.

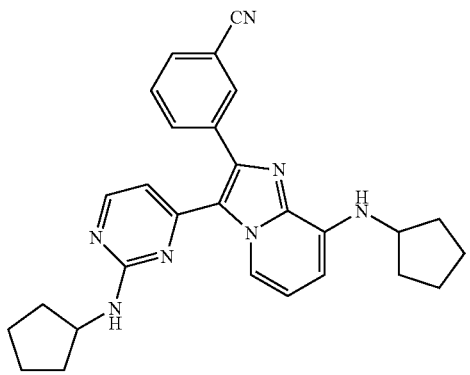

In a similar manner as described in Example 3 from 3-{8-chloro-3-[2-(cyclopentylamino)-4-pyrimidinyl]imidazo[1,2-α]pyridin-2-yl}benzonitrile (125 mg, 0.30 mmol) and cyclopentylamine was formed 3-{8-(cyclopentylamino)-3-[2-(cyclopentylamino)-4-pyrimidinyl]imidazo[1,2-α]pyridin-2-yl}benzonitrile (60 mg, 43%) as a yellow solid. $^1$H NMR (CDCl$_3$): δ 8.62 (broad, 1H), 8.12 (d, 1H), 8.06 (s, 1H), 7.88 (d, 1H), 7.63 (d, 1H), 7.48 (t, 1H), 6.78 (t, 1H), 6.33 (d, 1H), 6.27 (d, 1H), 5.26 (d, 1H), 5.20 (d, 1H), 4.32 (m, 1H), 3.92 (m, 1H), 2.14–2.06 (m, 4H), 1.80–1.51 (m, 12H); MS m/z 464 (M+1).

EXAMPLE 38

N-Cyclopentyl-4-[6,8-dichloro-2-(4-fluorophenyl)imidazo[1,2-α]pyridin-3-yl]-2-pyrimidinamine.

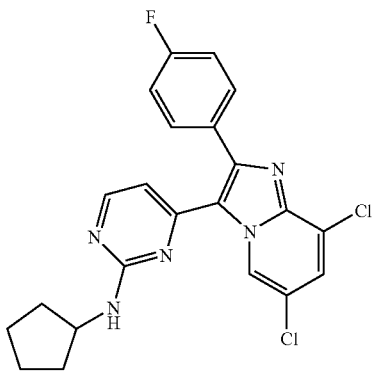

a) 2-Amino-3,5-dichloropyridine.

2,3,5-Trichloropyridine (20 g, 0.11 moles) was placed in a steel bomb and treated with ammonium hydroxide (300 mL) at 190° C. in similar manner as described in Example 2 to give 2-amino-3,5-dichloropyridine (15 g) as a white solid. $^1$H NMR (CDCl$_3$) δ 7.92 (d, 1H), 7.48 (d, 1H), 5.1 (broad s, 2H); MS m/z 163 (M+H).

b) 6,8-Dichloro-2-(4-fluorophenyl)imidazo[1,2-α]pyridine.

In a similar manner as described in Example 2 from 2-amino-3,5-dichloropyridine (7.0 g, 43 mmol), 2-bromo-4'-fluoroacetophenone (9.6 g, 44 mmol) and sodium bicarbonate (4.0 g, 44 mmol) was obtained, after recrystallization from methanol, 6,8-dichloro-2-(4-fluorophenyl)imidazo[1,2-α]pyridine (8 g, 67%) as a solid. $^1$H NMR (CDCl$_3$): δ 8.10 (s, 1H), 7.94 (q, 2H), 7.81 (s, 1H), 7.26 (s, 1H), 7.12 (t, 2H); $^{19}$F NMR (CDCl$_3$) δ −113.4; MS m/z 282 (M+1).

c) 6,8-Dichloro-2-(4-fluorophenyl)imidazo[1,2-α]pyridine-3-carbaldehyde.

6,8-Dichloro-2-(4-fluorophenyl)imidazo[1,2-α]pyridine (6 g, 0.021 moles) was treated with phosphorous oxychloride (3.0 mL, 33 mmol) in N,N-dimethylformamide in a similar manner as described in Example 2 to give 6,8-dichloro-2-(4-fluorophenyl)imidazo[1,2-α]pyridine-3-carbaldehyde (4.9 g, 75%) as a white solid. $^1$H NMR (CDCl$_3$): δ 10.05 (s, 1H), 9.69 (d, 1H), 7.86 (q, 2H), 7.65 (d, 1H), 7.25 (t, 2H); $^{19}$F NMR (CDCl$_3$) δ −110.3; MS m/z 309 (M+1).

d) 1-[6,8-Dichloro-2-(4-fluorophenyl)imidazo[1,2-α]pyridin-3-yl]-2-propyn-1-one.

In a similar manner as described in Example 2 from 6,8-dichloro-2-(4-fluorophenyl)imidazo[1,2-α]pyridine-3-carbaldehyde (6 g, 0.019 mmol) was obtained 1-[6,8-dichloro-2-(4-fluorophenyl)imidazo[1,2-α]pyridin-3-yl]-2-propyn-1-one (1.6 g, 25%) as a yellow solid. $^1$H NMR (CDCl$_3$) δ 9.74 (d, 1H), 7.7 (m, 3H), 7.15 (t, 2H), 2.92 (s, 1H); $^{19}$F NMR (CDCl$_3$) δ −111.1; MS m/z 333 (M+1).

e) N-Cyclopentyl-4-[6,8-dichloro-2-(4-fluorophenyl)imidazo[1,2-α]pyridin-3-yl]-2-pyrimidinamine.

From 1-[6,8-dichloro-2-(4-fluorophenyl)imidazo[1,2-α]pyridin-3-yl]-2-propyn-1-one (700 mg, 2.1 mmol), cyclopentyl guanidine hydrochloride (514 mg, 3.2 mmol) and potassium carbonate (440 mg, 3.2 mmol) in ethanol was obtained N-cyclopentyl-4-[6,8-dichloro-2-(4-fluorophenyl)imidazo[1,2-α]pyridin-3-yl]-2-pyrimidinamine (720 mg, 78%) as a solid. $^1$H NMR (CDCl$_3$) δ 9.77 (broad s, 1H), 8.10 (d, 1H), 7.64 (q, 2H), 7.44 (d, 1H), 7.12 (t, 2H), 6.39 (d, 1H), 5.4 (m, 1H), 4.34 (m, 1H), 2.0–2.1 (m, 2H), 1.4–1.9 (m, 6H); $^{19}$F NMR (CDCl$_3$) δ −112.5; MS m/z 442 (M+1).

EXAMPLE 39

N-{4-[6-Chloro-8-(cyclopentylamino)-2-(4-fluorophenyl)imidazo[1,2-α]pyridin-3-yl]-2-pyrimidinyl}-N-cyclopentylamine.

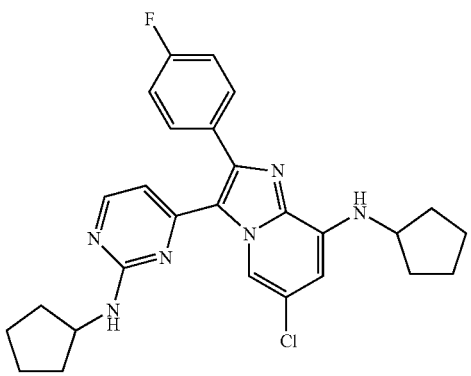

In a similar manner as described in Example 3 from N-cyclopentyl-4-[6,8-dichloro-2-(4-fluorophenyl)imidazo[1,2-α]pyridin-3-yl]-2-pyrimidinamine (250 mg, 0.57 mmol) and cyclopentylamine was obtained N-{4-[6-chloro-8-(cyclopentylamino)-2-(4-fluorophenyl)imidazo[1 2-α]pyridin-3-yl]-2-pyrimidinyl}-N-cyclopentylamine (140 mg, 50%) as a solid. $^1$H NMR (CDCl$_3$) δ 9.03 (broad s, 1H), 8.06 (d, 1H), 7.61 (q, 2H), 7.11 (t, 2H), 6.33 (d, 1H), 6.24 (d, 1H), 5.34 (d, 1H), 5.26 (d, 1H), 4.36 (m, 1H), 3.91 (m, 1H), 2.0–2.1 (m, 4H), 1.4–1.9 (m, 12H); $^{19}$F NMR (CDCl$_3$) δ −113.4; MS m/z 491 (M+1).

EXAMPLE 40

N-Cyclopentyl-4-[6,8-dibromo-2-(4-fluorophenyl)imidazo[1,2-a]pyridin-3-yl]-2-pyrimidinamine

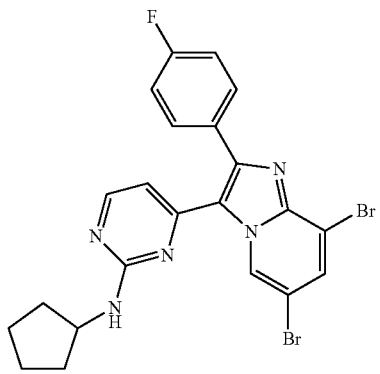

a) 6,8-dibromo-2-(4-fluorophenyl)imidazo[1,2-a]pyridine

In a similar manner as described in Example 2 from 2-amino-3,5-dibromopyridine (15.0 g, 60 mmol), 2-bromo-4'-fluoroacetophenone (13 g, 60 mmol) and anhydrous potassium carbonate (8.22 g, 60 mmol) was obtained, after recrystallization from ethanol, 6,8-dibromo-2-(4-fluorophenyl)imidazo[1,2-a]pyridine (18 g, 82%) as a solid. $^1$H NMR (CDCl$_3$): δ 8.28 (s, 1H), 7.98 (q, 2H), 7.88 (s, 1H), 7.58 (s, 1H), 7.16 (t, 2H); $^{19}$F NMR (CDCl$_3$) δ −113.4; MS m/z 369 (M+1).

b) 1-[6,8-Dibromo-2-(4-fluorophenyl)imidazo[1,2-a]pyridin-3-yl]ethanone

In a similar manner as described in Example 1 from 6,8-dibromo-2-(4-fluorophenyl)imidazo[1,2-a]pyridine (3 g, 8.0 mmol), acetic anhydride (30 mL) and catalytic sulphuric acid was obtained 1-[6,8-dibromo-2-(4-fluorophenyl)imidazo[1,2-a]pyridin-3-yl]ethanone as a yellow solid. $^1$H NMR (CDCl$_3$): δ 9.97 (d, 1H), 7.92 (d, 1H), 7.61 (q, 2H), 7.24 (t, 2H), 2.22 (s, 3H); $^{19}$F NMR (CDCl$_3$) δ −111.5; MS m/z 411 (M+1).

c) N-Cyclopentyl-4-[6,8-dibromo-2-(4-fluorophenyl)imidazo[1,2-a]pyridin-3-yl]-2-pyrimidinamine In a similar manner as described in Example 1 treatment of 1-[6,8-dibromo-2-(4-fluorophenyl)imidazo[1,2-a]pyridin-3-yl]ethanone (850 mg, 2.1 mmol) with N,N-dimethylformamide dimethyl acetal (30 mL), followed by condensation of the resulting (2E)-1-[6,8-dibromo-2-(4-fluorophenyl)imidazo[1,2-a]pyridin-3-yl]-3-(dimethylamino)-2-propen-1-one with cyclopentyl guanidine gave N-cyclopentyl-4-[6,8-dibromo-2-(4-fluorophenyl)imidazo[1,2-a]pyridin-3-yl]-2-pyrimidinamine (600 mg, 54% for two steps) as a yellow solid. $^1$H NMR (CDCl$_3$): δ 9.98 (broad s, 1H), 8.13 (d, 1H), 7.71 (d, 1H), 7.68 (q, 2H), 7.14 (t, 2H), 6.40 (d, 1H), 5.61 (d, 1H), 4.36 (m, 1H), 2.0–2.2 (m, 2H), 1.4–2.0 (m, 6H); $^{19}$F NMR (CDCl$_3$) δ −112.5; MS m/z 530 (M+1).

U17656-53

EXAMPLE 41

N-{4-[6-Bromo-8-(cyclopentylamino)-2-(4-fluorophenyl)imidazo[1,2-a]pyridin-3-yl]-2-pyrimidinyl}-N-cyclopentylamine

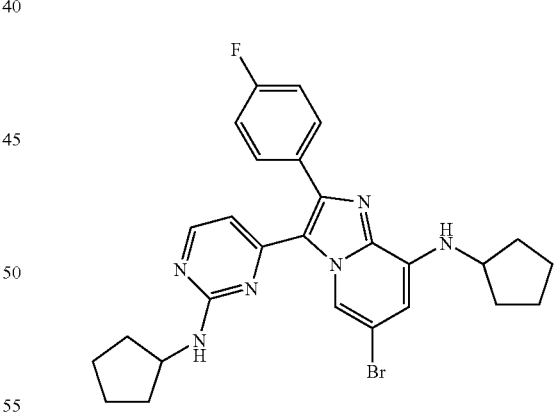

In a similar manner as described in Example 3 from N-cyclopentyl-4-[6,8-dibromo-2-(4-fluorophenyl)imidazo[1,2-a]pyridin-3-yl]-2-pyrimidinamine (100 mg, 0.19 mmol) and cyclopentylamine was obtained N-{4-[6-bromo-8-(cyclopentylamino)-2-(4-fluorophenyl)imidazo[1,2-a]pyridin-3-yl]-2-pyrimidinyl}-N-cyclopentylamine (70 mg, 69%) as a yellowish solid. $^1$H NMR (CDCl$_3$) δ 9.15 (broad s, 1H), 8.09 (d, 1H), 7.64 (q, 2H), 7.15 (t, 2H), 6.38 (m, 2H), 5.36 (d, 1H), 5.30 (d, 1H), 4.40 (m, 1H), 3.93 (m, 1H), 2.0–2.2 (m, 4H), 1.5–2.0 (m, 12H); $^{19}$F NMR (CDCl$_3$) δ −113.5; MS m/z 535 (M+1).

EXAMPLE 42

6-Bromo-N-butyl-3-[2-(cyclopentylamino)-4-pyrimidinyl]-2-(4-fluorophenyl)imidazo[1,2-a]pyridin-8-amine

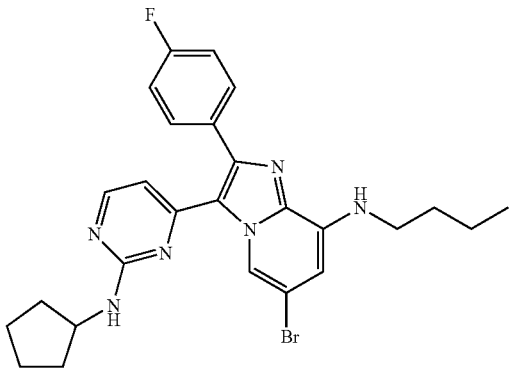

In a similar manner as described in Example 3 from N-cyclopentyl-4-[6,8-dibromo-2-(4-fluorophenyl)imidazo[1,2-a]pyridin-3-yl]-2-pyrimidinamine (100 mg, 0.19 mmol) and n-butylamine was obtained 6-bromo-N-butyl-3-[2-(cyclopentylamino)-4-pyrimidinyl]-2-(4-fluorophenyl)imidazo[1,2-a]pyridin-8-amine (50 mg, 50%) as a yellowish solid. $^1$H NMR (CDCl$_3$) δ 9.20 (broad s, 1H), 8.10 (d, 1H), 7.63 (q, 2H), 7.15 (t, 2H), 6.37 (m, 2H), 5.29 (m, 2H), 4.40 (m, 1H), 3.31 (m, 2H), 2.0–2.1 (m, 2H), 1.4–1.9 (m, 10H), 1.02 (t, 3H); $^{19}$F NMR (CDCl$_3$) δ −113.4; MS m/z 523 (M+1).

EXAMPLE 43

N-Cyclopentyl-4-[2-(4-fluorophenyl)-6,8-di(4-morpholinyl)imidazo[1,2-a]pyridin-3-yl]-2-pyrimidinamine

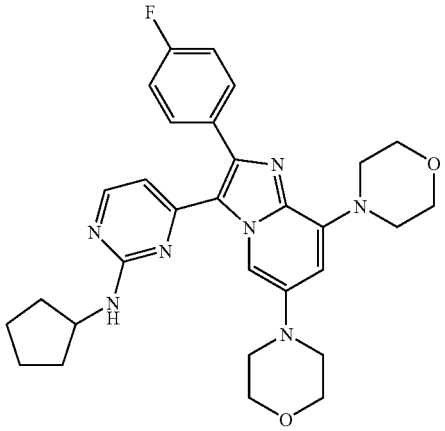

In a similar manner as described in Example 3 from N-cyclopentyl-4-[6,8-dibromo-2-(4-fluorophenyl)imidazo[1,2-a]pyridin-3-yl]-2-pyrimidinamine (100 mg, 0.19 mmol) and morpholine at 100° C. for 3 days was obtained N-cyclopentyl-4-[2-(4-fluorophenyl)-6,8-di(4-morpholinyl)imidazo[1,2-a]pyridin-3-yl]-2-pyrimidinamine (25 mg, 24%) as a yellowish solid. $^1$H NMR (CDCl$_3$) δ 8.66 (s, 1H), 8.11 (d, 1H), 7.66 (q, 2H), 7.10 (t, 2H), 6.49 (d, 1H), 6.43 (d, 1H), 5.24 (d, 1H), 4.45 (m, 1H), 4.03 (m, 4H), 3.94 (m, 4H), 3.60 (m, 4H), 3.13 (m, 4H), 2.0–2.1 (m, 2H), 1.4–1.9 (m, 6H); $^{19}$F NMR (CDCl$_3$) δ −114.1; MS m/z 545 (M+1).

EXAMPLE 44

N-{4-[6-Bromo-2-(4-fluorophenyl)-8-methylimidazo[1,2-a]pyridin-3-yl]-2-pyrimidinyl}-N-cyclopentylamine

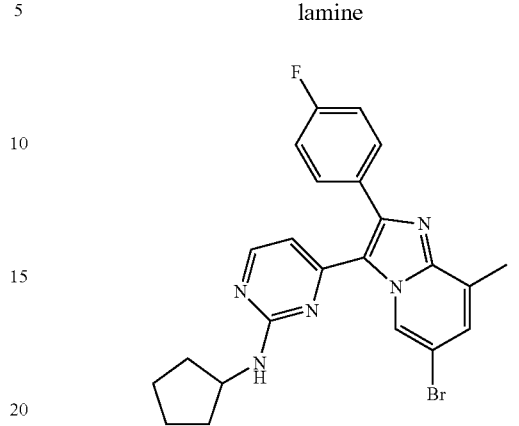

a) 6-Bromo-2-(4-fluorophenyl)-8-methylimidazo[1,2-a]pyridine

In a similar manner as described in Example 2 from 2-amino-5-bromo-3-methylpyridine (14.0 g, 75 mmol), 2-bromo-4'-fluoroacetophenone (19.5 g, 90 mmol) and anhydrous potassium carbonate (12.4 g, 90 mmol) was obtained 6-bromo-2-(4-fluorophenyl)-8-methylimidazo[1,2-a]pyridine (16.2 g, 71%) as a solid. $^1$H NMR (CDCl$_3$): δ 8.16 (s, 1H), 7.96 (q, 2H), 7.77 (s, 1H), 7.16 (t, 2H), 7.09 (s, 1H), 2.68 (s, 3H); $^{19}$F NMR (CDCl$_3$) δ −114.3; MS m/z 305 (M+1).

b) 6-Bromo-2-(4-fluorophenyl)-8-methylimidazo[1,2-a]pyridine-3-carbaldehyde

6-Bromo-2-(4-fluorophenyl)-8-methylimidazo[1,2-a]pyridine (6 g, 0.021 moles) was treated was treated with phosphorous oxychloride (2.8 mL) in N,N-dimethylformamide in a similar manner as described in Example 2 to give 6-bromo-2-(4-fluorophenyl)-8-methylimidazo[1,2-a]pyridine-3-carbaldehyde (5.7 g, 85%) as a white solid. $^1$H NMR (CDCl$_3$): δ 10.04 (s, 1H), 9.73 (s, 1H), 7.86 (q, 2H), 7.53 (s, 1H), 7.25 (t, 2H), 2.75 (s, 3H); $^{19}$F NMR (CDCl$_3$) δ −111.0; MS m/z 334 (M+1).

c) N-{4-[6-Bromo-2-(4-fluorophenyl)-8-methylimidazo[1,2-a]pyridin-3-yl]-2-pyrimidinyl}-N-cyclopentylamine In a similar manner as described in Example 2 from 6-bromo-2-(4-fluorophenyl)-8-methylimidazo[1,2-a]pyridine-3-carbaldehyde (4 g, 0.012 mmol) was obtained 1-[6-bromo-2-(4-fluorophenyl)-8-methylimidazo[1,2-a]pyridin-3-yl]-2-propyn-1-one (1.9 g, 44%) as a solid. This solid was treated with cyclopenylguanidine hydrochloride (1.3 g, 8 mmol) and anhydrous carbonate (1.11 g, 8 mmol) in ethanol as described in Example 2 to give, after silica gel chromatography (1:1 ethyl acetate:hexane), N-{4-[6-bromo-2-(4-fluorophenyl)-8-methylimidazo[1,2-a]pyridin-3-yl]-2-pyrimidinyl}-N-cyclopentylamine (1.2 g, 25%) as a solid. $^1$H NMR (CDCl$_3$) δ 9.83 (broad s, 1H), 8.11 (d, 1H), 7.67 (q, 2H), 7.28 (s, 1H), 7.16 (t, 2H), 6.39 (d, 1H), 5.27 (d, 1H), 4.42 (m, 1H), 2.70 (s, 3H), 2.0–2.1 (m, 2H), 1.5–2.0 (m, 6H); $^{19}$F NMR (CDCl$_3$) δ −113.8; MS m/z 467 (M+1).

EXAMPLE 45

N-Cyclopentyl-3-[2-(cyclopentylamino)-4-pyrimidinyl]-2-(4-fluorophenyl)-8-methylimidazo[1,2-a]pyridin-6-amine

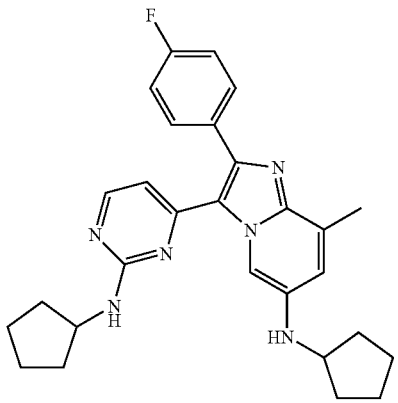

In a similar manner as described in Example 3 from N-{4-[6-bromo-2-(4-fluorophenyl)-8-methylimidazo[1,2-a]pyridin-3-yl]-2-pyrimidinyl}-N-cyclopentylamine (100 mg, 0.21 mmol) and cyclopentylamine was obtained N-cyclopentyl-3-[2-(cyclopentylamino)-4-pyrimidinyl]-2-(4-fluorophenyl)-8-methylimidazo[1,2-a]pyridin-6-amine (40 mg, 40%) as a yellowish foam. $^1$H NMR (CDCl$_3$) δ 8.73 (d, 1H), 8.10 (d, 1H), 7.63 (q, 2H), 7.12 (t, 2H), 6.72 (m, 1H), 6.37 (d, 1H), 5.17 (d, 1H), 4.44 (m, 1H), 3.74 (m, 1H), 3.4 (m, 1H), 2.63 (s, 3H), 2.0–2.1 (m, 4H), 1.4–1.9 (m, 12H); $^{19}$F NMR (CDCl$_3$) δ −114.4; MS m/z 472 (M+1).

EXAMPLE 46

N-Cyclopentyl-4-[2-(4-fluorophenyl)-8-methylimidazo[1,2-a]pyridin-3-yl]-2-pyrimidinamine

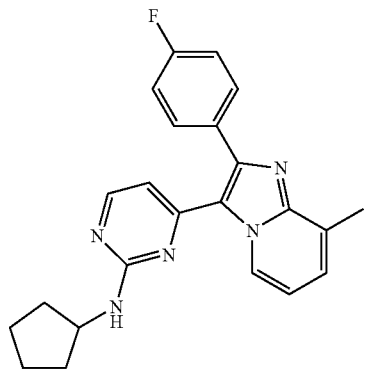

N-{4-[6-Bromo-2-(4-fluorophenyl)-8-methylimidazo[1,2-a]pyridin-3-yl]-2-pyrimidinyl}-N-cyclopentylamine (120 mg, 0.26 mmol) was dissolved in ethanol. To this solution was added 10% palladium on charcoal and the reaction was stirred under hydrogen atmosphere (1 atm) at room temperature for 3 hours. The catalyst was removed by filtration and the resulting solution concentrated to a solid. This solid was purified by silica gel chromatography (1:1 ethyl acetate: hexane) to give 70 mg (70%) of N-cyclopentyl-4-[2-(4-fluorophenyl)-8-methylimidazo[1,2-a]pyridin-3-yl]-2-pyrimidinamine as a yellowish foam. $^1$H NMR (CDCl$_3$) δ 9.45 (d, 1H), 8.12 (d, 1H), 7.67 (q, 2H), 7.15 (m, 3H), 6.86 (t, 1H), 6.39 (d, 1H), 5.26 (d, 1H), 4.41 (m, 1H), 2.71 (s, 3H), 2.0–2.1 (m, 2H), 1.4–1.9 (m, 6H); $^{19}$F NMR (CDCl$_3$) δ −113.7;

EXAMPLE 47

N-{4-[6-Bromo-2-(4-fluorophenyl)imidazo[1,2-a]pyridin-3-yl]-2-pyrimidinyl}-N-cyclopentylamine

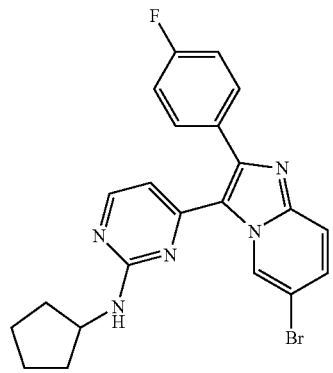

a) 6-Bromo-2-(4-fluorophenyl)imidazo[1,2-a]pyridine

In a similar manner as described in Example 2 from 2-amino-5-bromopyridine (14.0 g, 81 mmol), 2-bromo-4'-fluoroacetophenone (21.0 g, 97 mmol) and anhydrous potassium carbonate (13.4 g, 97 mmol) was obtained, after recrystallization from acetonitrile, 6-bromo-2-(4-fluorophenyl)imidazo[1,2-a]pyridine (12.5 g, 53%) as a solid. $^1$H NMR (CDCl$_3$): δ 8.30 (d, 1H), 7.94 (q, 2H), 7.81 (s, 1H), 7.55 (d, 1H), 7.28 (dd, 1H), 7.17 (t, 2H); $^{19}$F NMR (CDCl$_3$) δ −113.8; MS m/z 291 (M+1).

b) 6-Bromo-2-(4-fluorophenyl)imidazo[1,2-a]pyridine-3-carbaldehyde

6-Bromo-2-(4-fluorophenyl)imidazo[1,2-a]pyridine (7 g, 0.024 moles) was treated with phosphorous oxychloride (3.4 mL, 36 mmol) in N,N-dimethylformamide in a similar manner as described in Example 2 to give, after recrystallization from acetonitrile, 6-bromo-2-(4-fluorophenyl)imidazo[1,2-a]pyridine-3-carbaldehyde (6.12 g, 80%) as a white solid. $^1$H NMR (CDCl$_3$): δ 10.08 (s, 1H), 9.88 (s, 1H), 7.86 (q, 2H), 7.72 (m, 2H), 7.28 (t, 2H); $^{19}$F NMR (CDCl$_3$) δ −110.6; MS m/z 320 (M+1).

c) 1-[6-Bromo-2-(4-fluorophenyl)imidazo[1,2-a]pyridin-3-yl]-2-propyn-1-ol

6-Bromo-2-(4-fluorophenyl)imidazo[1,2-a]pyridine-3-carbaldehyde (5 g, 0.016 moles) was treated with ethynyl magnesium bromide (80 mL of 0.5 M solution in tetrahydrofuran) in a similar manner as described in Example 2 to give, after recrystallization from ethyl acetate, 1-[6-bromo-2-(4-fluorophenyl)imidazo[1,2-a]pyridin-3-yl]-2-propyn-1-ol (3.3 g, 60%) as a white solid. $^1$H NMR (CDCl$_3$): δ 8.87 (s, 1H), 7.77 (m, 2H), 7.54 (d, 1H), 7.39 (t, 2H), 6.62 (d, 1H), 5.99 (s, 1H), 3.74 (d, 1H); $^{19}$F NMR (CDCl$_3$) δ −114.0; MS m/z 345 (M+1).

d) 1-[6-Bromo-2-(4-fluorophenyl)imidazo[1,2-a]pyridin-3-yl]-2-propyn-1-one

1-[6-bromo-2-(4-fluorophenyl)imidazo[1,2-a]pyridin-3-yl]-2-propyn-1-ol (2 g, 5.8 mmoles) was treated with manganese(VI)oxide in a similar manner as described in Example 2 to give, after filtration and silica gel chromatogaphy (2% methanol in dichloromethane), 1-[6-bromo-2-(4-fluorophenyl)imidazo[1,2-a]pyridin-3-yl]-2-propyn-1-one (1.2 g, 60%) as a solid. $^1$H NMR (CDCl$_3$): δ 9.94 (s, 1H), 7.75 (m, 4H), 7.22 (t, 2H), 2.94 (s, 1H); $^{19}$F NMR (CDCl$_3$) δ −111.3.

e) N-{4-[6-Bromo-2-(4-fluorophenyl)imidazo[1,2-a]pyridin-3-yl]-2-pyrimidinyl}-N-cyclopentylamine In a similar manner as described in Example 2 from 1-[6-bromo-2-(4-fluorophenyl)imidazo[1,2-a]pyridin-3-yl]-2-propyn-1-one (1.0 g, 2.9 mmol), cyclopentylguanidine hydrochloride (0.71 g, 4.4 mmol) and anhydrous carbonate (0.6 g, 4.4 mmol), was obtained N-{4-[6-bromo-2-(4-fluorophenyl)imidazo[1,2-a]pyridin-3-yl]-2-pyrimidinyl}-N-cyclopentylamine (0.8 g, 61%) as a solid. $^1$H NMR (CDCl$_3$) δ 10.0 (broad s, 1H), 8.13 (d, 1H), 7.65 (m, 3H), 7.44 (dd, 1H), 7.17 (t, 2H), 6.45 (s, 1H), 5.30 (d, 1H), 4.40 (m, 1H), 2.1 (m, 2H), 1.4–2.0 (m, 6H); $^{19}$F NMR (CDCl$_3$) δ −112.8; MS m/z 452 (M+1).

EXAMPLE 48

N-Cyclopentyl-3-[2-(cyclopentylamino)-4-pyrimidinyl]-2-(4-fluorophenyl)imidazo[1,2-a]pyridin-6-amine and

EXAMPLE 49

N-Cyclopentyl-4-[2-(4-fluorophenyl)imidazo[1,2-a]pyridin-3-yl]-2-pyrimidinamine

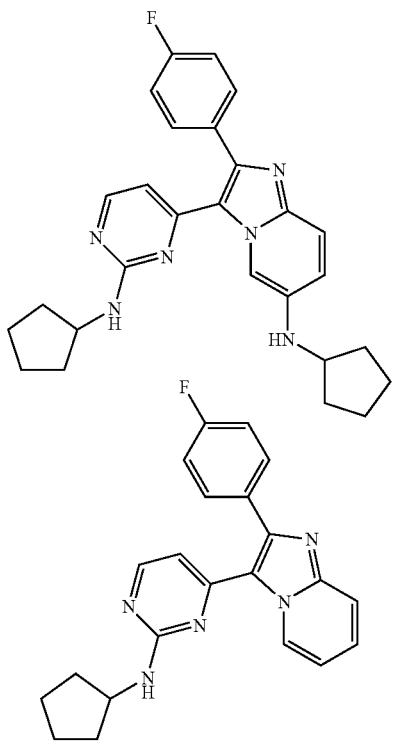

In a similar manner as described in Example 3 from N-{4-[6-bromo-2-(4-fluorophenyl)imidazo[1,2-a]pyridin-3-yl]-2-pyrimidinyl}-N-cyclopentylamine (100 mg, 0.22 mmol) and cyclopentylamine was obtained N-cyclopentyl-3-[2-(cyclopentylamino)-4-pyrimidinyl]-2-(4-fluorophenyl)imidazo[1,2-a]pyridin-6-amine (43 mg, 43%) as a greenish foam and N-cyclopentyl-4-[2-(4-fluorophenyl)imidazo[1,2-a]pyridin-3-yl]-2-pyrimidinamine (10 mg, 12%) as a foam. For N-cyclopentyl-3-[2-(cyclopentylamino)-4-pyrimidinyl]-2-(4-fluorophenyl)imidazo[1,2-a]pyridin-6-amine: $^1$H NMR (CDCl$_3$) δ 8.83 (d, 1H), 8.12 (d, 1H), 7.64 (q, 2H), 7.53 (d, 1H), 7.12 (t, 2H), 6.90 (dd, 1H), 6.42 (d, 1H), 5.18 (d, 1H), 4.45 (m, 1H), 3.75 (m 1H), 3.5 (broad s, 1H), 2.0–2.1 (m, 4H), 1.4–1.9 (m, 12H); $^{19}$F NMR (CDCl$_3$) δ −114.1; MS m/z 457 (M+1). For N-cyclopentyl-4-[2-(4-fluorophenyl)imidazo[1,2-a]pyridin-3-yl]-2-pyrimidinamine: $^1$H NMR (CDCl$_3$) δ 9.58 (d, 1H), 8.14 (d, 1H), 7.60 (m, 3H), 7.37 (t, 1H), 7.15 (t, 2H), 6.96 (t, 1H), 6.46 (d, 1H), 5.25 (d, 1H), 4.40 (m, 1H), 2.1–2.0 (m, 2H), 1.9–1.4 (m, 6H); $^{19}$F NMR (CDCl$_3$) δ −113.4.

U17656-17.

EXAMPLE 50

N-Cyclopentyl-4-[2-(4-fluorophenyl)-6-(4-morpholinyl)imidazo[1,2-a]pyridin-3-yl]-2-pyrimidinamine In a similar manner as described in Example 3 from N-{4-[6-bromo-2-(4-fluorophenyl)imidazo[1,2-a]pyridin-3-yl]-2-pyrimidinyl}-N-cyclopentylamine (100 mg, 0.22 mmol) and morpholine was obtained N-cyclopentyl-4-[2-(4-fluorophenyl)-6-(4-morpholinyl)imidazo[1,2-a]pyridin-3-yl]-2-pyrimidinamine (20 mg, 20%) as a foam. $^1$H NMR (CDCl$_3$) δ 9.08 (s, 1H), 8.12 (d, 1H), 7.65 (m, 3H), 7.25 (dd, 1H), 7.13 (t, 2H), 6.44 (d, 1H), 5.23 (d, 1H), 4.45 (m, 1H), 3.94 (m, 4H), 3.15 (m, 4H), 2.0–2.1 (m, 2H), 1.4–1.9 (m, 6H); $^{19}$F NMR (CDCl$_3$) δ −113.7; MS m/z 459 (M+1).

EXAMPLE 51

3-[2-(cyclopentylamino)-4-pyrimidinyl]-N-cyclopropyl-2-(4-fluorophenyl)imidazo[1,2-a]pyridin-8-amine

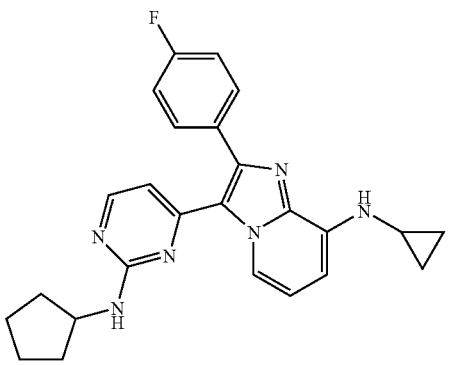

In a similar manner as described in Example 3 from N-cyclopentyl-4-[6,8-dibromo-2-(4-fluorophenyl)imidazo[1,2-a]pyridin-3-yl]-2-pyrimidinamine (70 mg, 0.13 mmol) and cyclopropylamine was obtained 3-[2-(cyclopentylamino)-4-pyrimidinyl]-N-cyclopropyl-2-(4-fluorophenyl)imidazo[1,2-a]pyridin-8-amine (10 mg, 18%) as a foam. $^1$H NMR (CDCl$_3$) δ 8.92 (d, 1H), 8.11 (d, 1H), 7.64 (q, 2H), 7.14 (t, 2H), 6.85 (t, 1H), 6.70 (d, 1H), 6.39 (d, 1H), 5.60 (s, 1H), 5.21 (d, 1H), 4.40 (m, 1H), 2.62 (m, 1H), 2.15 (m, 2H), 0.6–1.9 (m, 10H); $^{19}$F NMR (CDCl$_3$) δ −113.83; MS m/z 430 (M+1).

EXAMPLE 52

2-[4-(Allyloxy)phenyl]-N-cyclopentyl-3-[2-(cyclopentylamino)-4-pyrimidinyl]imidazo[1,2-a]pyridin-8-amine

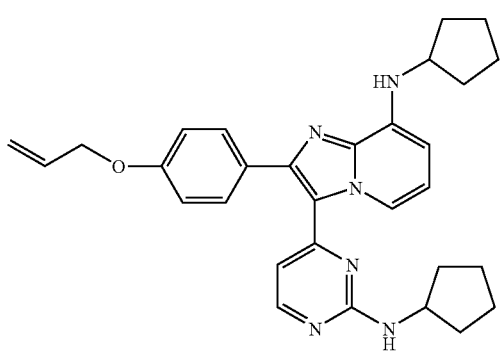

To a solution of 4-{8-(cyclopentylamino)-3-[2-(cyclopentylamino)-4-pyrimidinyl]imidazo[1,2-a]pyridin-2-yl}phenol (110 mg, 0.24 mmol) in N,N-dimethylformamide (5 mL) was added allyl bromide (27 μL, 0.31 mmol) and cesium carbonate (160 mg, 0.48 mmol). The mixture was heated at 80° C. for 3 hours. The mixture was allowed to cool to room temperature and water was added. The mixture was extracted with ethyl acetate. The ethyl acetate phase was dried (magnesium sulfate), filtered and concentrated to a solid. The residue was purified by flash chromatography (1:1 ethyl acetate:hexanes) to give 2-[4-(allyloxy)phenyl]-N-cyclopentyl-3-[2-(cyclopentylamino)-4-pyrimidinyl]imidazo[1,2-a]pyridin-8-amine (40 mg, 34%) as a yellow foam. $^1$H NMR (CDCl$_3$): δ 8.87 (d, 1H), 8.04 (d, 1H), 7.57 (d, 2H), 6.95 (d, 2H), 6.75 (t, 1H), 6.40 (d, 1H), 6.26 (d, 1H), 6.1 (m, 1H), 5.43 (d, 1H), 5.30 (m, 3H), 4.58 (d, 2H), 4.35 (m, 1H), 3.92 (m, 1H), 2.10–2.00 (m, 4H), 1.76–1.45 (m, 12H); MS m/z 495 (M+1).

EXAMPLE 53

N-Cyclopentyl-3-[2-(cyclopentylamino)-4-pyrimidinyl]-2-[4-(cyclopropylmethoxy)phenyl]imidazo[1,2-a]pyridin-8-amine

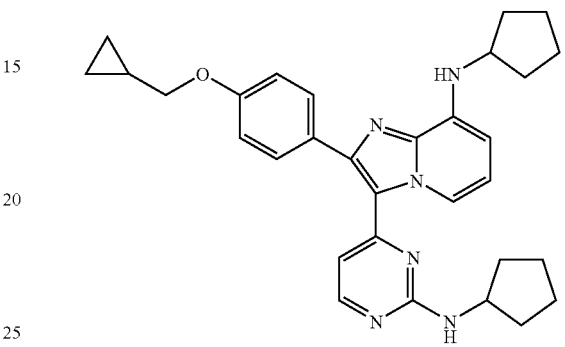

In a similar manner as described before, from 4-{8-(cyclopentylamino)-3-[2-(cyclopentylamino)-4-pyrimidinyl]imidazo[1,2-a]pyridin-2-yl}phenol (65 mg, 0.14 mmol) and cyclopropylmethyl bromide was obtained N-cyclopentyl-3-[2-(cyclopentylamino)-4-pyrimidinyl]-2-[4-(cyclopropylmethoxy)phenyl]imidazo[1,2-a]pyridin-8-amine (34 mg, 47%) as a yellow foam. $^1$H NMR (CDCl$_3$) δ 8.87 (d, 1H), 8.03 (d, 1H), 7.55 (d, 2H), 6.94 (d, 2H), 6.74 (t, 1H), 6.40 (d, 1H), 6.25 (d, 1H), 5.25 (m, 2H), 4.34 (m, 1H), 3.92 (m, 1H), 3.84 (d, 2H), 2.06 (m, 4H), 1.77–1.53 (m, 12H), 0.88 (m, 1H), 0.67 (m, 2H), 0.38 (m, 2H). MS m/z 509 (M+1).

EXAMPLE 54

N-Cyclopentyl-3-[2-(cyclopentylamino)-4-pyrimidinyl]-2-(4-fluorophenyl)-6-(trifluoromethyl)imidazo[1,2-a]pyridin-8-amine

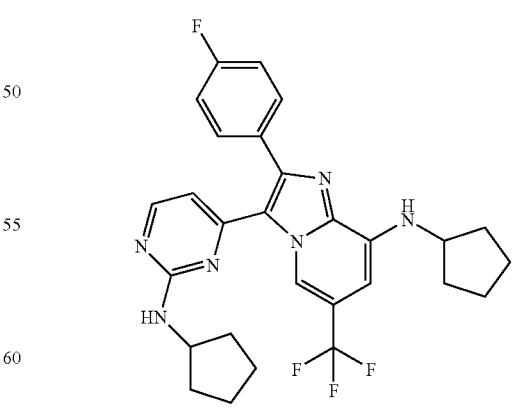

In a similar fashion as described above, N-cyclopentyl-3-[2-(cyclopentylamino)-4-pyrimidinyl]-2-(4-fluorophenyl)-6-(trifluoromethyl)imidazo[1,2-a]pyridin-8-amine was obtained as a yellow solid. R$_f$ 0.31 (4:1 hexanes:ethyl acetate); 1H NMR (CDCl₃) δ 9.32 (br, 1H), 8.03 (d, 1H), 7.60 (m, 2H), 7.09 (t, 2H), 6.35 (d, 1H), 6.30 (s, 1H), 5.41 (d, 1H), 5.38 (d, 1H), 4.35 (m, 1H), 3.95 (m, 1H₁), 2.18–2.10 (m, 4H), 1.81–1.50 (m, 12H); MS m/z 525 (M+1).

EXAMPLE 55

3-{8-(Cyclopentylamino)-3-[2-(cyclopentylamino)pyrimidin-4-yl]imidazo[1,2-a]pyridin-2-yl}benzoic acid

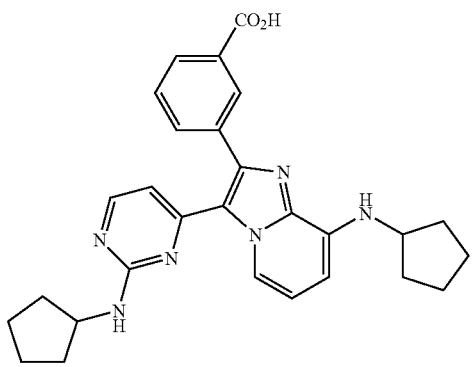

The title compound was prepared in a similar manner to previous examples to give an orange solid as the hydrochloride salt. ¹H NMR (CDCl₃) δ 9.04 (m, 1H), 8.31 (s, 1H), 8.18 (d, 1H), 7.93 (m, 1H), 7.74 (m, 1H), 7.61 (m, 1H), 7.01 (m, 1H), 6.54 (m, 1H), 6.37 (m, 1H), 4.41 (m, 1H), 3.93 (m, 1H), 2.15–1.65 (m, 16H); MS m/z 483 (M+1).

EXAMPLE 56

2-(3-Azidophenyl)-N-butyl-3-[2-(cyclopentylamino)pyrimidin-4-yl]imidazo[1,2-a]pyridin-8-amine

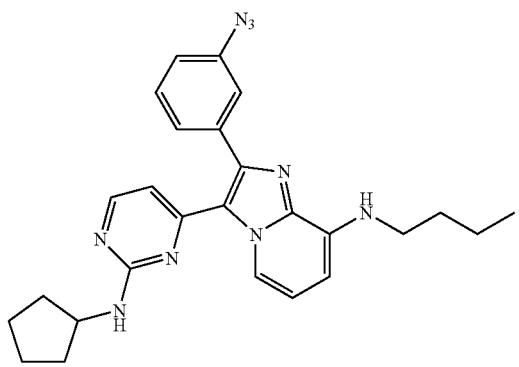

The title compound was prepared in a similar manner to previous examples to give a tan solid. ¹H NMR (CDCl₃) δ 9.49 (broad, 1H), 8.17 (m, 1H), 7.48 (d, 1H), 7.43–7.35 (m, 3H), 7.06 (d, 1H), 7.00 (t, 1H), 6.47 (d, 1H), 5.29 (broad, 1H), 4.55 (t, 2H), 4.35 (m, 1H), 2.15–2.09 (m, 2H), 1.79–1.47 (m, 10H), 1.27 (m, 2H), 0.86 (t, 3H); MS m/z 467 (M+1); IR (film) 2101 cm⁻¹.

EXAMPLE 57

4-[8-(Benzyloxy)-2-(4-fluorophenyl)imidazo[1,2-a]pyridin-3-yl]-N-cyclopentylpyrimidin-2-amine

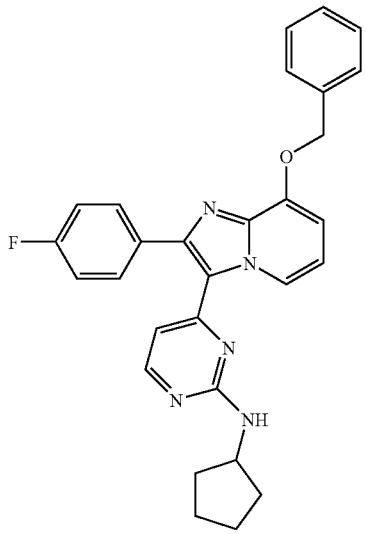

a) 8-(Benzyloxy)-2-(4-fluorophenyl)imidazo[1,2-a]pyridine 3-(Benzyloxy)pyridin-2-amine (2.52 g, 13 mmol) and 2-bromo-1-(4-fluorophenyl)ethanone (2.73 g, 13 mmol) in ethanol (30 mL) were heated at 75° C. for 16 hours. The mixture was concentrated and the residue was purified by silica gel chromatography, eluting with dichloromethane and then 10% methanol in dichloromethane to yield 1.03 g (25%) of 8-(benzyloxy)-2-(4-fluorophenyl)imidazo[1,2-a]pyridine. ¹H NMR (CDCl₃): δ 8.01 (dd, 2H), 7.82 (s, 1H), 7.78 (d, 1H), 7.55 (d, 2H), 7.41 (m, 3H), 7.14 (t, 2H), 6.65 (t, 1H), 6.48 (d, 1H), 5.44 (s, 2H); MS m/z 319 (M+1).

b) 8-(Benzyloxy)-2-(4-fluorophenyl)-3-iodoimidazo[1,2-a]pyridine

To a 0° C. solution of 8-(benzyloxy)-2-(4-fluorophenyl)imidazo[1,2-a]pyridine (0.25 g, 0.79 mmol) in N,N-dimethylformamide (8.0 mL) was added dropwise a solution of N-iodosuccinimide (0.17 g, 0.79 mmol) in N,N-dimethylformamide (4 mL). The reaction was stirred for 2.5 hours and concentrated to a volume of 2 mL The mixture was diluted with ethyl acetate, washed twice with 1M aqueous sodium hydroxide, and concentrated. The residue was purified by silica gel chromatography, eluting with 5% acetone in dichloromethane to yield 0.23 (67%) of 8-(benzyloxy)-2-(4-fluorophenyl)-3-iodoimidazo[1,2-a]pyridine. ¹H NMR (CDCl₃): δ 8.10 (dd, 2H), 7.90 (d, 1H), 7.53 (d, 2H), 7.40 (m, 3H), 7.19 (t, 2H), 6.81 (t, 1H), 6.61 (d, 1H), 5.46 (s, 2H); MS m/z 445 (M+1).

c) 2-(Methylsulfanyl)-4-(tributylstannyl)pyrimidine

To a solution of 4-iodo-2-(methylsulfanyl)pyrimidine (1.0 g, 4.0 mmol) in tetrahydrofuran (6 mL) was added 1,1,1,2,2,2-hexabutyldistannane (4.1 mL, 8.2 mmol), bis(triphenylphoshine)palladium(II)acetate (0.090 g, 0.12 mmol), and 1M tetrabutylammonium fluoride in tetrahydrofuran (12 mL, 12 mmol). The mixture was stirred at room temperature for 3 hours and concentrated. The residue was taken up in ethyl acetate, washed with water, and dried over magnesium sulfate. The solution was concentrated and the residue purified by silica chromatography, eluting with 10% ethyl acetate in hexanes to yield 0.34 g (37%) of 2-(methylsulfanyl)-4-(tributylstannyl)pyrimidine. MS m/z 416 (M+1).

d) 8-(Benzyloxy)-2-(4-fluorophenyl)-3-[2-(methylsulfanyl)pyrimidin-4-yl]imidazo[1,2-a]pyridine To a mixture of 8-(benzyloxy)-2-(4-fluorophenyl)-3-iodoimidazo[1,2-a]pyridine (0.15 g, 0.35 mmol) and dichlorobis(triphenylphosphine)palladium(II) (30 mg, 0.0035 mmol) in toluene (3 mL) was added 2-(methylsulfanyl)-4-(tributylstannyl)pyrimidine (0.19 g, 0.46 mmol). The mixture was heated to 110° C. in a sealed tube for 16 hours. The reaction was allowed to cool and was diluted with ethyl acetate before being poured into a 10% aqueous potassium fluoride solution. The mixture was extracted with ethyl acetate. The organic phase was concentrated and the residue purified by silica chromatography, eluting with dichloromethane and then 5% acetone in dichloromethane to yield 60 mg (39%) of 8-(benzyloxy)-2-(4-fluorophenyl)-3-[2-(methylsulfanyl)pyrimidin-4-yl]imidazo[1,2-a]pyridine. $^1$H NMR (CDCl$_3$): δ 9.18 (d, 1H), 8.33 (d, 1H), 7.68 (dd, 2H), 7.54 (2H), 7.41 (m, 3H), 7.16 (t, 2H), 6.83 (m, 2H), 6.70 (d, 1H), 5.46 (s, 2H), 2.67 (s, 3H). MS m/z 443 (M+1).

e) 4-[8-(Benzyloxy)-2-(4-fluorophenyl)imidazo[1,2-a]pyridin-3-yl]-N-cyclopentylpyrimidin-2-amine To a 0° C. solution of 8-(benzyloxy)-2-(4-fluorophenyl)-3-[2-(methylsulfanyl)pyrimidin-4-yl]imidazo[1,2-a]pyridine (60 mg, 0.14 mmol) in dichloromethane (3 mL) was added 3-chloroperoxybenzoic acid (34 mg, 0.20 mmol). The mixture was allowed to warm to room temperature and stirred for 2 hours. The mixture was diluted with dichloromethane, washed with saturated aqueous sodium bicarbonate, and concentrated. The residue was dissolved in cyclopentylamine and stirred at room temperature for 2.5 hours. The mixture was concentrated and the residue purified by silica chromatography, eluting with 5% acetone in dichloromethane to yield 55 mg (84%) of 4-[8-(benzyloxy)-2-(4-fluorophenyl)imidazo[1,2-a]pyridin-3-yl]-N-cyclopentylpyrimidin-2-amine. $^1$H NMR (CDCl$_3$): δ 9.11 (m, 1H), 8.13 (d, 1H), 7.72 (dd, 2H), 7.54 (d, 2H), 7.41 (m, 3H), 7.13 (t, 2H), 6.76 (t, 1H), 6.64 (d, 1H), 6.44 (d, 1H), 5.46 (d, 2H), 5.30 (m, 1H), 4.37 (m, 1H), 2.13 (m, 2H), 1.75 (m, 6H); MS m/z 480 (M+1).

EXAMPLE 58

5-[2-(Cyclopentylamino)pyrimidin-4-yl]-2-(4-fluorophenyl)imidazo[1,2-a]pyridin-8-ol

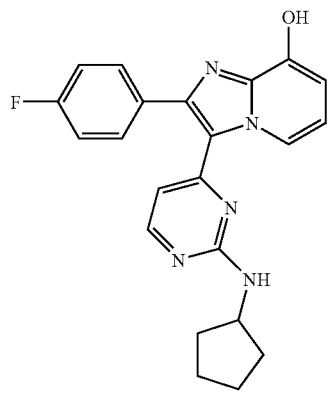

To a solution of 4-[8-(benzyloxy)-2-(4-fluorophenyl)imidazo[1,2-a]pyridin-3-yl]-N-cyclopentylpyrimidin-2-amine (30 mg, 0.063 mmol) in ethanol (2 mL) was added 10% palladium on carbon (4 mg). The mixture was stirred under 10 psi of hydrogen for 3 hours. Additional 10% palladium on carbon (5 mg) was added and the mixture stirred under 15 psi of hydrogen for 1 hour. The catalyst was removed by filtering the mixture through Celite. The filtrate was concentrated and the residue purified by silica chromatography, eluting with 10% acetone in dichloromethane to yield 15 mg (60%) of 3-[2-(cyclopentylamino)pyrimidin-4-yl]-2-(4-fluorophenyl)imidazo[1,2-a]pyridin-8-ol. $^1$H NMR (CDCl$_3$): δ 9.10 (m, 1H), 8.13 (d, 1H), 7.64 (dd, 2H), 7.15 (t, 2H), 6.86 (m, 2H), 6.41 (d, 1H), 5.27 (d, 1H), 4.38 (m, 1H), 2.13 (m, 2H), 1.73 (m, 6H); MS m/z 390 (M+1).

EXAMPLE 59

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloridelsodium citrate; "APE" means a solution of ammonia acetate, ammonia phosphate, EDTA; "PBS" means phosphate buffered saline; and "HRP" means horseradish peroxidase.

a) Tissue Culture and HSV Infection.

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 μM primers, 180 μM dTTP, 20 μM dUTP-digoxigenin (Boehringer Mannheim 1558706), 200 μM each of dATP, dCTP, and dGTP, 1×PCR Buffer II (Perkin Elmer), 2.5 mM MgCl$_2$, 0.025 units/μL of AmpliTaq Gold polymerase (Perkin Elmer), and 5 ng of gel-purified HSV DNA per 100 μL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with XbaI, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration: 3M GuSCN, 50 mM EDTA, 100 μg/ml salmon sperm DNA, 5×Denhardt's solution, 0.25×APE, and 5 ng of the digoxigenin-labeled detection probe). APE is 1.5 M NH$_4$-acetate, 0.15 M ammonium phosphate monobasic, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with 300 μL/well SSC/T buffer then incubated with 75 μL/well anti-digoxigenin-HRP-conjugated antibody (Boehringer Mannheim 1207433, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | IC$_{50}$ (μM) |
| --- | --- |
| 1 | 0.6 |
| 2 | 3.9 |
| 3 | 0.4 |
| 4 | 1.4 |
| 5 | 0.65 |
| 6 | 0.34 |
| 7 | 2.4 |
| 8 | >5.0 |
| 9 | 1.2 |
| 10 | 1.75 |
| 11 | 3.3 |
| 15 | 2.3 |
| 16 | 0.37 |
| 17 | 3.1 |
| 18 | 0.34 |
| 19 | 3.74 |
| 20 | 0.71 |
| 21 | 0.64 |
| 22 | 0.84 |
| 23 | 0.21 |
| 24 | 0.56 |
| 25 | 0.3 |
| 26 | 0.31 |
| 27 | 0.2 |
| 28 | 6.3 |
| 29 | >5.0 |
| 30 | 1.6 |
| 31 | 1.2 |
| 32 | 3.3 |
| 33 | 1.6 |
| 34 | 1.5 |
| 35 | 1.46 |
| 36 | 0.65 |
| 37 | na |
| 38 | 0.95 |
| 39 | 1.4 |
| 40 | 0.79 |
| 41 | 0.18 |
| 42 | 0.29 |
| 43 | 0.47 |
| 44 | 1.2 |
| 45 | 0.14 |
| 46 | 1.5 |

-continued

| Example No. | IC$_{50}$ (μM) |
| --- | --- |
| 47 | 4 |
| 48 | 2.1 |
| 49 | 3.3 |
| 50 | 0.18 |
| 51 | 0.51 |
| 52 | 0.62 |
| 53 | 0.2 |
| 54 | 0.84 |
| 55 | 7.0 |
| 56 | 2.9 |
| 57 | 0.97 |
| 58 | 0.2 |

The results demonstrate that the compounds of the present invention are useful for the treatment and prophylaxis of herpes viral infections.

The invention claimed is:

1. A compound of formula (I):

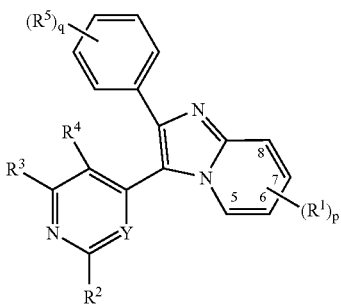

wherein:
p is 0, 1, 2 or 3;
each R$^1$ is the same or different and is independently selected from halo, alkyl, Ay, Het, —OR$^7$, —NR$^7$R$^8$, —NR$^7$Ay, —NHHet, —NHR$^{10}$Ay and NHR$^{10}$Het:
  each R$^7$ and R$^8$ are the same or different and are independently selected from the group consisting of H, alkyl, cycloalkyl, —C(O)R$^9$, —R$^{10}$cycloalkyl, —R$^{10}$OR$^9$, —R$^{10}$CO$_2$R$^9$, and —R$^{10}$NR$^9$R$^{11}$,;
  each R$^9$ and R$^{11}$ are the same or different and are independently selected from the group consisting of H, alkyl, cycloalkyl, and —R$^{10}$cycloalkyl;
  each R$^{10}$ is the same or different and is independently selected from the group consisting of alkyl, alkenyl, alkynyl, cycloalkyl and cycloalkenyl;
Ay is aryl;
Het is a 5- or 6-membered heterocyclic or heteroaryl group;
R$^2$ is selected from the group consisting of halo, alkenyl, cycloalkyl, cycloalkenyl, Ay, Het, —OR$^7$, —OAy, —OHet, —OR$^{10}$Het, —S(O)$_n$R$^9$, —NR$^7$R$^8$, —NHHet, —NHR$^{10}$Het, —R$^{10}$NR$^7$R$^8$ and —R$^{10}$NR$^7$Ay;
n is 0, 1 or 2;
Y is N
R$^3$ and R$^4$ are the same or different and are each independently selected from the group consisting of H, halo, alkyl, alkenyl, cycloalkyl, Ay, Het, —OR$^7$, —OAy, —C(O)R$^7$, —C(O)Ay, —CO$_2$R$^7$, —CO$_2$Ay, —SO$_2$NHR$^9$, —NR$^7$R$^8$, —NR$^7$Ay, —NHHet, —NHR$^{10}$Het, —R$^{10}$cycloalkyl, —R$^{10}$OR$^7$, —R$^{10}$OAy, —R$^{10}$NR$^7$R$^8$ and —R$^{10}$NR$^7$Ay;
q is 0, 1, 2, 3, 4 or 5; and
each R$^5$ is the same or different and is independently selected from the group consisting of halo, alkyl, alkenyl, alkynyl, cycloalkyl, cycloalkenyl, Ay, Het, —OR$^7$, —OAy, —OHet, —OR$^{10}$Ay, —OR$^{10}$Het, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)ₙR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Het, —R¹⁰OR⁹, —R¹⁰C(O)R⁹, —R¹⁰CO₂R⁹, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R⁵ groups together with the atoms to which they are bonded form a C₅₋₆ cycloalkyl or aryl; or a pharmaceutically acceptable salt thereof.

2. The compound according to claim 1 wherein each R¹ is the same or different and is independently selected form the group consisting of halo, alkyl, Het, —NR⁷R⁸, —NR⁷Ay, and —NHHet.

3. The compound according to claim 1 wherein p is 1 or 2.

4. The compound according to claim 1 wherein R² is selected from the group consisting of Het, —OR⁷, —S(O)ₙR⁹, —NR⁷R⁸, —NHHet and —NHR¹⁰Het.

5. The compound according to claim 1 wherein R² is —NR⁷R⁸.

6. The compound according to claim 1 wherein R³ and R⁴ are the same or different and are each independently selected from the group consisting of H, halo, alkyl, Ay, —OR⁷, —CO₂R⁷, —NR⁷R⁸, —R¹⁰OR⁷ and —R¹⁰NR⁷R⁸.

7. The compound according to claim 1 wherein R³ and R⁴ are both H.

8. The compound according to claim 1 wherein q is 0, 1 or 2.

9. The compound according to claim 1 wherein each R⁵ is the same or different and is independently selected from the group consisting of halo, alkyl, alkenyl, Ay, Het, —OR⁷, —OAy, —CO₂R⁹, —C(O)NR⁷R⁸, —C(O)NR⁷Ay, —S(O)₂NR⁷R⁸, —NR⁷R⁸, —NR⁷Ay, —NHR¹⁰Ay, cyano, nitro and azido.

10. The compound according to claim 1 wherein each R⁵ is the same or different and is independently selected from the group consisting of halo, alkyl, —OR⁷, —NR⁷R⁸ and cyano.

11. A compound selected from the group consisting of:
3-[2-(Cyclopentylamino)-4-pyrimidinyl]-2-(4-fluorophenyl)imidazo[1,2-a]pyridin-8-amine;
4-[8-Chloro-2-(4-fluorophenyl)imidazo[1,2-a]pyridin-3-yl]-N-cyclopentyl-2-pyrimidinamine;
N-Cyclopentyl-3-[2-(cyclopentylamino)-4-pyrimidinyl]-2-(4-fluorophenyl)imidazo[1,2-a]pyridin-8-amine;
N-Cyclopentyl-4-[2-(4-fluorophenyl)-8-(1-pyrrolidinyl)imidazo[1,2-a]pyridin-3-yl]-2-pyrimidinamine;
N-Butyl-3-[2-(cyclopentylamino)-4-pyrimidinyl]-2-(4-fluorophenyl)imidazo[1,2-a]pyridin-8-amine;
3-[2-(Cyclopentylamino)-4-pyrimidinyl]-2-(4-fluorophenyl)-N-(2-methoxyethyl)imidazo[1,2-a]pyridin-8-amine;
4-[8-Chloro-2-(4-fluorophenyl)imidazo[1,2-a]pyridin-3-yl]-N-methyl-2-pyrimidinamine;
N-Cyclopentyl-2-(4-fluorophenyl)-3-[2-(methylamino)-4-pyrimidinyl]imidazo[1,2-a]pyridin-8-amine;
4-[8-Chloro-2-(4-methoxyphenyl)imidazo[1,2-a]pyridin-3-yl]-N-cyclopentyl-2-pyrimidinamine;
N-Cyclopentyl-3-[2-(cyclopentylamino)-4-pyrimidinyl]-2-(4-methoxyphenyl)imidazo[1,2-a]pyridin-8-amine;
4-{8-(Cyclopentylamino)-3-[2-(cyclopentylamino)-4-pyrimidinyl]imidazo[1,2-a]pyridin-2-yl}phenol;
4-[8-Chloro-2-(3-mrthoxyphenyl)imidazo[1,2-a]pyridin-3-yl]-N-cyclopentyl-2-pyridinamine;
N-Cyclopentyl-3-[2-(cyclopentylamino)-4-pyridinyl]-2-(3-methoxyphenyl)imidazo[1,2-a]pyridin-8-amine;
3-{8-(Cyclopentylamino)-3-[2-(cyclopentylamino)-4-pyrimidinyl]imidazo[1,2-a]pyridin-2-yl}phenol;
2-[3-(Allyloxy)phenyl]-N-cyclopentyl-3-[2-(cyclopentylamino)-4-pyrimidinyl]imidazo[1,2-a]pyridin-8-amine;
4-[8-Chloro-2-(4-methylphenyl)imidazo[1,2-a]pyridin-3-yl]-N-cyclopentyl-2-pyrimidinamine;
N-Cyclopentyl-3-[2-(cyclopentylamino)-4-pyrimidinyl]-2-(4-methylphenyl)imidazo[1,2-a]pyridin-8-amine;
3-[2-(Cyclopentylamino)-4-pyrimidinyl]-N-(2-methoxyethyl)-2-(4-methylphenyl)imidazo[1,2-a]pyridin-8-amine;
N-Cyclopentyl-4-[2-(4-methylphenyl)-8-(4-morpholinyl)imidazo[1,2-a]pyridin-3-yl]-2-pyrimidinamine;
4-[8-Chloro-2-(2-naphthyl)imidazo[1,2-a]pyridin-3-yl]-N-cyclopropyl-2-pyrimidinamine;
N-Cyclopropy-3-[2-(cyclopropylamino)-4-pyrimidinyl]-2-(2-naphthyl)imidazo[1,2-a]pyridin-8-amine;
4-{8-Chloro-3-[2-(cyclopentylamino)-4-pyrimidinyl]imidazo[1,2-a]pyridin-2-yl}benzonitrile;
4-{8-(Cyclopentylamino)-3-[2-(cyclopentylamino)-4-pyrimidinyl]imidazo[1,2-a]pyridin-2-yl}benzonitrile;
4-[3-[2-(Cyclopentylamino)-4-pyrimidinyl]-8-(4-morpholinyl)imidazo[1,2-a]pyridin-2-yl]benzonitrile;
4-[3-[2-(Cyclopentylamino)-4-pyrimidinyl]-8-(4-morpholinyl)imidazo[1,2-a]pyridin-2-yl]benzamide;
4-{8-(Cyclopentylamino)-3-[2-(cyclopentylamino)-4-pyrimidinyl]imidazo[1,2-a]pyridin-2-yl}benzamide;
N-{4-[8-Chloro-2-(3-nitrophenyl)imidazo[1,2-a]pyridin-3-yl]-2-pyrimidinyl}-N-cyclopentylamine;
N-Cyclopentyl-4-[8-(4-morpholinyl)-2-(3-nitrophenyl)imidazo[1,2-a]pyridin-3-yl]-2-pyrimidinamine;
4-[2-(3-Aminophenyl)-8-chloroimidazo[1,2-a]pyridin-3-yl]-N-cyclopentyl-2-pyrimidinamine;
2-(3-Aminophenyl)-N-cyclopentyl-3-[2-(cyclopentylamino)-4-pyrimidinyl]imidazo[1,2-a]pyridin-8-amine;
N-Cyclopentyl-3-[2-(cyclopentylamino)-4-pyrimidinyl]-2-{3-[(cyclopropylmethyl)amino]phenyl}imidazo[1,2-a]pyridin-8-amine;
2-{3-[Bis(cyclopropylmethyl)amino]phenyl}-N-cyclopentyl-3-[2-(cyclopentylamino)-4-pyrimidinyl]imidazo[1,2-a]pyridin-8-amine;
3-{8-Chloro-3-[2-(cyclopentylamino)-4-pyrimidinyl]imidazo[1,2-a]pyridin-2-yl}benzonitrile;
3-{8-(Cyclopentylamino)-3-[2-(cyclopentylamino)-4-pyrimidinyl]imidazo[1,2-a]pyridin-2-yl}benzonitrile;
N-Cyclopentyl-4-[6,8-dichloro-2-(4-fluorophenyl)imidazo[1,2-a]pyridin-3-yl]-2-pyrimidinamine;
N-{4-[6-Chloro-8-(cyclopentylamino)-2-(4-fluorophenyl)imidazo[1,2-a]pyridin-3-yl]-2-pyrimidinyl}-N-cyclopentylamine;
N-Cyclopentyl-4-[6,8-dibromo-2-(4-fluorophenyl)imidazo[1,2-a]pyridin-3-yl]-2-pyrimidinamine;
N-{4-[6-Bromo-8-(cyclopentylamino)-2-(4-fluorophenyl)imidazo[1,2-a]pyridin-3-yl]-2-pyrimidinyl}-N-cyclopentylamine;
6-Bromo-N-butyl-3-[2-(cyclopentylamino)-4-pyrimidinyl]-2-(4-fluorophenyl)imidazo[1,2-a]pyridin-8-amine;
N-Cyclopentyl-4-[2-(4-fluorophenyl)-6,8-di(4-morpholinyl)imidazo[1,2-a]pyridin-3-yl]-2-pyrimidinamine;
N-{4-[6-Bromo-2-(4-fluorophenyl)-8-methylimidazo[1,2-a]pyridin-3-yl]-2-pyrimidinyl}-N-cyclopentylamine;

N-Cyclopentyl-3-[2-(cyclopentylamino)-4-pyrimidinyl]-2-(4-fluorophenyl)-8-methylimidazo[1,2-a]pyridin-6-amine;
N-Cyclopentyl-4-[2-(4-fluorophenyl)-8-methylimidazo[1,2-a]pyridin-3-yl]-2-pyrimidinamine;
N-{4-[6-Bromo-2-(4-fluorophenyl)imidazo[1,2-a]pyridin-3-yl]-2-pyrimidinyl}-N-cyclopentylamine;
N-Cyclopentyl-3-[2-(cyclopentylamino)-4-pyrimidinyl]-2-(4-fluorophenyl)imidazo[1,2-a]pyridin-6-amine;
N-Cyclopentyl-4-[2-(4-fluorophenyl)imidazo[1,2-a]pyridin-3-yl]-2-pyrimidinamine;
N-Cyclopentyl-4-[2-(4-fluorophenyl)-6-(4-morpholinyl)imidazo[1,2-a]pyridin-3-yl]-2-pyrimidinamine;
3-[2-(cyclopentylamino)-4-pyrimidinyl]-N-cyclopropyl-2-(4-fluorophenyl)imidazo[1,2-a]pyridin-8-amine;
2-[4-(Allyloxy)phenyl]-N-cyclopentyl-3-[2-(cyclopentylamino)-4-pyrimidinyl]imidazo[1,2-a]pyridin-8-amine;
N-Cyclopentyl-3-[2-(cyclopentylamino)-4-pyrimidinyl]-2-[4-(cyclopropylmethoxy)phenyl]imidazo[1,2-a]pyridin-8-amine;
N-Cyclopentyl-3-[2-(cyclopentylamino)-4-pyrimidinyl]-2-(4-fluorophenyl)-6-(trifluoromethyl)imidazo[1,2-a]pyridin-8-amine;
3-{8-(Cyclopentylamino)-3-[2-(cyclopentylamino)pyrimidin-4-yl]imidazo[1,2-a]pyridin-2-yl}benzoic acid;
2-(3-Azidophenyl)-N-butyl-3-[2-(cyclopentylamino)pyrimidin-4-yl]imidazo[1,2-a]pyridin-8-amine;
4-[8-(Benzyloxy)-2-(4-fluorophenyl)imidazo[1,2-a]pyridin-3-yl]-N-cyclopentylpyrimidin-2-amine; and
3-[2-(Cyclopentylamino)pyrimidin-4-yl]-2-(4-fluorophenyl)imidazo[1,2-a]pyridin-8-ol,
and pharmaceutically acceptable salts thereof.

12. A compound of formula (I):

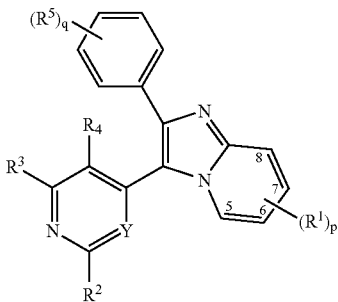

wherein:
p is 0, 1 or 2;
each $R^1$ is the same or different and is independently selected from halo, alkyl, Ay, Het, —$OR^7$, —$NR^7R^8$, —$NR^7Ay$, —NHHet, —$NHR^{10}Ay$ and $NHR^{10}Het$;
each $R^7$ and $R^8$ are the same or different and are independently selected from the group consisting of H, alkyl and cycloalkyl;
each $R^9$ and $R^{11}$ are the same or different and are independently selected from the group consisting of H and alkyl;
each $R^{10}$ is the same or different and is alkyl;
Ay is phenyl optionally substituted with one or more substituents selected from the group consisting of halo, alkyl, alkenyl, cycloalkyl, cycloalkenyl, hydroxyl, alkoxy, cycloalkoxy, alkylhydroxy, mercapto, amino, alkylamine, sulfonamide, cyano, nitro, and azido;
Het is a 5- or 6-membered heterocylic or heteroaryl group;
$R^2$ is selected from the group consisting of Het, —$NR^7R^8$, —NHHet and —$NHR^{10}Het$;
n is 0, 1 or 2;
Y is N;
$R^3$ and $R^4$ are each H;
q is 1 or 2; and
each $R^5$ is the same or different and is independently selected from the group consisting of halo, alkyl, alkenyl, Ay, Het, —$OR^7$, —OAy, —$CO_2R^9$, —C(O)$NR^7R^8$, —C(O)$NR^7Ay$, —$S(O)_2NR^7R^8$, —$NR^7R^8$, —$NR^7Ay$, —$NHR^{10}Ay$, cyano, nitro and azido;
or a pharmaceutically acceptable salt thereof.

13. A process for preparing a compound according to claim 1, wherein $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$NR^7R^8$, —NHHet, —$NHR^{10}$Het, —$R^{10}NR^7R^8$ and —$R^{10}NR^7Ay$; and $R^3$ and $R^4$ are both H, said process comprising reacting a compound of formula (VI):

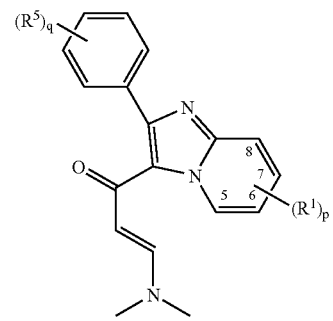

with a compound of formula (VII)

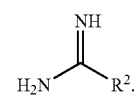

14. A process for preparing a compound according to claim 1 wherein $R^2$ is selected from the group consisting of alkenyl, cycloalkyl, cycloalkenyl, Ay, Het, —$OR^7$, —OAy, —OHet, —$OR^{10}$Het, —$S(O)_nR^9$, —$NR^7R^8$, —NHHet, —$NHR^{10}$Het, —$R^{10}NR^7R^8$ and —$R^{10}NR^7Ay$; $R^3$ is selected from the group consisting of H, alkyl, alkenyl, cycloalkyl, Ay, Het, —$C(O)R^7$, —$CO_2R^7$, —$SO_2NHR^9$, —$NR^7R^8$ (where $R^7$ and $R^8$ are not H)$_1$—$R^{10}OR^7$ and —$R^{10}NR^7R^8$; and $R^4$ is H;

said process comprising reacting a compound of formula (XI):

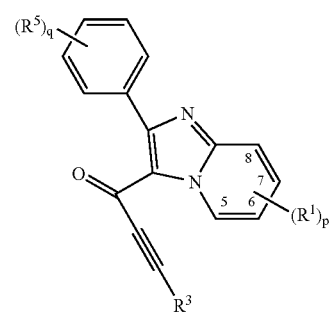

with a compound of formula (VII)

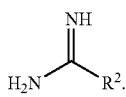

VII

15. A process for preparing a compound according to claim 1, wherein R² is selected from the group consisting of alkenyl, cycloalkyl, cycloalkenyl, Ay, Het, —OR⁷, —OAy, —OHet, —OR¹⁰Het, —NR⁷R⁸, —NHHet, NHR¹⁰Het, —R¹⁰NR⁷R⁸ and —R¹⁰NR⁷Ay, said process comprising reacting a compound of formula (XIV):

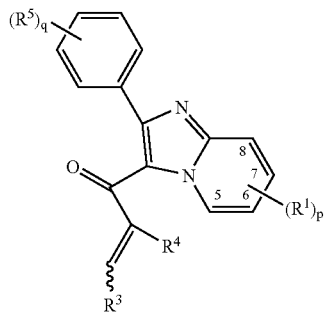

XIV with a compound of formula (VII)

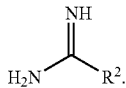

VII

16. A process for preparing a compound according to claim 1, said process comprising reacting a compound of formula (XV):

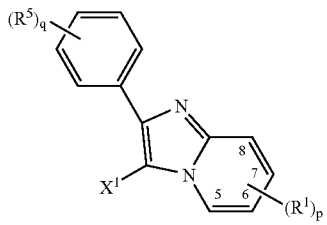

XV wherein $X^1$ is halo;
with a compound of formula (XVI)

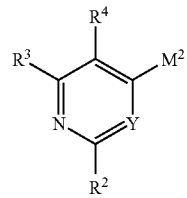

XVI wherein $M^2$ is selected from the group consisting of —B(OH)₂, —B(ORa)₂, —B(Ra)₂, —Sn(Ra)₃, Zn-halide, ZnRa and Mg-halide, where Ra is alkyl or cycloalkyl and halide is halo.

17. A pharmaceutical composition comprising a compound according to claim 1.

18. The pharmaceutical composition according to claim 17 further comprising a pharmaceutically acceptable carrier or diluent.

19. The pharmaceutical composition according to claim 17, further comprising an antiviral agent selected from the group consisting of aciclovir and valaciclovir.

20. A method for the prophylaxis or treatment of a herpes viral infection selected from harpes virus 1 and herpes virus 2 in an animal, said method comprising administering to the animal a therapeutically effective amount of a compound according to claim 1.

21. A method for the treatment of a condition or disease associated with herpes viral infection is selected from herpes simplex virus 1 and herpes simplex virus 2 in an animal, comprising administering to the animal a therapeutically effective amount of a compound according to claim 1.

* * * * *

UNITED STATES PATENT AND TRADEMARK OFFICE
CERTIFICATE OF CORRECTION

PATENT NO. : 7,186,714 B2
APPLICATION NO. : 10/479526
DATED : March 6, 2007
INVENTOR(S) : Gudmundsson et al.

It is certified that error appears in the above-identified patent and that said Letters Patent is hereby corrected as shown below:

Title Page
(56) References Cited, Foreign Patent Documents

WO 0 364 204 A1 10/1989 should read: EP 0 364 204 A1 10/1989

Column 96, Claim 1, line 41 reads:

-- -$R^{10}OR^9$, -$R^{10}CO_2R^9$, and –$R^{10}NR^9R^{11}$,; --

Should read:

-- -$R^{10}OR^9$, -$R^{10}CO_2R^9$, and –$R^{10}NR^9R^{11}$, --

Column 98, Claim 11, lines 1 thru 3 reads:

-- 4-(8-Chloro-2-(3-mrthoxyphenyl)imidazo[1,2-a]pyridine-
3-yl]-N-cyclopcntyl-2-pyridinamine;
N-cyclopentyl-3-[2-cyclopentylamino)-4-pyridinyl]-2- --

Should read:

-- 4-(8-Chloro-2-(3-methoxyphenyl)imidazo[1,2-a]pyridine-
3-yl]-N-cyclopentyl-2-pyrimidinamine;
N-cyclopentyl-3-[2-cyclopentylamino)-4-pyrimidinyl]-2- --

Column 98, Claim 11, line 21:

-- N-Cyclopropy-3-[2-(cyclopropylamino)-4-pyrimidinyl]- --

Should read:

-- N-Cyclopropyl-3-[2-(cyclopropylamino)-4-pyrimidinyl]- --

Column 99, Claim 12, line 61 reads:

-- Capto, amino, alkylamine, sulfonamide, cyano, nitro --

UNITED STATES PATENT AND TRADEMARK OFFICE
CERTIFICATE OF CORRECTION

PATENT NO. : 7,186,714 B2
APPLICATION NO. : 10/479526
DATED : March 6, 2007
INVENTOR(S) : Gudmundsson et al.

It is certified that error appears in the above-identified patent and that said Letters Patent is hereby corrected as shown below:

Should read:

-- Capto, amino, alkylamine, cycloalkylamine, Het, amidinc, carboxy, carboxamide, sulfonamide, cyano, nitro --

Column 99, Claim 12, line 63 reads:

-- Het is a 5- or 6-membered heterocylic or heteroaryl --

Should read:

-- Het is a 5- or 6-membered heterocyclic or heteroaryl --

Column 100, Claim 14, line 47 reads:

-- (where $R^7$ and $R^8$ are not H)$_1$ – $R^{10}OR^7$ and –$R^{10}NR^7R^8$; --

Should read:

-- (where $R^7$ and $R^8$ are not H), – $R^{10}OR^7$ and –$R^{10}NR^7R^8$; --

Column 102, claim 20, line 33 reads:

-- 20. A method for the prophylaxis or treatment of a herpes --

Should read:

-- 20. A method for the treatment of a herpes --

UNITED STATES PATENT AND TRADEMARK OFFICE
CERTIFICATE OF CORRECTION

PATENT NO. : 7,186,714 B2
APPLICATION NO. : 10/479526
DATED : March 6, 2007
INVENTOR(S) : Gudmundsson et al.

It is certified that error appears in the above-identified patent and that said Letters Patent is hereby corrected as shown below:

Column 102, claim 20 line 34 reads:

-- viral infection selected from harpes virus 1 and herpes virus --

Should read:

-- viral infection selected from herpes virus 1 and herpes virus --

Column 102, claim 21, line 39 reads:

-- associated with herpes viral infection is selected from herpes --

Should read:

-- associated with a herpes viral infection selected from herpes --

Signed and Sealed this

Thirty-first Day of July, 2007

JON W. DUDAS
*Director of the United States Patent and Trademark Office*